US006342348B1

(12) United States Patent
Klein et al.

(10) Patent No.: US 6,342,348 B1
(45) Date of Patent: Jan. 29, 2002

(54) NEURTURIN RECEPTOR

(75) Inventors: Robert D. Klein, Palo Alto; Arnon Rosenthal, Burlingame; Mary A. Hynes, San Mateo, all of CA (US)

(73) Assignee: Genetech, Inc., South San Francisco, CA (US)

( * ) Notice: Subject to any disclaimer, the term of this patent is extended or adjusted under 35 U.S.C. 154(b) by 0 days.

(21) Appl. No.: 09/487,685

(22) Filed: Jan. 19, 2000

Related U.S. Application Data

(60) Continuation of application No. 08/957,063, filed on Oct. 24, 1997, now Pat. No. 6,025,157, which is a division of application No. 08/802,805, filed on Feb. 18, 1997.
(60) Provisional application No. 60/038,839, filed on Feb. 18, 1997, now abandoned, and provisional application No. 60/049,818, filed on Jun. 9, 1997, now abandoned.

(51) Int. Cl.[7] .......................... C12Q 1/00; G01N 33/53; C07K 1/00; A23J 1/00

(52) U.S. Cl. .............................. 435/4; 435/7.1; 435/7.8; 435/7.92; 435/7.93; 530/350; 530/412

(58) Field of Search ............................... 435/4, 7.1, 7.8, 435/7.93, 7.92; 530/350, 412, 413

(56) References Cited

FOREIGN PATENT DOCUMENTS

| WO | WO 92/06667 | 5/1991 |
|----|-------------|--------|
| WO | WO 93/06116 | 4/1993 |
| WO | WO 97/44356 | 11/1997 |

OTHER PUBLICATIONS

Rudinger, Characteristics of the amino acids as components of a peptides hormone sequence, Jun. 1976, Peptides Hormones, p. 1–7.*
Andres et al., "Expression of two novel eph–related receptor protein tyrosine kinases in mammary gland development and carcinogenesis" *Oncogene* (erratum) 9:2431 (1994).
Andres et al., "Expression of two novel eph–related receptor protein tyrosine kinases in mamry gland development and carcinogenesis" *Oncogene* 9:1461–1467 (1994).
Arenas et al., "GDNF Prevents Degeneration and Promotes the Phenotype of Brain Noradrenegic Neurons in Vivo" *Neuron* 15:1465–1473 (1995).
Baloh et al., "TrnR2, a Novel Receptor That Mediates Neurturin and GDNF Signaling through Ret" *Neuron* 18(5):793–802 (May 1997).
Beck et al., "Mesencephalic dopaminergic neurons protected by GDNF from axotomy–induced degeneration in the adult brain" *Nature* 373:339–341 (1995).
Bennett et al., "Cloning and Characterization of HTK, a Novel Transmembrane Tyrosine Kinase of the EPH Sub-family" *Journal of Biological Chemistry* 269(19):14211–14218 (1994).
Berkemeyer et al., Neurotrophin–5: A Novel Neurotrophic Factor That Activates trk and trkB *Neuron* 7:857–866 (Nov. 1991).
Buj–Bello et al., "GDNF Is an Age–Specific Survival Factor for Sensory and Automatic Neurons" *Neuron* 15:821–828 (1995).
Buj–Bello et al., "Neurturin responsiveness requires a GPI–linked receptor and the Ret receptor tyrosine kinase" *Nature* 387 (6634):721–724 (Jun. 12, 1997).
Cash et al., "Parkinson's disease and dementia: Norepinephrine and dopamine in locus ceruleus" *Neurology* 37:42–46 (1987).
Chan–Palay et al., "Alterations in Catecholamine Neurons of the Locus Coeruleus in Senile Dementia of the Alzheimer Type and in Parkinson's Disease With and Without Dementia and Depression" *The Journal of Comparative Neurology* 287:373–392 (1989).
Davis et al., "Released from of CNTF receptor α component as a soluble mediator of CNTF responses" *Science* 259:1736–1739 (1993).
Durbec et al., "GDNF signaling through the Ret receptor tyrosine kinase" *Nature* 381:789–792 (1996).
Hefti, F., "Nerve Growth Factor Promotes Survival of Special Chlinergic Neurons After Fimbrial Transactions" *J. of Neuroscience* 6(8):2155–2162 (Aug. 1996).
Hendersen et al., "GNDF: A Potent Survival Factor for Motoneurons Present in Peripheral Nerve and Muscle" *Science* 266:1062–1064 (1994).
Heumann, R., "Regulation of the Synthesis of Nerve Growth Factor" *J. Exp. Biol.* 132:133–150 (1987).
Hillier, L. et al., "The WashU–Merck EST Project" (Accessions No. R02249) (1995).
Hirano, A., "Cytopathology of Amyotrophic Lateral Sclerosis" *Advances in Neurology: Amyotrophic Lateral Sclerosis and Other Motor Neuron Diseases*, Lewis P. Rowland, Raven press, Ltd., Chapter 8, vol. 56:91–101 (1991).
Hirsch et al, "Melanized dopaminergic neurons are differentially susceptible to degeneration in Parkinson's disease" *Nature* 334–348 (1998).
Hornykiewicz, O., "Neurochemical Pathology and the Etiology of Parkinson's Disease: Basic Facts and Hypothetical Possibilities" *Mt. Sinai J. Med.* 55:11–20 (1988).
Ikeda et al., "Specific expression of the ret protoponcogene in human neuroblastoma cell lines" *Oncogene* 5:1291–1296 (1990).

(List continued on next page.)

Primary Examiner—Deborah J. R. Clark
Assistant Examiner—Shin-Lin Chen
(74) *Attorney, Agent, or Firm*—Knobbe, Martens, Olson & Bear, LLP

(57) ABSTRACT

NTNRα, NTNRα extracellular domain (ECD), NTNRα variants, chimeric NTNRα (e.g., NTNRα immunoadhesin), and antibodies which bind thereto (including agonist and neutralizing antibodies) are disclosed. Various uses for these molecules are described, including methods to modulate cell activity and survival by response to NTNRα-ligands, for example NTN, by providing NTNRα to the cell.

21 Claims, 23 Drawing Sheets

OTHER PUBLICATIONS

Jing et al., "GDNF–Induced Activation of the Ret Protein Tyrosine Kinase Is Mediated by GDNFR–α, a Novel Receptor for DFNF" *Cell* 85:1113–1124 (1996).

Jing et al., "FGRα–2 AND GFRα–3 Are Two New Receptors for Ligands of the Family" *Journal of Biological Chemistry* 272(52):33111–33117 (Dec. 26, 1997).

Kaisho et al., "Cloning and expression of a cDNA encoding a novel human neurotrophic factor" *FEBS Letters* 366(1, 2):187–191 (Jun. 1990).

Kearns et al., "GDNF protects nigral dopamine neurons against 6–hydroxydopamine in vivo" *Brain Research* 672:104–111 (1995).

Klein et al., "A GPI–linked protein that interacts with Ret to form a candidate neurturin receptor" *Nature* 387 (6634_: 717–721 (Jubn 12, 1987).

Koke et al., "High Level Expression in *Escherichia coli* and Rapid Purification of Phosphaditylinositol–Specific Phospholipase C from *Bacillus cereus* and *Bacillus thuringiensis*" *Prot. Express. Purification* 2:51–58 (1991).

Kotzbauer et al., "Neurturin, a relative of glial–cell–line–derived neurotrophic factor" *Nature* 384:467–470 (1996).

Lai et al., "An extended Family of Protein–Tyrosine Kinase Genes Differentially Expressed in the Vertebrate Nervous System" Neuron 6:691–704 (May 1991).

Lee et al., "Glycosyl–Phosphatidylinositol–anchored or integral membrane forms of CD14 mediate identical cellular responses to endotoxin" *Proc. Natl. Acad. Sci. USA* 90:9930–9934 (1993).

Leibrock et al., "Molecular cloning and Expression of Brain–derived Neurotrophic Factor" *Nature* 344:149–152 (Sep. 14, 1989).

Lin et al., "GDNF: A Glial Cell Line–Derived Neurotrophic Factor for Midbrain Dopaminergic Neurons" *Science* 260:1130–1132 (1993).

Lindsay and Yancopoulos, "GDNF in a Bind with Known Orphan: Accessory Implicated in New Twist" *Neuron* 17:571–574 (1996).

Maisonpierre et al., "Ehk–2; two novel members of the Eph receptor–like tyrosine kinase family with distinctive structures and neuronal expression" *Oncogene* 8:3277–3288 (1993).

Maisonpierre et al., "Neurotrophin–3: A Neurotrophic Factor Related to NGF and BDNF" *Science* 247:1446–1451 (Mar. 23, 1990).

Marcyniuk et al., "The Topography of Cell Loss From Locus Caeruleus in Alzheimer's Disease" *J. Neurol. Sci.* 76:335–345 (1986).

Micanovic et al., "Selectivity of the cleavage/attachment site of phosphatidylinositol–glycan–anchored membrane proteins determined by site–specific mutagenesis at Asp–484 of placental alkaline phosphatase" *Proc. Natl. Acad. Sci. USA* 87:157–161 (1990).

Moore et al., "Renal and neuronal abnormalities in mice lacking GDNF" *Nature* 382:76–79 (1996).

Moran et al., "Glycophospholipid membrane anchor attachment. Molecular analysis of the cleavage/attachment site" *Journal of Biological Chemistry* 266(2):1250–1257 (Jan. 15, 1991).

Oppenheim et al., "Developing motor neurons rescued from programmed and axotomy–induced cell death by GDNF" *Nature* 373:344–346 (1995).

Pasquale et al., "Identification of a Developmentally Regulated Protein–Tyrosine Kinase by using anti–phosphotyrosine Antibodies to Screen a cDNA Expression Library" *Proc. Natl. Acad. Sci. USA* 86:5449–5453 (1989).

Pasquale e.. Identification of chicken embryo kinase 5, a developmentally regulated receptor–type tyrosine kinase of the Eph family *Cell Regulation* 2:523–534.

Pichel et al., "Defects in enteric innervation and kidney development in mice lacking GDNF" *Nature* 382:73–76 (1996).

Poulsen et al., "TGFβ2 and TGFβ3 are potent survival factors for midbrain dopaminergic neurons" *Neuron* 13(5):1245–1252 (Nov. 1994).

Pugin et al.., "Lipopolysaccharide activation of humanendothelial cells is mediated by lipopolysaccharide–binding protein and soluble CD14" *Proc. Natl. Acad. Sci. USA* 90:2744–2748 (1993).

Rhee et al., "Studies of Inositol Phospholipid–Specific Phospholipase C" *Science* 244:546–550 (1989).

Rosenthal et al., "Primary Structure and Biological Activity of a Novel Human Neurotrophic Factor" *Neuron* 4:767–778 (1991).

Sajjadi et al., "Identification of a new eph–related receptor tyrosine kinase gene from mouse and chicken that is developmentally regulated and encodes at least two forms of the receptor" *New Biol.* 3(8):769–778 (1991).

Sanchez et al., "Renal agenesis and the absence of enteric neurons in mice lacking GDNF" *Nature* 382:70–73 (1996).

Sanicola et al., "Glial cell line–derived neurotrophic factor–dependent RET activation can be mediated by two different cell–surface accessory proteins" *Proc. Natl. Acad. Sci. USA* 94(12):6238–6243 (Jun. 10, 1997).

Shukla, S., "Phosphatidylinositol Specific Phospholipases C" *Life Sci.* 30:1323–1335 (1982).

Stahl et al., "The Alphas, Betas. and Kinases of Cytokine Receptor Complexes" *Cell* 74:587–590 (Aug. 27, 1993).

Stahl et al., "The Tripartite GNTF Receptor Complex: Activation and Signaling Involves Components Shared with Other Cytokines" *Journal of Neurobiology* 25(11):1454–1466 (1994).

Stromberg et al., "Glial Cell Line–Derived Neurotrophic Factor is Expressed in the Developing but Not Adult Striatum and Stimulates Developing Dopamine Neurons in Vivo" *Exp. Neurl.* 124:401–412 (1993).

Sun et al., "The Cystine–Knot Growth–Factor Superfamily" *Annual Review of Biophysics and Biomolecular Structure* 24:269–291 (1995).

Takahashi et al., "Identification of the ret proto–oncogene products in neuroblastoma and leukemia cells" *Oncogene* 6:297–301 (1991).

Thoenen et al., "Physiology of Nerve Growth Factor" *Physiological Reviews* 60(4): 1284–1335 (Oct. 1980).

Tomac et al., "Protection and repair of the nigrostriatal dopaminergic system by GDNF in Vivo" *Nature* 373:335–339 (1995).

Treanor et al., "Characterization of a multicomponent receptor for GDNF" *Nature* 381:785–789.

Trupp et al., "Functional receptor for GFNF encoded by the c–ret proto–oncogene" *Nature* 381:785–789.

Wrana et al., "Mechanism of activation of the TGF–β receptor" *Nature* 370:341–347 (1994).

Yan et al., "In vivo neurotrophic effects of GDNF on neonatal and adult facial motor neurons" *Nature* 373:341–344 (1995).

* cited by examiner

```
CCGAGAGCTG CGGGGGGAGG AGGAGGAGGG TGCCGACGCT TGAGTGGGTT CGAGCCCGAG CCGTAGCCGG GGGAGCCAGT CAGTTTCCGG CCAAGGCAGC      100
AGGGAGAAAG ACAAAAAAAC GGTGGGATTT ATTTAAC ATG ATC TTG GCA AAC GTC TTC CTC TTC TTT CTA GAC GAG                      182
                                        Met Ile Leu Ala Asn Val Phe Leu Phe Phe Leu Asp Glu
                                         1               5                  10              15

ACC CTC CGC TCT TTG GCC AGC CCT TCC TCC CTG CAG GAC CCC GAG CTC CAC GGC CTC CAC GAG CCC CCA GTG GAC TGT      257
Thr Leu Arg Ser Leu Ala Ser Pro Ser Ser Leu Gln Asp Pro Glu Leu His Gly Leu His Glu Pro Pro Val Asp Cys
            20                  25                  30                  35                  40

GTC CGG GCC AAT GAG CTG TGT GCC GCC GAA TCC AAC TGC AGC TCT CGC ACT CTG CGG CAG TGC CTG GCA      332
Val Arg Ala Asn Glu Leu Cys Ala Ala Glu Ser Asn Cys Ser Ser Arg Thr Leu Arg Gln Cys Leu Ala
        45                  50                  55                  60                  65

GGC CGC GAC CGC AAC ACC ATG CTG GCC AAC AAG GAG TGC CAG GCG TTG GAG GTC CAG CTG GAG AGC CCG CTG      407
Gly Arg Asp Arg Asn Thr Met Leu Ala Asn Lys Glu Cys Gln Ala Leu Glu Val Gln Leu Glu Ser Pro Leu
            70                  75                  80                  85                  90

TAC GAC TGC CGC AAG TGC CGC AAG CGG GGC ATG CGG GGC AAG GAG CTG CAG TGT CTG CAG ATC CAC CTG GGG      482
Tyr Asp Cys Arg Lys Cys Arg Lys Arg Gly Met Arg Gly Lys Glu Leu Gln Cys Leu Gln Ile His Leu Gly
        95                 100                 105                 110                 115

CTG ACG GAG GGT GAG GAG TTC TAC GAA GCC CCG TCC CCC TAT GAG TAT GAG GTG GTC ACC CCG GTG ACC TCC CGC CTC TCG GAC ATC TTC AGG      557
Leu Thr Glu Gly Glu Glu Phe Tyr Glu Ala Pro Ser Pro Tyr Glu Tyr Glu Val Val Thr Pro Val Thr Ser Arg Leu Ser Asp Ile Phe Arg
            120                 125                 130                 135                 140

CTT GCT TCA ATC TTC TCA GGG ACA GGG GCA GAC CCG GTG GTC AGC GCC AAG AGC AAC CAT TGC CTG GAT GCT GCC      632
Leu Ala Ser Ile Phe Ser Gly Thr Gly Ala Asp Pro Val Val Ser Ala Lys Ser Asn His Cys Leu Asp Ala Ala
            145                 150                 155                 160                 165

AAG GCC TGC AAC CTG AAT GAC AAC TGC AAG AAG CTG CGC TCC TAC ATC TCC ATC TGC AAC CGC GAG ATC TCG      707
Lys Ala Cys Asn Leu Asn Asp Asn Cys Lys Lys Leu Arg Ser Tyr Ile Ser Ile Cys Asn Arg Glu Ile Ser
        170                 175                 180                 185                 190

CCC ACC GAG CGC AAC TGC AAC CGC CGC AAG TGC CAC AAG GCC CTG CGC CAG TTC TTC GAC CGG GTG CCC AGC GAG TAC      782
Pro Thr Glu Arg Asn Cys Asn Arg Arg Lys Cys His Lys Ala Leu Arg Gln Phe Phe Asp Arg Val Pro Ser Glu Tyr
            195                 200                 205                 210                 215
```

FIG. 1A

```
ACC TAC CGC ATG CTC TTC TGC TCC TGC CAA GAC CAG GCG TGC GCT GAG CGC CGG CAA ACC ATC CTG CCC AGC   857
Thr Tyr Arg Met Leu Phe Cys Ser Cys Gln Asp Gln Ala Cys Ala Glu Arg Arg Gln Thr Ile Leu Pro Ser
    220                     225                     230                     235                 240

TGC TCC TAT GAG AAG GAC AAG GAG AAG CCC AAC TGC CTG GAC CTG CGT GGC GTG TGC CGG CAC CTG TGT CGG   932
Cys Ser Tyr Glu Lys Asp Lys Glu Lys Pro Asn Cys Leu Asp Leu Arg Gly Val Cys Arg His Leu Cys Arg
    245                     250                     255                     260                 265

TCC CGG GCC CTG GAC TTC CAT GCC AAT TGT CGA GCC TCC TAC CAG ACG GTC ACC AGC TGC CCT GCG GAC AAT TAC  1007
Ser Arg Ala Leu Asp Phe His Ala Asn Cys Arg Ala Ser Tyr Gln Thr Val Thr Ser Cys Pro Ala Asp Asn Tyr
    270                     275                     280                     285                 290

CAG GCG TGT CTG GGC TCT TAT GCT GGC ATG ATT GGG TTT GAC ATG ACA CCT AAC TAT GTG GAC TCC AGC CCC ACT  1082
Gln Ala Cys Leu Gly Ser Tyr Ala Gly Met Ile Gly Phe Asp Met Thr Pro Asn Tyr Val Asp Ser Ser Pro Thr
    295                     300                     305                     310                 315

GGC ATC GTG GTG TCC CCC TGG TGC AGC TGT CGT CGT CCC TGC AAC ATG GAG GAG AAG TGT GAG GAG GTG TGC TTC CTC AGG  1157
Gly Ile Val Val Ser Pro Trp Cys Ser Cys Arg Cys Asn Met Glu Glu Lys Cys Glu Glu Val Cys Phe Leu Arg
    320                     325                     330                     335                 340

GAC TTC ACC GAG AAC CCA TGC CTC CGG AAC GCC ATC CAG GCC TTT GGC AAC GGG GAC GTG TCC CCA  1232
Asp Phe Thr Glu Asn Pro Cys Leu Arg Asn Ala Ile Gln Ala Phe Gly Asn Gly Asp Val Ser Pro
    345                     350                     355                     360         365

AAA GGC CCC TCG TTC CAG GCC ACC CAG GCC CCT CGG GTG GAG AAG ACG CCT TCT TTG CCA GAT GAC CTC AGT GAC  1307
Lys Gly Pro Ser Phe Gln Ala Thr Gln Ala Pro Arg Val Glu Lys Thr Pro Ser Leu Pro Asp Asp Leu Ser Asp
    370                     375                     380                     385                 390

AGT ACC AGC TTG GGG ACC AGT GTC ATC ATC ACC TGC ACG TCT GTC CAG GAG CAG GGG CTG AAG CTG AAC AAC TCC  1382
Ser Thr Ser Leu Gly Thr Ser Val Ile Ile Thr Cys Thr Ser Val Gln Glu Gln Gly Leu Lys Leu Asn Asn Ser
    395                     400                     405                     410                 415

AAA GAG TTA AGC ATG TGC TTC ACA GAG CTC TTC ACA AAT ATC ATC CCA GGG AGT AAC AAG GTG ATC AAA CCT AAC  1457
Lys Glu Leu Ser Met Cys Phe Thr Glu Leu Phe Thr Asn Ile Ile Pro Gly Ser Asn Lys Val Ile Lys Pro Asn
    420                     425                     430                     435                 440
```

FIG. 1B

| | | | | | | | | | | |
|---|---|---|---|---|---|---|---|---|---|---|
| TCA | GGC | CCC | AGC | AGA | GCC | AGA | CCG | TCG | GCT | GCC |
| Ser | Gly | Pro | Ser | Arg | Ala | Arg | Pro | Ser | Ala | Ala |
| | | | | 445 | | | | | 450 | |

| | | | | | | | | |
|---|---|---|---|---|---|---|---|---|
| TTG | ACC | GTG | CTG | TCT | GTC | CTG | ATG | CTG |
| Leu | Thr | Val | Leu | Ser | Val | Leu | Met | Leu |
| | | | 455 | | | | | 460 |

| | | | |
|---|---|---|---|
| AAA | CTG | GCC | TTG T | 1530 |
| Lys | Leu | Ala | Leu |
| | | | 464 |

| | | | | | |
|---|---|---|---|---|---|
| AGGCTGTGGG | AACCGAGTCA | GAATATTTTT | GAAAGCTACG | CAGACAAGAA | AACACACACA |
| GACACACACA | CACCTTGCAA | | | | 1630 |
| AAAAAAAATT | GTTTTTCCCA | CCTTGTCGCT | GAACCTGTCT | CCTCCCAGGT | TTCTTCTCTG |
| GAGAAGTTTT | TGTAAACCAA | ACAGACAAGC | AGGCAGGCAG | | 1730 |
| CCTGAGAGCT | GGCCCAGGGG | TCCCCAGGGG | GGGGAAACTC | TGGTGCCGGG | AGCTCTAGAA |
| ATGCCCTTCA | CTTTCTCCTG | GTGTTTTTCT | | | 1830 |
| CTCTGGACCC | TTCTGAAGCA | GAGACCCGAC | AAGAGCCTGC | AGCGGAAGGG | ACTCTGGGCT |
| GTGCCTGAGG | CTGGCTGGGG | GCAGGACAAC | ACAGCTGCTT | | 1930 |
| CCCCAGGCTG | CCCACTCTGG | GGACCCGCTG | GGGGCTGGCA | GAGGGCATCG | GTCAGCCGGG |
| CAGCGGGGCT | GGCCATGAGG | GTCCACCTTC | AGCCCTTTGG | | 2030 |
| CTTCAAGGAT | GGAGATGGTT | TTGCCCTTCC | TCTCTGCCCT | CGGGTGGGTCT | TGGTGGGTCT |
| GCAGCTGGTG | TGGAACTTC | CCCACGGATG | GCGGTGGAGG | | 2130 |
| GGGTTCGCAC | CGTGCTGGGC | TCCCCCCTGAC | TGTAGCACGG | AGTGTTGGGG | CTGGGGGCCA |
| GCTCCAGGAG | GGCTTGAGAG | CTCAGCCTGC | CTGGGAGAGC | | 2230 |
| CCTTGTGGCG | AGGCATTAAA | ACTTGGGCAC | CAGCTTCTTT | CTCGGTGGCA | GAAATTTGA |
| AGTCAGAGAG | AAACGGTCCT | TTGTTGGCTT | CTTTGCTTTC | | 2330 |
| TCGTGGGTCC | TTTGGCAGGC | CTCCCTTTGG | GGAGAGGGAG | TTCCTAGACG | ACAGCCGGGT |
| GTGTGTCTGC | AGCACCGTGG | GCCCTCAAGC | TTTCCGCTG | | 2430 |
| TCTTCTCCCT | CCTCCTCCTT | TCCCCTCTCT | CTTTCCTCAT | TTTCCTTTTT | TACGTCAACT |
| GTATGTACAT | ACCGGGGCTC | CTCTCCTAAC | ATATATGTAT | | 2530 |
| ATACACATCC | ATATACATAT | ATTGTGTGGT | TTCCCTTTC | TTTCCTTTTT | TAAGCAACAA |
| AACTATGGGG | | | | | 2600 |

```
GCGGTGGCGG CCGCTCTAGA ACTAGTGGAT CCCCGGGCTG CAGGAATTCG AGCTCGAGCA AGGGTTAGCG GGAGAAGATT TTTTTTTTT     100
TGAATCTTTT TCTTCGTCTT GGTGCCAAAG AAGCGACTCT GGTCTCCCGT CCTAGAAGCT TGCTCCTATT CCGTCGGTGG ATTTCTTTCC    200
TATTCGCATT TATTCGTGACC CCCTCCCTCG CTGCTTCCTT CCAGCCCTTC ACTTTCAGAT CGCCTCGCCC AGTCCCCTCC TGGGAAGTGC   300
AGGGGAATTG GACCCACGGG GACTCACGCC TTCCCGGACG CGGCGAGACG GGGCTGGGCT GACCTTCAGGA CCAGGCTGTT GGCTTAGAAG  GCAGCCAGAC 400
ACATAGCTAC GTGTGTTTGA TTTCAGTGGC AAGGGGGGAC GTCGAGAGGC AGCCCACCGC CCCTTCCCCCC TCCAACCAGC AGTGAGAATC  500
CCAGGACTCG GGATCTTCAA CCGGCGGCCG CCCGGCGGGA TCTCCGCATT GGATTTGGGG GTCGTTATTG CTCGGCTGTT ATTATTATCG  TTATTTTATT 600
TTTATTTTT AAACCTAAGG GAGAAAGACA CATACACACA AAACTGTGGG ATTTATTTAA C                                   688

ATG ATC TTG GCA AAC GCC TTC TGC CTC TTC  766
                                                           Met Ile Leu Ala Asn Ala Phe Cys Leu Phe
                                                            1                   5                10

TTC TTT TTA GAC GAA ACC CTC CGC TCT TTG GCC AGC CCT TCC TCC CTG CAG GGC TCT GAG CTC CAC GGC TGG CGC   841
Phe Phe Leu Asp Glu Thr Leu Arg Ser Leu Ala Ser Pro Ser Ser Leu Gln Gly Ser Glu Leu His Gly Trp Arg
          15                  20                  25                  30                  35

CCC CAA GTG GAC GTG GTC CGG GCC AAT GAG CTG TGT GCG GCT GAA TCC AAC TGC AGC TCC AGG TAC CGC ACC CTT   916
Pro Gln Val Asp Val Val Arg Ala Asn Glu Leu Cys Ala Ala Glu Ser Asn Cys Ser Ser Arg Tyr Arg Thr Leu
    40                  45                  50                  55                  60

CGG CAG TGC CTG GCA GGC CGG GAT CGC AAT AAG GAG GCA GCC CTG GAG GTC TTG   991
Arg Gln Cys Leu Ala Gly Arg Asp Arg Asn Thr Met Leu Ala Asn Lys Glu Ala Ala Leu Glu Val Leu
65                  70                  75                  80                  85

CAG GAA AGC CCA TAT GAC TGC CGC AGG CGC ATG GGC AGG GGT ATG AAG AAG CTG CAG ATC TAC TGG   991
Gln Glu Ser Pro Tyr Asp Cys Arg Cys Lys Arg Met Gly Met Lys Lys Leu Gln Ile Tyr Trp
            90                  95                 100                 105                 110

AGC ATC CAT CTG GGG CTG ACA GAG GGT GAG GAG TTC TAT GAA GCT TCC CCC TAT GAG CCT GTG ACC TCG CGC CTC  1066
Ser Ile His Leu Gly Leu Thr Glu Gly Glu Glu Phe Tyr Glu Ala Ser Pro Tyr Glu Pro Val Thr Ser Arg Leu
            115                 120                 125                 130                 135
```

```
TCG GAC ATC TTC AGG CTC GCT TCA ATC TTC TCA GGG ACA GAC CCG GCG GTC AGT ACC AAA AGC AAC CAC   1141
Ser Asp Ile Phe Arg Leu Ala Ser Ile Phe Ser Gly Thr Asp Pro Ala Val Ser Thr Lys Ser Asn His
        140                         145                         150                 155                 160

TGC CTG GAT GCC GCC AAG GCC TGC AAC CTG AAT GAC AAC TGC AAG CTT CTT CGC TCT TAT ATC TCC ATC TGC   1216
Cys Leu Asp Ala Ala Lys Ala Cys Asn Leu Asn Asp Asn Cys Lys Leu Leu Arg Ser Tyr Ile Ser Ile Cys
        165                         170                         175                         180                 185

AAC CGT GAG ATC TCT CCC ACC GAA CGC TGC AAC CGC CGC AAG TGC CAC AAG GCT CTG CGC CAG TTC TTT GAC CGT   1291
Asn Arg Glu Ile Ser Pro Thr Glu Arg Cys Asn Arg Arg Lys Cys His Lys Ala Leu Arg Gln Phe Phe Asp Arg
        190                         195                         200                         205                         210

GTG CCC AGC GAG TAT ACC TAC CGC ATG CTC TTC TGC TCC TGT CAG GAC CAG GCA TGT GCT GAG CGT CGC CGG CAA   1366
Val Pro Ser Glu Tyr Thr Tyr Arg Met Leu Phe Cys Ser Cys Gln Asp Gln Ala Cys Ala Glu Arg Arg Arg Gln
        215                         220                         225                         230                         235

ACC ATC CTG CCC AGT TGC TCC TAT GAG GAG AAG CTG AAG CCC AAC TGC CTG GAC CTG TGT CGT ACA   1441
Thr Ile Leu Pro Ser Cys Ser Tyr Glu Glu Lys Leu Lys Pro Asn Cys Leu Asp Leu Cys Arg Thr
        240                         245                         250                         255                 260

GAC CAC CTG TGC CGG TCC CGA CTG GCA GAT TTC CAC GCC AAC TGT CGA GCC TCC ACA ATC ACC AGC TGT   1516
Asp His Leu Cys Arg Ser Arg Leu Ala Asp Phe His Ala Asn Cys Arg Ala Ser Tyr Arg Ile Thr Ser Cys
        265                         270                         275                         280                 285

CCT GCG GAC AAC TAC CAG GCA TGT CTG GGC TCC TAT GCT GGC ATG ATT GGG TTT GAT ACA CCC AAC TAT GTG   1591
Pro Ala Asp Asn Tyr Gln Ala Cys Leu Gly Ser Tyr Ala Gly Met Ile Gly Phe Asp Thr Pro Asn Tyr Val
        290                         295                         300                         305                 310
```

FIG. 2B

```
GAC TCC AAC CCC ACG GGC ATC GTG GTG TCT CCC TGG TGC AAT TGT CGT GGC AGT GGG AAC ATG GAA GAA GAG TGT        1666
Asp Ser Asn Pro Thr Gly Ile Val Val Ser Pro Trp Cys Asn Cys Arg Gly Ser Gly Asn Met Glu Glu Glu Cys
315                 320                 325                 330                 335

GAG AAG TTC CTC AGG GAC TTC ACG GAA AAC CCA AAT GCC CTC CGG AAT GCC ATT CAG GCC TTT GGT AAT GGC ACA GAT    1741
Glu Lys Phe Leu Arg Asp Phe Thr Glu Asn Pro Asn Ala Leu Arg Asn Ala Ile Gln Ala Phe Gly Asn Gly Thr Asp
        340                 345                 350                 355                 360

GTG AAC ATG TCT CCC AAA GGC CCC TCA CTC CCA GCT ACC CAG GCC CCT CGG GTG GAG AAG ACT CCT TCA CTG CCA        1816
Val Asn Met Ser Pro Lys Gly Pro Ser Leu Pro Ala Thr Gln Ala Pro Arg Val Glu Lys Thr Pro Ser Leu Pro
365                 370                 375                 380                 385

GAT GAC CTC AGT GAC AGC ACC AGC ACC CTG AGT GTC ATC ACC ACC TGC ACA TCT ATC CAG GAG CAA GGG CTG            1891
Asp Asp Leu Ser Asp Ser Thr Ser Thr Leu Ser Val Ile Thr Thr Cys Thr Ser Ile Gln Glu Gln Gly Leu
        390                 395                 400                 405                 410

AAG GCC AAC AAC TCC AAA GAG TTA AGC CTG CTG GAG ATG TGC TTC ACA GAG CTC ACG AAC ATC AGT CCA GGG AGT AAA AAG  1966
Lys Ala Asn Asn Ser Lys Glu Leu Ser Leu Leu Glu Met Cys Phe Thr Glu Leu Thr Asn Ile Ser Pro Gly Ser Lys Lys
415                 420                 425                 430                 435

GTG ATC AAA CTT AAC TCA GGC TCC AGC AGA GCC AGA CTG TCG GCT GCC TTG ACT GCC CTC CCA CTC CTG ATG CTG         2041
Val Ile Lys Leu Asn Ser Gly Ser Ser Arg Ala Arg Leu Ser Ala Ala Leu Thr Ala Leu Pro Leu Leu Met Leu
        440                 445                 450                 455                 460
```

FIG. 2C

```
ACC TTG GCC TTG T AGGCCT TTGGAACCCA GCACAAAAGT TCTTCAAGCA ACCCAGATAT GAACTCCCGC CTGACAAAAT GGAAACACAC GCATACACAC   2140
Thr Leu Ala Leu
        464

ATGCACACAC ACACAAACAC ACACACACAC ACACACACAC ACACACACAC ACACCCCTTG CAAAAACACT TTTTTCCTA  CATTGTCTCT   2240
GAACCTTTCT CCTCCCAAGT TTCTTCTCTG TCTAAACCAA ACAGACAAGC AGGCGGGCAG TCAGAAGCCT GCCCAGAGGT CCCCTGCAAG   2340
GGACACCCAG CACCAACGAG GGCTCAAGGC TCTTGAGAGA CTCTTTTCTC TTCACTGGTG GGACAAGATG AGACCCTGAT GTGGAAGGTA   2440
CTTTGCTGTG CCTGGTGTGG ACTGGGGAAA GGACAGTTGC AGCTGCCTAC TCTGGGGACC TGCCCAAGGG TTCACAGAGA GCAAGGAAGC   2540
AGGGCTGGCC ACAAGGACTT TGTCACCTCT TCCTCTTGGC GAAATGGTTT GCTGCCATCC CCAGCCATTA TGTGGCCTAG TGGGTTTAAG   2640
TCTGGAGTAG GAAGCCTTCA GGCAGCTTCA CCTGTAGTAT AGCTGGGGTT GGGAGCTGTT ACAGGAGGAA GCTTCTTTGG GGCATGAGCA   2740
AGCCTTGGTT GGGCACCAGC TCCAAGATGT ACCTTCCTCC TTTATGCCAG GAATCTTGAA GTCAAAGAGA AATGATCCTC TGTTGGCTCT TTTTTGTTTG   2840
TTTTTGAATT TTTTTGTGGG TCCATTTGGG AGTCTCTCT  CTCTTCTTGT TGGGGAGAAG GGCTGTTGAG TGGGGCTGGG GAGACCCTAG CTGTACATAC TGGGTCTCCT   2940
CTCTGGTGGG TTCCCAAGCT TGCCCCTTCT CCATATCCAT ATATCCTATG ATTTTACTCT CTGAGACATT CATGCACTGT CTGTACATAC TGGGTCTCCT   3040
TTCTCAACAT ATGTGTATAT CCATATCCAT ATTTTACTCT ATTTTACTCT TTCTTTCATT TTTTTTAAAG AAACAAAACT ATGGAAATAA TACCCTACAG   3140
ATGAGCGAAA ATGTATTATT GTAAAGTTTA TTTTTTTAA  TAATGTTGTC TATGATGGGA AGAAAGGTAC CAGGACCCCT GAGCCCTGGT CCAGTGGGC    3240
TGGTGGGGCT GTGGCCGGGG ACTCCCGATT GCATTCACTC TTAACCAAGC TCCAATAAAC GTACTAGGAA GCGAAAAAAA AAAAAAAAAA ACTCGAGGGG   3340
GGGCCCGGTA CCCAATTC                                                                                             3358
```

```
hNTNRα    1 MILANVFFLFFFLDETLRSLASPSSLQDPELHGWRPPVDCVRANELCAAESNCSSRYRTLR
rNTNRα    1 MILANAFCLFFFLDETLRSLASPSSLQGSELHGWRPQVDCVRANELCAAESNCSSRYRTLR
rGDNFRα   1 MFLAT---LYFAL--PLLDLLMSAEVSGGD-----RLDCVKASDQCLKEQSCSTKYRTLR hNTNRα   62 QCLAGRDRN-----TMLANKECQAALEVLQESPLYDCRCRKRGMKKELQCLQIYWSIHLGLT
rNTNRα   62 QCLAGRDRN-----TMLANKECQAALEVLQESPLYDCRCRKRGMKKELQCLQIYWSIHLGLT
rGDNFRα  51 QCVAGKETNFSLTSGLEAKDECRSAMEALKQKSLYNCRCKRGMKKEKNCLRIYWSMYQSLhNTNRα  118 EGEEFYEASPYEPVTSRLSDIFRLASIFSGTGADPVSAKSNHCLDAAKACNLNDNCKKLR
rNTNRα  118 EGEEFYEASPYEPVTSRLSDIFRLASIFSGTGTDPAVSTKSNHCLDAAKACNLNDNCKKLR
rGDNFRα 111 QGNDLLEDSPYEPVNSRLSDIFRAVPFISDVFQQVEHISKGNNCLDAAKACNLDDTCKKYR hNTNRα  179 SSYISICNREISPTERCNRRKCHKALRQFFDRVPSEYTYRMLFCSCQDQACAERRRQTILP
rNTNRα  179 SSYISICNREISPTERCNRRKCHKALRQFFDRVPSEYTYRMLFCSCQDQACAERRRQTILP
rGDNFRα 172 SAYITPCTTSMS-NEVCNRRKCHKALRQFFDKVPAKHSYGMLFCSCRDIACTERRRQTIVP
```

```
hGDNFRα    1  - - - - - - - - M F L A T L Y F A L P L L D L L S A E V S G - G D R L D C V K A S D Q C L K E
hNTNRα     1  M I L A N V F L F F F L D E T L R S L A S P S S L Q D P E L H G W R P P V D C V R A N E L C A A E hGDNFRα   40  Q S C S T K Y R T L R Q C V A G K E T N F S L A S G L E A K D E C R S A M E A L K Q K S L Y N C R C
hNTNRα    51  S N C S S R Y R T L R Q C L A G R D R N - - - - T M L A N K E C Q A A L E V L Q E S P L Y D C R C hGDNFRα   90  K R G M K K E K N C L R I Y W S M Y Q S L - Q G N D L L E D S P Y E P V N S R L S D I F R V V P F I
hNTNRα    96  K R G M K K E L Q C L Q - - I Y W S I H L G L T E G E E F Y E A S P Y E P V T S R L S D I F R L A S I F hGDNFRα  139  S D V F Q Q V E H I P K G N C L D A A K A C N L D D I C K K Y R S A Y I T P C T T S V S - N D V C
hNTNRα   146  S G T G A D P V V S A K S N H C L D A A K A C N L N D N C K K L R S S Y I S I C N R E I S P T E R C hGDNFRα  188  N R R K C H K A L R Q F F D K V P A K H S Y G M L F C S C R D I A C T E R R R Q T I V P V C S Y E E
hNTNRα   196  N R R K C H K A L R Q F F D R V P S E Y T Y R M L F C S C Q D Q A C A E R R R Q T I L P S C S Y E D
```

FIG. 5A

```
hGDNFRα  238  REKPNCLSLQDSCKTNYICRSRLADFFTNCQPESRSVSCLKENYADCLL
hNTNRα   246  KEKPNCLDLRGVCRTDHLCRSRLADFHANCRASYQTVTCPADNYQACLG hGDNFRα  288  AYSGLIGTVMTPNYIDSS--SLSVAPWCDCSNSGNDLEECLKFLNFFKDN
hNTNRα   296  SYAGMIGFDMTPNYVDSSPTGIVVSPWCSCRGSGNMEECEKFLRDFTEN hGDNFRα  336  TCLKNAIQAFGNGSDVTVWQPAPPVQTTTALRVKNKPLGPAGSEN-
hNTNRα   346  PCLRNAIQAFGNGTDVNVSPKGPSFQATQAPRVEKTPSLPDDLSDSTS-- hGDNFRα  386  EIPTHVLPPCANLQAQKLKSNVSGNTHLCISNGNYEKEGLGASSHITTKS
hNTNRα   394  -LGTSVITTCTSVQEQGLKANNSKELSMCFT--ELTTNIIPGSNKVIKPN hGDNFRα  436  MAAPPSCGLSPLLVLVVTALSTLLSLTETS
hNTNRα   441  SGPSRARPSAALTVLSVLMLKLAL
```

FIG. 5B

○ mNTN    ● rGDNF

NEURTURIN RECEPTOR

The present application is a division of application Ser. No. 08/802,805 filed on Feb. 18, 1997, which is a continuation of application Ser. No. 08/957,063 filed on Oct. 24, 1997, now U.S. Pat. No. 6,025,157, which claims benefit of the priority of provisional applications Ser. Nos. 60/038,839 filed on Feb. 18, 1997, and 60/049,818 filed on Jun. 9, 1997, both abandoned.

TECHNICAL FIELD

The present invention relates to a Neurturin ("NTN") receptor designated NTNRα, and provides for NTNRα-encoding nucleic acid and amino acid sequences. In particular, the invention relates to native sequence NTNRα, NTNRα variants, soluble NTNRα variants including NTNRα extracellular domain, chimeric NTNRα, and antibodies which bind to the NTNRα (including agonist and neutralizing antibodies), as well as various uses for these molecules. It also relates to assay systems for detecting ligands to NTNRα, systems for studying the physiological role of NTN, diagnostic techniques for identifying NTN-related conditions, therapeutic techniques for the treatment of NTN-related and NTNRα-related conditions, and methods for identifying molecules homologous to NTNRα.

BACKGROUND

Neurotrophic factors such as insulin-like growth factors, nerve growth factor, brain-derived neurotrophic factor, neurotrophin-3, -4/5 and -6, ciliary neurotrophic factor, GDNF, and neurturin have been proposed as potential means for enhancing specific neuronal cell survival, for example, as a treatment for neurodegenerative diseases such as amyotrophic lateral sclerosis, Alzheimer's disease, stroke, epilepsy, Huntington's disease, Parkinson's disease, and peripheral neuropathy. It would be desirable to provide additional therapy for this purpose. Protein neurotrophic factors, or neurotrophins, which influence growth and development of the vertebrate nervous system, are believed to play an important role in promoting the differentiation, survival, and function of diverse groups of neurons in the brain and periphery. Neurotrophic factors are believed to have important signaling functions in neural tissues, based in part upon the precedent established with nerve growth factor (NGF). NGF supports the survival of sympathetic, sensory, and basal forebrain neurons both in vitro and in vivo. Administration of exogenous NGF rescues neurons from cell death during development. Conversely, removal or sequestration of endogenous NGF by administration of anti-NGF antibodies promotes such cell death (Heumann, *J. Exp. Biol.,* 132:133–150 (1987); Hefti, *J. Neurosci.,* 6:2155–2162 (1986); Thoenen et al., *Annu. Rev. Physiol.,* 60:286–335 (1980)).

Additional neurotrophic factors related to NGF have since been identified. These include brain-derived neurotrophic factor (BDNF) (Leibrock, et al., *Nature,* 341:149–152 (1989)), neurotrophin-3 (NT-3) (Kaisho, et al., *FEBS Lett.,* 266:187 (1990); Maisonpierre, et al., *Science,* 247:1446 (1990); Rosenthal, et al., *Neuron,* 4:767 (1990)), and neurotrophin 4/5 (NT-4/5) (Berkmeier, et al., *Neuron,* 7:857–866 (1991)).

Neurotrophins, similar to other polypeptide growth factors, affect their target cells through interactions with cell surface receptors. According to current understanding, two kinds of transmembrane glycoproteins act as receptors for the known neurotrophins. Equilibrium binding studies have shown that neurotrophin-responsive neuronal cells possess a common low molecular weight (65,000–80,000 Daltons), a low affinity receptor typically referred to as $p75^{LNGFR}$ or p75, and a high molecular weight (130,000–150,000 Dalton) receptor. The high affinity receptors are members of the trk family of receptor tyrosine kinases.

Receptor tyrosine kinases are known to serve as receptors for a variety of protein factors that promote cellular proliferation, differentiation, and survival. In addition to the trk receptors, examples of other receptor tyrosine kinases include the receptors for epidermal growth factor (EGF), fibroblast growth factor (FGF), and platelet-derived growth factor (PDGF). Typically, these receptors span the cell membrane, with one portion of the receptor being intracellular and in contact with the cytoplasm, and another portion of the receptor being extracellular. Binding of a ligand to the extracellular portion of the receptor induces tyrosine kinase activity in the intracellular portion of the receptor, with ensuing phosphorylation of various intracellular proteins involved in cellular signaling pathways.

Glial cell line-derived neurotrophic factor ("GDNF") and Neurturin ("NTN") are two, recently identified, structurally related, potent survival factors for sympathetic sensory and central nervous system neurons (Lin et al. *Science* 260:1130–1132 (1993); Henderson et al. *Science* 266:1062–1064 (1994); Buj-Bello et al., *Neuron* 15:821–828 (1995); Kotzbauer et al. *Nature* 384:467–470 (1996)). Recently, GDNF was shown to mediate its actions through a multi-component receptor system composed of a ligand binding glycosyl-phosphatidyl inositol (GPI) linked protein (designated GDNFRα; also designated GFR-alpha-1) and the transmembrane receptor tyrosine kinase Ret (Treanor et al. *Nature* 382:80–83 (1996); Jing et al. *Cell* 85:1113–1124 (1996); Trupp et al. *Nature* 381:785–789 (1996); Durbec et al. *Nature* 381:789–793 (1996)). The mechanism by which the NTN signal is transmitted has not been elucidated.

Aberrant expression of receptor tyrosine kinases ("RTK") correlates with transforming ability. For example, carcinomas of the liver, lung, breast and colon show elevated expression of Eph RTK. Unlike many other tyrosine kinases, this elevated expression can occur in the absence of gene amplification or rearrangement. Moreover, Hek, a human RTK, has been identified as a leukemia-specific marker present on the surface of a pre-B cell leukemia cell line. As with Eph, Hek also was overexpressed in the absence of gene amplification or rearrangements in, for example, hemopoietic tumors and lymphoid tumor cell lines. Overexpression of Myk-1 (a murine homolog of human Htk (Bennett et al., *J. Biol. Chem.,* 269(19):14211–8 (1994)) was found in the undifferentiated and invasive mammnary tumors of transgenic mice expressing the Ha-ras oncogene. (Andres et al., *Oncogene,* 9(5):1461–7 (1994) and Andres et al., *Oncogene,* 9(8):2431 (1994)). Ret, the product of the c-ret proto-oncogene, is a member of the receptor tyrosine kinase superfamily.

In addition to their roles in carcinogenesis, a number of transmembrane tyrosine kinases have been reported to play key roles during development. Some receptor tyrosine kinases are developmentally regulated and predominantly expressed in embryonic tissues. Examples include Cek1, which belongs to the FGF subclass, and the Cek4 and Cek5 tyrosine kinases (Pasquale et al., *Proc. Natl. Acad Sci., USA,* 86:5449–5453 (1989); Sajjadi et al., *New Biol.,* 3(8):769–78 (1991); and Pasquale, *Cell Regulation,* 2:523–534(1991)). Eph family members are expressed in many different adult tissues, with several family members expressed in the nervous system or specifically in neurons (Maisonpierre et al., *Oncogene,* 8:3277–3288 (1993); Lai et al., *Neuron,* 6:691–704 (1991)).

The aberrant expression or uncontrolled regulation of any one of these receptor tyrosine kinases can result in different malignancies and pathological disorders. Therefore, there exists a need to identify means to regulate, control and manipulate receptor tyrosine kinases ("RTK") and their associated ligands or GPI-linked receptors, in order to provide new and additional means for the diagnosis and therapy of receptor tyrosine kinase pathway-related disorders and cellular processes. The present application provides the clinician and researcher with such means by providing new molecules that are specific for interacting with certain RTK receptors. These compounds and their methods of use, as provided herein, allow exquisite therapeutic control and specificity. Accordingly, it is an object of the present invention to provide an improved therapy for the prevention and/or treatment of neurological conditions and other conditions in which certain neurotrophic signaling pathways play a role.

These and other objects of the invention will be apparent to the ordinarily skilled artisan upon consideration of the specification as a whole.

SUMMARY

A NTN receptor termed NTNRα, a soluble form of the receptor, and a NTNRα extracellular domain ("ECD") are disclosed herein. Also disclosed are NTNRα polypeptides, optionally conjugated with or fused to molecules which increase the serum half-lives thereof, and optionally formulated as pharmaceutical compositions with a physiologically acceptable carrier.

Soluble NTNRα, including chimeric NTNRα molecules such as NTNRα ECD immunoadhesins (having long serum half-lives) and epitope-tagged NTNRα ECD, that retain both ligand binding, preferably NTN binding, and receptor signaling function (via Ret receptor tyrosine kinase) can be used to impart, restore, or enhance NTNRα-ligand (preferably NTN) responsiveness to cells. This responsiveness includes ligand-binding, Ret tyrosine phosphorylation and Ret-mediated downstream activity, which can result in modulation of cell activity such as survival or growth. The embodiments find use in vivo, in vitro or ex vivo. Soluble NTNRα forms that bind NTN but fail to interact with and activate Ret can be used as an antagonist to NTN ligand (by binding and sequestering NTN) to reduce activation of endogenous NTNRα. This is useful in conditions characterized by excess levels of NTN ligand and/or excess NTNRα activation in a mammal. Bispecific immunoadhesins (for example, combining a NTNRα-ligand binding activity with a ligand-binding domain of another cytokine or neurotrophic factor receptor) can form high affinity binding complexes for NTNRα-ligands and another factors, providing either antagonist activity (when Ret-activating function is absent) or a means to enhance the attached ligands delivery.

Pharmaceutical compositions of soluble NTNRα, preferably ECD, can optionally further include an NTNRα ligand, preferably NTN. Such compositions are useful where it is desirable to prolong the half-life of the ligand, provide slow, sustained release of ligand, impart NTNRα-ligand responsiveness to a target cell, and/or activate or enhance endogenous cellular NTNRα or Ret activity directly. Optionally, the composition further contains one or more cytokines, neurotrophic factors, or their agonist antibodies.

Also provided are methods for identifying a molecule which binds to and/or activates NTNRα. Thus assays are provided to screen for or identify NTNRα-ligand molecules (such as peptides, antibodies, and small molecules) that are agonists or antagonists of NTNRα. Such methods generally involve exposing an immobilized NTNRα to a molecule suspected of binding thereto and determining binding of the molecule to the immobilized NTNRα and/or evaluating whether or not the molecule activates (or blocks activation of) the NTNRα. In order to identify such NTN ligands, the NTNRα can be expressed on the surface of a cell and used to screen libraries of synthetic candidate compounds or naturally-occurring compounds (e.g., from endogenous sources such as serum or cells). NTNRα can also be used as a diagnostic tool for measuring serum levels of endogenous or exogenous NTNRα-ligand.

In a further embodiment, a method for purifying an NTNRα-ligand is provided. This finds use in commercial production and purification of therapeutically active molecules that bind to this receptor. In one embodiment the molecule of interest (generally in a composition comprising one or more contaminants) is adsorbed to immobilized NTNRα (e.g., NTNRα immunoadhesin immobilized on a protein A resin). The contaminants, by virtue of their inability to bind to the NTNRα, will generally not bind the resin. Accordingly, it is then possible to recover the molecule of interest from the resin by changing the elution conditions, such that the ligand molecule is released from the immobilized receptor.

Antibodies are provided that specifically bind to NTNRα. Preferred antibodies are monoclonal antibodies that are non-immunogenic in a human and bind to an epitope in the extracellular domain of the receptor. Preferred antibodies bind the NTNRα with an affinity of at least about $10^6$ L/mole, more preferably $10^7$ L/mole. Preferred antibodies are agonist antibodies.

Antibodies, which bind to NTNRα, can be optionally fused to a heterologous polypeptide. The antibody or fusion finds particular use to isolate and purify NTNRα from a source of the receptor.

In a further aspect is provided a method for detecting NTNRα in vitro or in vivo which includes the steps of contacting an NTNRα antibody with a sample suspected of containing the receptor, and detecting if binding has occurred.

For certain applications it is desirable to have an agonist antibody. Such agonist antibodies are useful for activating NTNRα as described for NTNRα-ligands such as NTN. Furthermore, these antibodies are useful to treat conditions in which an effective amount of NTNRα activation leads to a therapeutic benefit in the mammal. For example, the agonist antibody can be used to elicit an NTN response in a cell comprising NTNRα and, preferably, Ret. For therapeutic applications it is desirable to prepare a composition having the agonist antibody and a physiologically acceptable carrier. Optionally, the composition further contains one or more cytokines, neurotrophic factors, or their agonist antibodies.

In other embodiments, the antibody is a neutralizing antibody. Such molecules can be used to treat conditions characterized by unwanted or excessive activation of NTNRα.

In addition to the above, the invention provides isolated nucleic acid molecules, expression vectors and host cells encoding NTNRα which can be used in the recombinant production of NTNRα as described herein. The isolated nucleic acid molecules and vectors are also useful to prepare transgenic animals, for gene therapy applications to treat patients with NTNRα defects or increase responsiveness of cells to NTNRα ligands, or alternatively to decrease NTNRα activity (as by use of antisense nucleic acid).

BRIEF DESCRIPTION OF THE DRAWINGS

FIGS. 1A–1C depict the nucleic acid sequence (SEQ ID NO.: 1) of the sense strand of the cDNA encoding full length human NTNRα, the hNTNRα-encoding sequence (SEQ ID NO.: 2), and the deduced amino acid sequence of full length hNTNRα (SEQ ID NO.: 3). Nucleotides are numbered at the beginning of the sense strand. Amino acid residues are numbered at the begining of the amino acid sequence.

FIGS. 2A–2D depict the nucleic acid sequence (SEQ ID NO.: 4) of the sense strand of the cDNA encoding full length rat NTNRα, the rNTNRα-encoding sequence (SEQ ID NO.: 5), and the deduced amino acid sequence of full length rNTNRα(SEQ ID NO.: 6). Nucleotides are numbered at the beginning of the sense strand. Amino acid residues are numbered at the beginning of the amino acid sequence.

Figure 3A:
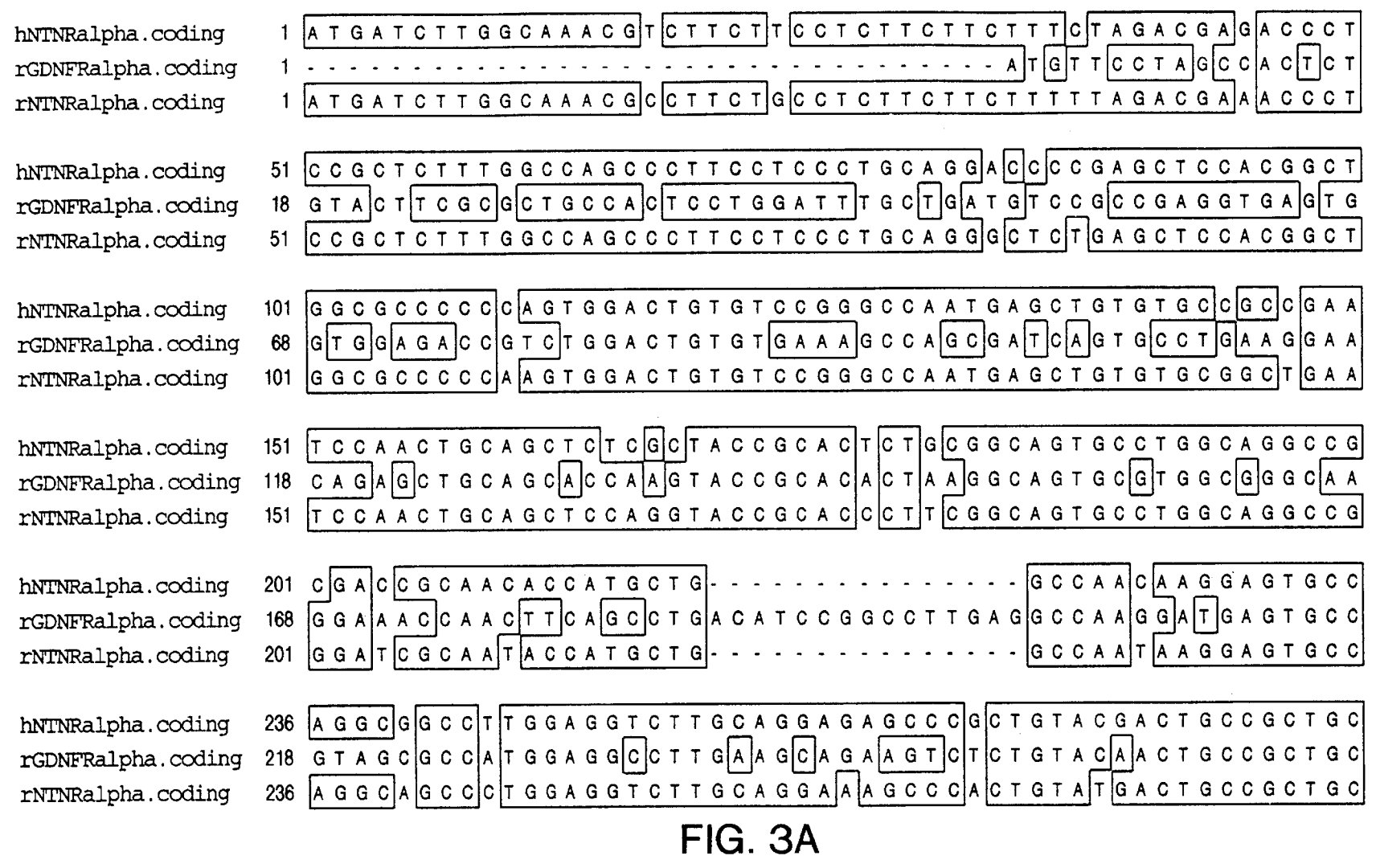
Figure 3B:
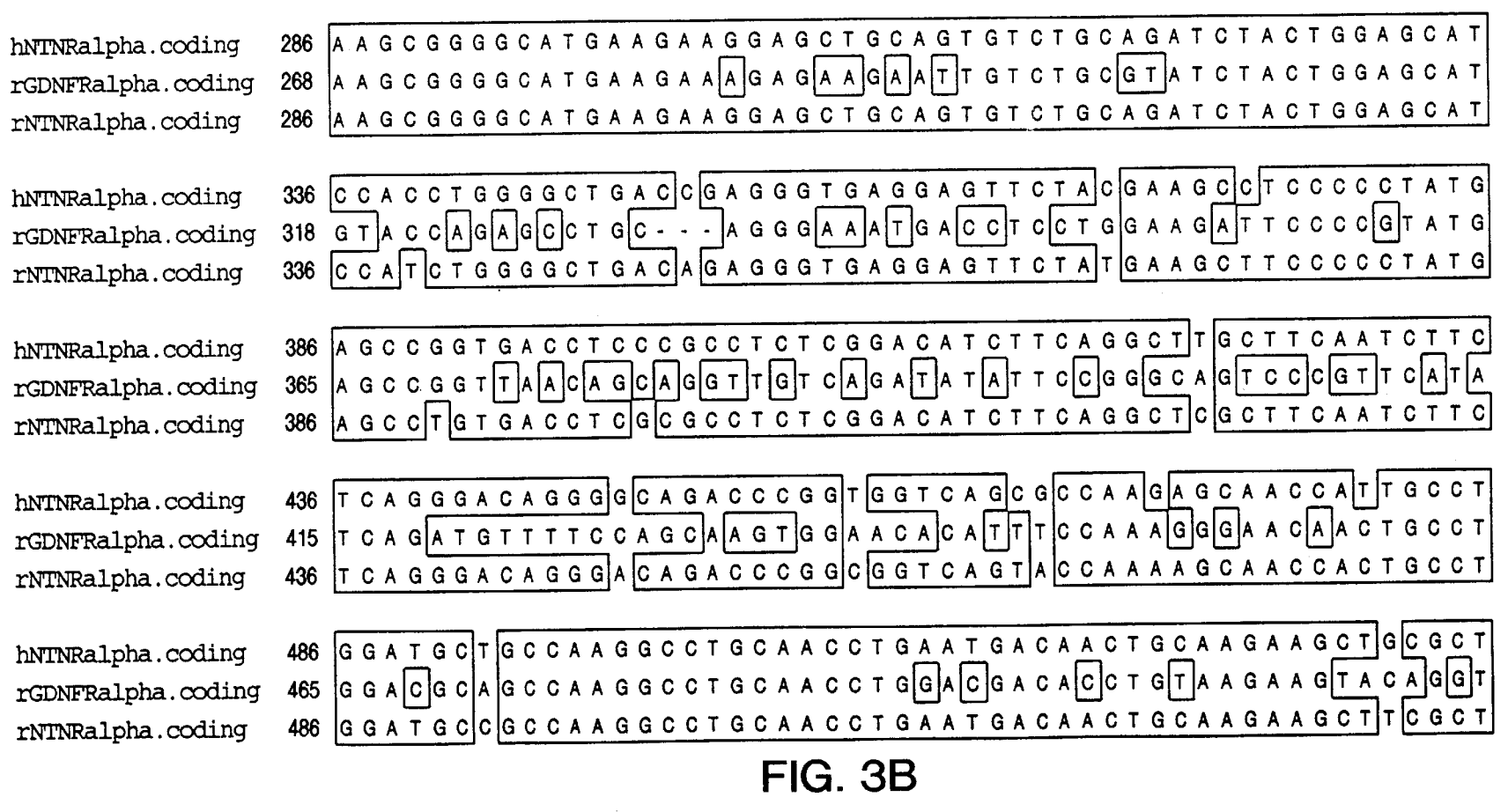
Figure 3C:
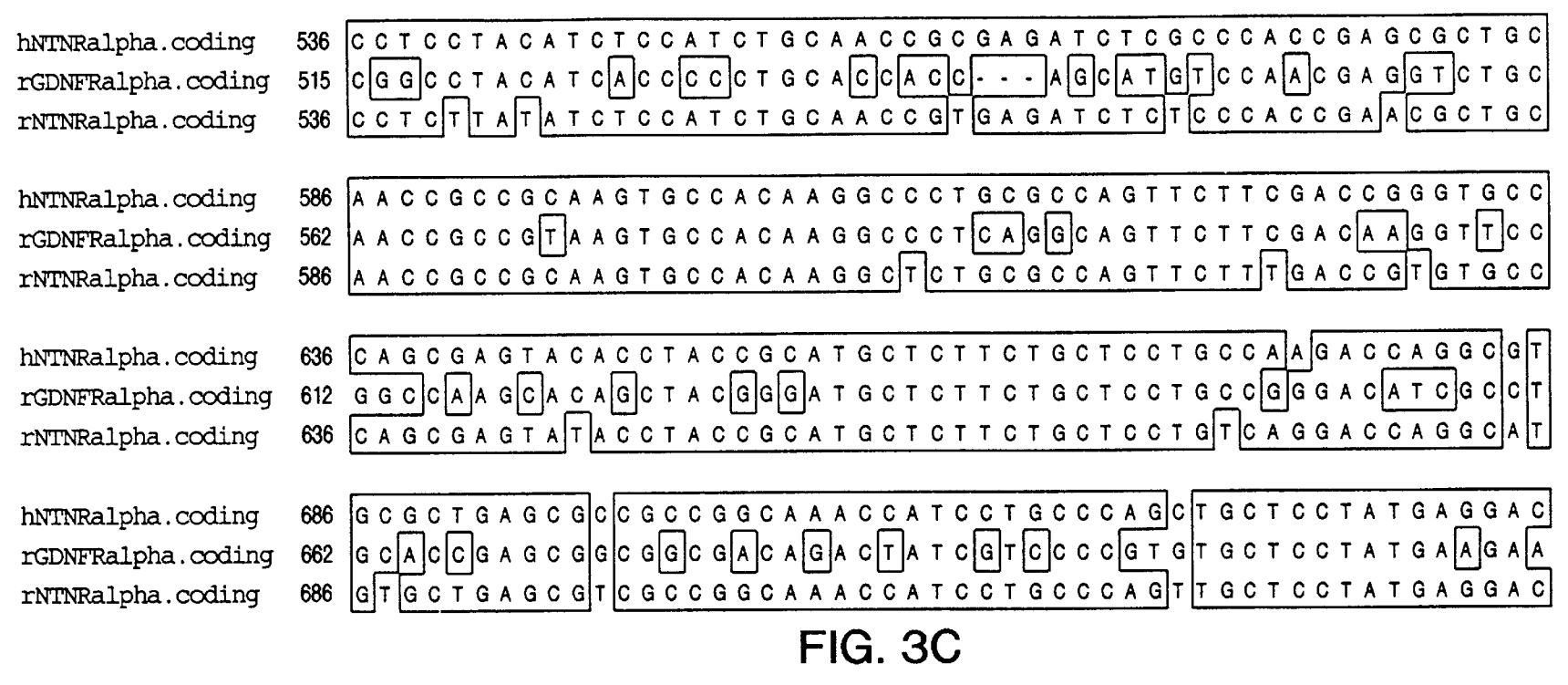
Figure 3D:
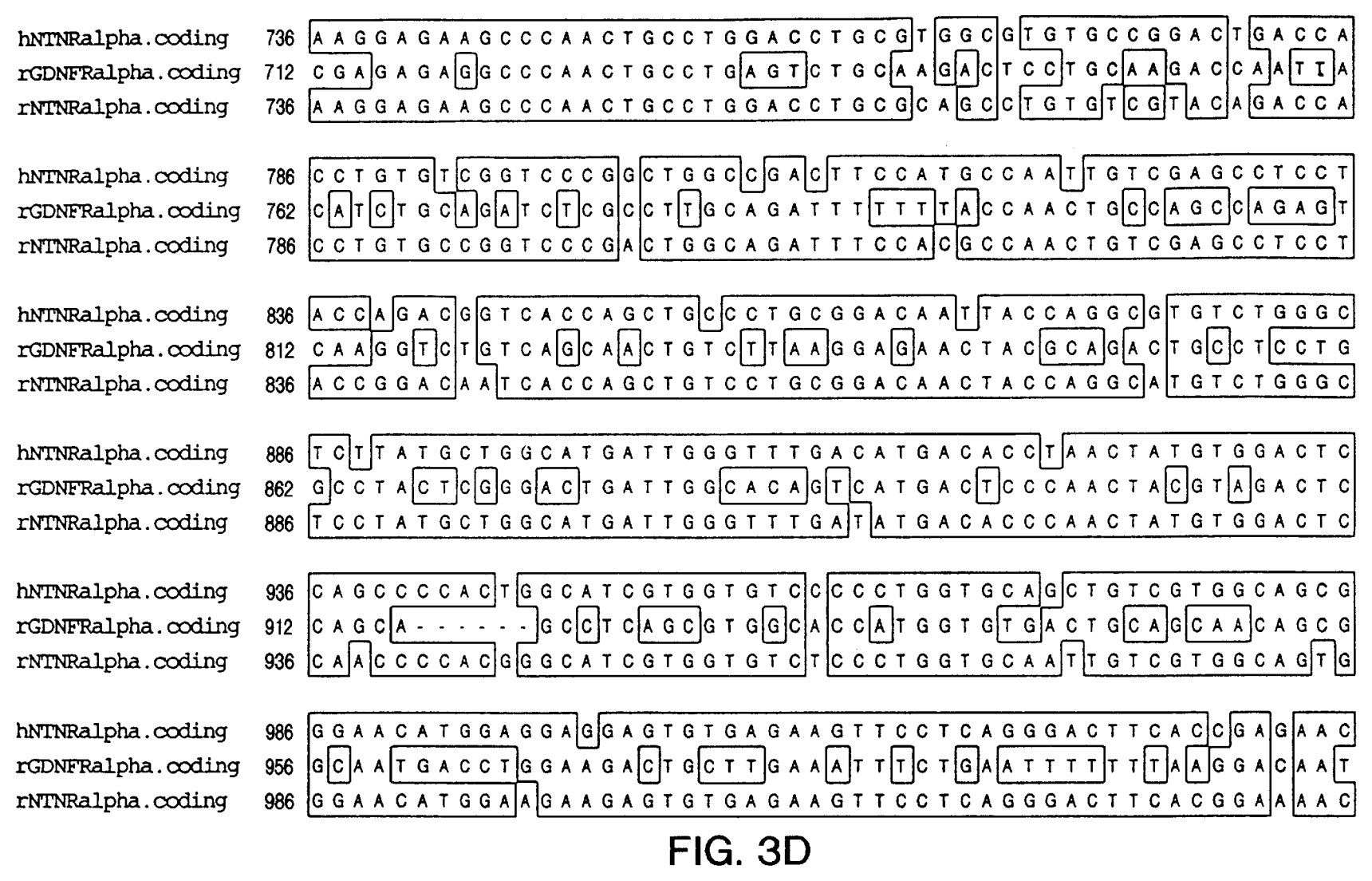
Figure 3E:
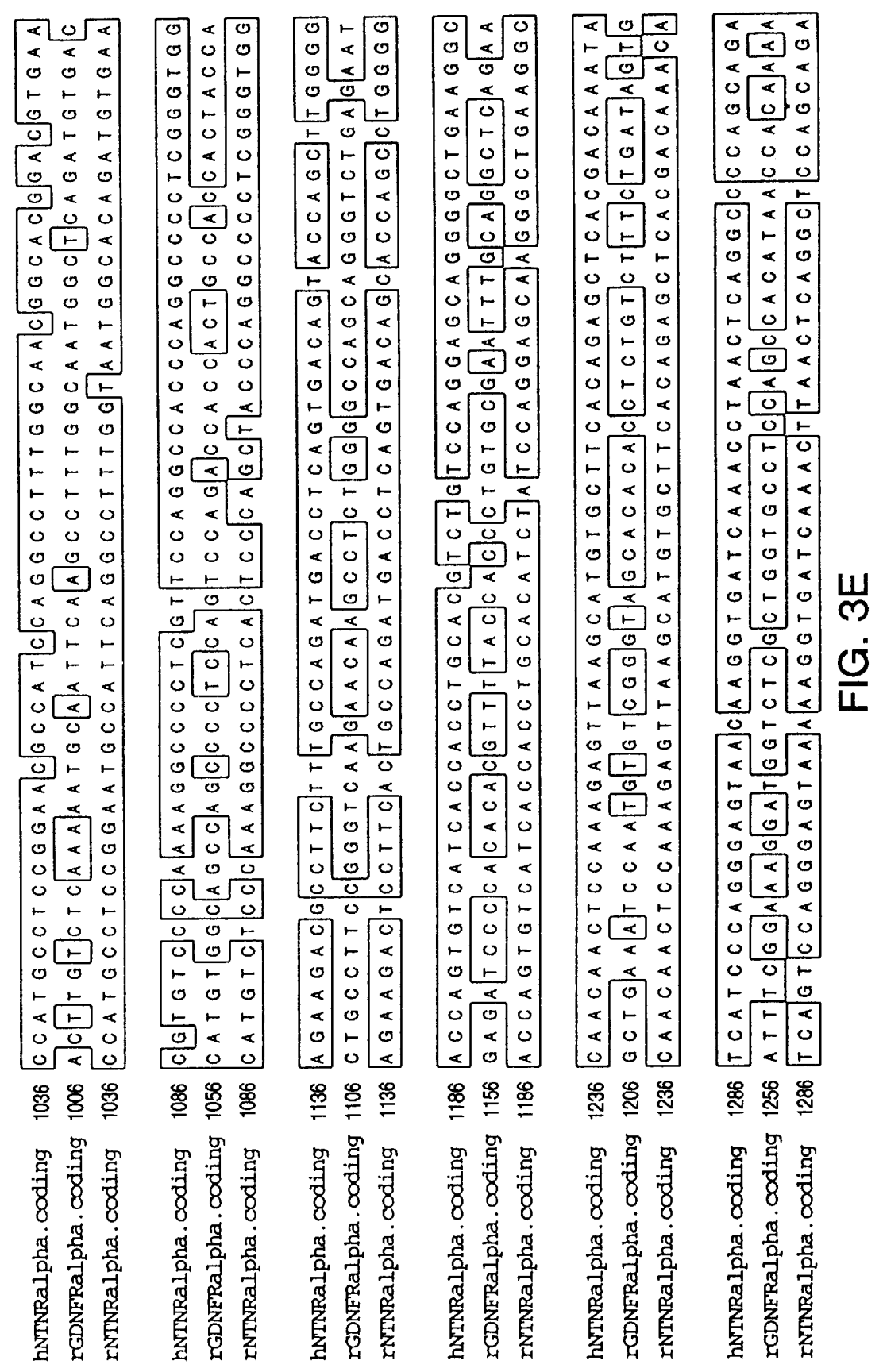
Figure 3F:
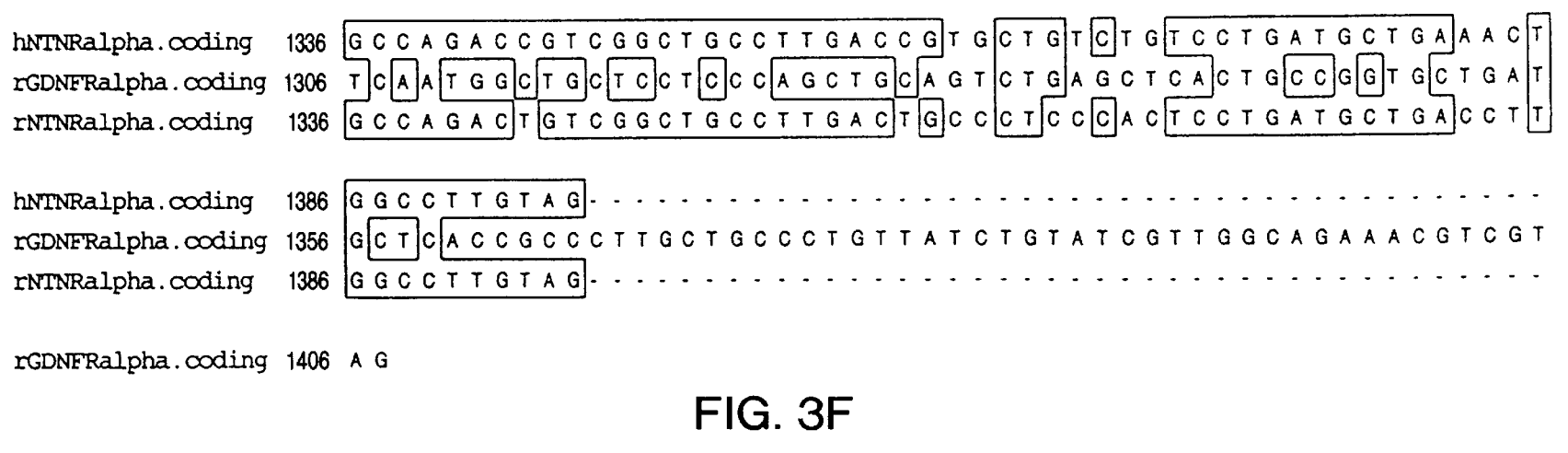

FIGS. 3A–3F compare hNTNRα-, rNTNRα-, and rGDNFRα-encoding nucleic acids.

Figure 4B:
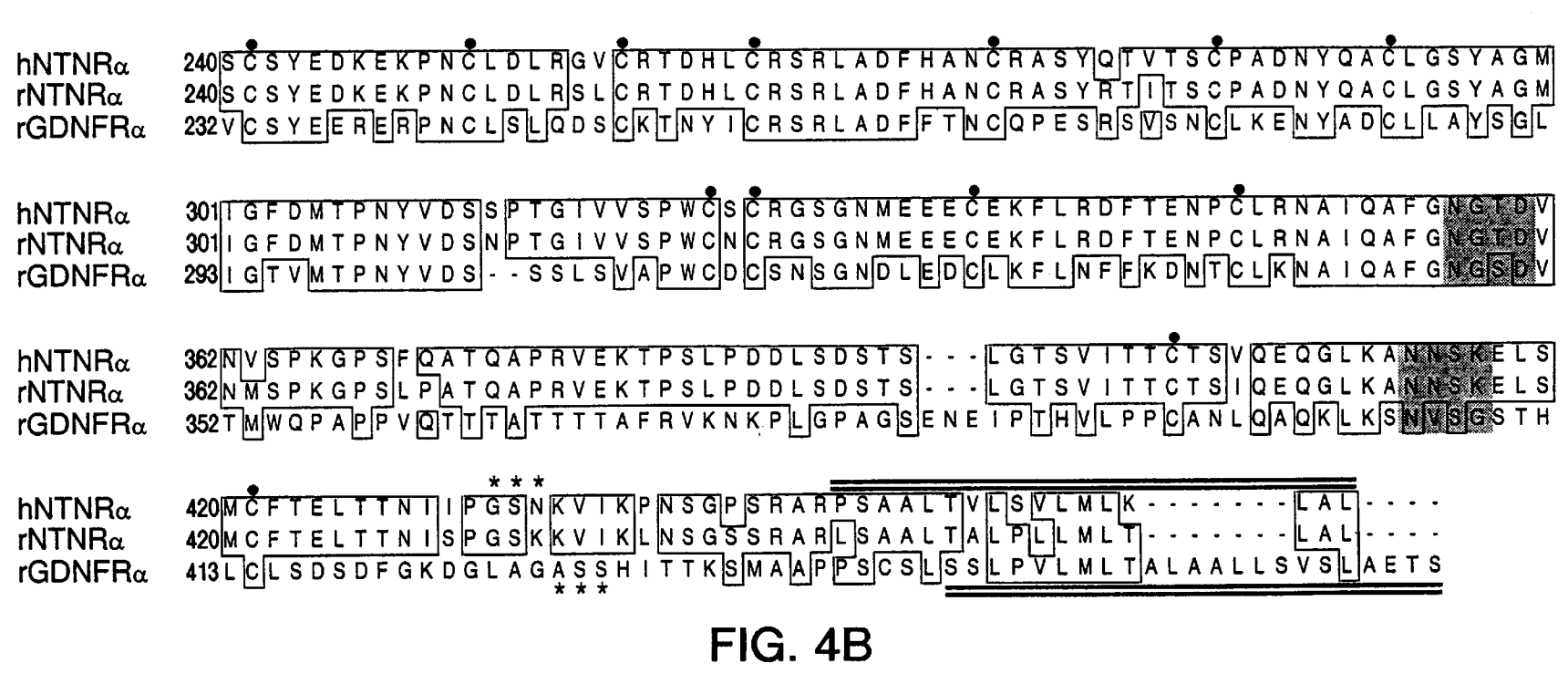

FIGS. 4A and 4B are a comparison of the hNTNRα, rNTNRα, and rGDNFRα proteins, with features indicated. Signal peptides are indicated by a solid line. Signal cleavage sites are marked with arrows. Potential glycosylation sites are shaded. The hydrophobic domain of the GPI attachment site is doubly underlined. The small amino acid residues that constitute a cleavage/attachment site for GPI-linked proteins marked with asterisks. Consensus cysteine residues are indicated by a solid circle. The extracellular domain ("ECD") is flanked by the signal peptide and the GPI-attachment site.

FIGS. 5A and 5B are a comparison of the amino acid sequences of hNTNRα and hGDNFRα.

FIGS. 6A and 6C show the binding of $^{125}I$ mouse NTN ($^{124}I$-mNTN) to rat GDNFRα ("rGDNFRα") or rat NTNRα ("rNTNRα"), respectively. FIGS. 6B and 6D show the bindings of $^{125}I$rGDNF ($^{125}I$-rGDNF) to rat GDNFRα ("rGDNFRα") or rat NTNRα ("rNTNRα"), respectively. As depicted by the Scatchard analysis, displayed in FIG. 6E, GDNF binds GDNFRα with a $K_d$ value of 3 pM. A similar $K_d$ was reported in a cell based assay (Jing et al. Cell 85:1113-1124 (1996)). Mouse NTN binds rNTNRα with a $K_d$ value of 10 pM (see FIG. 6F). Human NTNRα displayed a similar binding specificity as rat NTNRα (data not shown). Although in these experiments no binding of $^{125}I$ NTN to GDNFRα(FIG. 6A) and of $^{125}I$rGDNF to NTNRα (FIG. 6D) were detected, experiments performed with biotinylated NTN and GDNF revealed low affinity binding ($K_d$ above 1mM) of NTN to GDNFRα, and vice versa.

FIG. 7A depicts binding of $^{1252}I$ NTN to cells expressing NTNRα. Consistent with the prediction that NTNRα is a GPI-linked protein, binding of $^{125}I$ NTN to NTNRα expressing cells was reduced by 50–70% following treatment with PIPLC. FIG. 7B depicts survival response of embryonic, rat spinal motoneurons to GDNF or NTN. In agreement with its receptor distribution, NTN is a potent survival factor for spinal motoneurons. FIG. 7C depicts survival response of embryonic, rat spinal motoneurons to NTN or BDNF in the presence of PIPLC and a soluble NTNRα. PIPLC treatment reduced the survival response to NTN by 50–90% without changing the response to BDNF. Soluble NTNRα (sRα) restores the response of PIPLC-treated motoneurons to NTN. FIG. 7D depicts NTN induction of tyrosine phosphorylation of Ret in neuroblastoma TGW-1 cells. FIG. 7E depicts NTN induction of phosphorylation of ERK in TGW-1. FIG. 7F depict the NTN-responsiveness (e.g., Ret phosphorylation) imparted by an NTN-soluble NTNRα complex to Ret-expressing cells. Legends: (Con)=untransfected cells. (Ret)=cells transfected with Ret alone. (Rα+Ret)=cells transfected with Ret and NTNRα. In all cases, cells were exposed to NTN (100 ng/ml) and then processed for immunoprecipitation with NTN antisera.

DETAILED DESCRIPTION

Figure 6A:
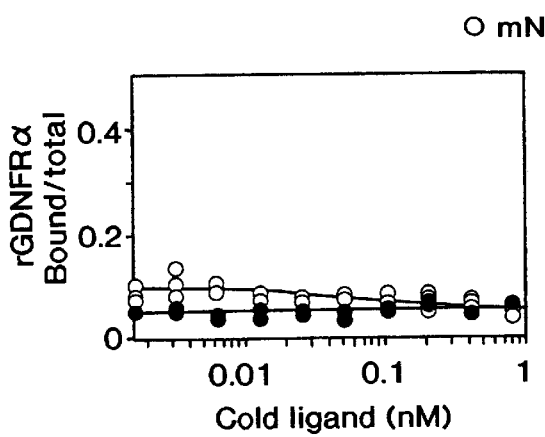
FIGS. 6A–6F depict binding of $I^{125}$ NTN and GDNF to NTNRα- or GDNFRα- expressing cells and displacement of unlabeled NTN.

In describing the present invention, the following terms will be employed and are intended to be defined as indicated below.

The terms "NTNRα" (also designated GFR-alpha-2) or "NTNRα polypeptide" when used herein encompass native sequence NTNRα; NTNRα variants; NTNRα extracellular domain; and chimeric NTNRα (each of which is defined herein). Optionally, the NTNRα is not associated with native glycosylation. "Native glycosylation" refers to the carbohydrate moieties which are covalently attached to NTNRα when it is produced in the mammalian cell from which it is derived in nature. Accordingly, human NTNRα produced int a non-human cell is an example of a NTNRα which may "not be associated with native glycosylation." Sometimes, the NTNRα is unglycosylated (e.g., as a result of being produced recombinantly in a prokaryote).

A "native sequence NTNRα" comprises a polypeptide having the same amino acid sequence as a NTNRα derived from nature. Thus, a native sequence NTNRα can have the amino acid sequence of naturally occurring rat NTNRα, murine NTNRα, human NTNRα, or NTNRα from any other mammalian species. Such native sequence NTNRα polypeptides can be isolated from nature or can be produced by recombinant or synthetic means. The term "native sequence NTNRα" specifically encompasses naturally-occurring truncated forms of the NTNRα, naturally-occurring variant forms (e.g., alternatively spliced forms), and naturally-occurring allelic variants of the NTNRα. The preferred native sequence NTNRα is a mature native sequence NTNRα. NTNRα sequence for human and rat are shown in FIGS. 1A–1C and 2A–2D. Preferred molecules are those comprising a nucleic acid molecule that is capable of hybridizing under moderate, and more preferably under stringent hybridization conditions, with the DNA sequence encoding the human NTN receptor shown in FIGS. 1A–1C. In one embodiment the NTNRα nucleic acid hybridizes at 42° C. in 20% formamide with the DNA sequence encoding the NTN receptor shown in FIGS. 1A–1C. In another embodiment a nucleic acid molecule is capable of hybridizing at 42° C. in 20% formamide with a DNA sequence of at least 10 contiguous bases, and preferably at least 20 contiguous bases, more preferably with at least 45 bases, and even more preferably with at least 60 bases encoding a portion of the complete NTN receptor shown in FIGS. 1A–1C or 2A–2D. Preferred sequences do not hybridize GDNFRα sequences under similar conditions.

The "NTNRα extracellular domain" (ECD) is a form of the NTNRα which is essentially free of the transmembrane and cytoplasmic domains of NTNRα, ie., has less than 1% of such domains, preferably 0.5% to 0% of such domains, and more preferably 0.1 to 0% of such domains. Ordinarily, the NTNRα ECD will have an amino acid sequence having at least about 60% amino acid sequence identity with the amino acid sequence of the ECD of an NTNRα, for example as indicated in FIGS. 1A–1C or 2A–2D for NTNRα or the corresponding sequences provided herein, e.g. mouse sequences, preferably at least about 65%, more preferably at least about 75%, even more preferably at least about 80%, even more preferably at least about 90%, with increasing preference of 95%, to at least 99% amino acid sequence identity, and finally to 100% identity, and thus includes NTNRα variants as defined below. Preferred sequences will be at least 16 amino acids long, preferably at least 20 amino acids long, and even more preferably at least 40 amino acids long.

"NTNRα variant" means a biologically active NTNRα as defined below having less than 100% sequence identity (but at least+60% identity) with a NTNRα, for example, having the deduced amino acid sequence shown in FIGS. 1A–1C or 2A–2D for NTNRα or with the sequences provided herein. Such NTNRα variants include NTNRα polypeptides wherein one or more amino acid residues are added at the N- or C-terminus of, or within, a NTNRα sequence; from about one to thirty amino acid residues are deleted, and optionally substituted by one or more amino acid residues; and derivatives of the above polypeptides, wherein an amino acid residue has been covalently modified so that the resulting product has a non-naturally occurring amino acid. Ordinarily, a biologically active NTNRα variant will have an amino acid sequence having about 60% amino acid sequence identity with the amino acid sequence of a naturally-occurring NTNRα (e.g., as shown in FIGS. 1A–1C or 2A–2D or the corresponding sequences provided herein), preferably at least about 65%, more preferably at least about 75%, even more preferably at least about 80%, even more preferably at least about 90%, with increasing preference of 95%, to at least 99% amino acid sequence identity, and finally to 100% identity.

A "chimeric NTNRα" is a polypeptide comprising full-length NTNRα or one or more domains thereof (e.g., the extracellular domain) fused or bonded to heterologous polypeptide. The chimeric NTNRα will generally share at least one biological property in common with NTNRα. Examples of chimeric NTNRαs include immunoadhesins and epitope-tagged NTNRα.

The term "immunoadhesin" is used interchangeably with the expression "NTNRα-immunoglobulin chimera" and refers to a chimeric molecule that combines a portion of the NTNRα (generally the extracellular domain thereof) with an immunoglobulin sequence. The immunoglobulin sequence preferably, but not necessarily, is an immunoglobulin constant domain. The immunoglobulin moiety in the chimeras of the present invention may be obtained from IgG1, IgG2, IgG3 or IgG4 subtypes, IgA, IgE, IgD or IgM, but preferably IgG1 or IgG3.

The term "epitope-tagged" when used herein refers to a chimeric polypeptide comprising NTNRα fused to a "tag polypeptide". The tag polypeptide has enough residues to provide an epitope against which an antibody thereagainst can be made, yet is short enough such that it does not interfere with biological activity of the NTNRα. The tag polypeptide preferably also is fairly unique so that the antibody thereagainst does not substantially cross-react with other epitopes. Suitable tag polypeptides generally have at least six amino acid residues and usually between about 8–50 amino acid residues (preferably between about 9–30 residues). Preferred are poly-histidine sequences, which bind nickle, allowing isolation of the tagged protein by Ni-NTA chromatography as described (Lindsay et al. *Neuron* 17:571–574 (1996)), for example.

"Isolated NTNRα" means NTNRα that has been purified from a NTNRα source or has been prepared by recombinant or synthetic methods and is sufficiently free of other peptides or proteins (1) to obtain at least 15 and preferably 20 amino acid residues of the N-terminal or of an internal amino acid sequence by using a spinning cup sequenator or the best commercially available amino acid sequenator marketed or as modified by published methods as of the filing date of this application, or (2) to homogeneity by SDS-PAGE under non-reducing or reducing conditions using Coomassie blue or, preferably, silver stain. Homogeneity here means less than about 5% contamination with other source proteins.

"Essentially pure" protein means a composition comprising at least about 90% by weight of the protein, based on total weight of the composition, preferably at least about 95% by weight. "Essentially homogeneous" protein means a composition comprising at least about 99% by weight of protein, based on total weight of the composition.

"Biological property" when used in conjunction with either "NTNRα" or "isolated NTNRα" means having an effector or antigenic function or activity that is directly or indirectly caused or performed by native sequence NTNRα (whether in its native or denatured conformation). Effector functions include ligand binding, and enhancement of survival, differentiation and/or proliferation of cells (especially proliferation of cells). However, effector functions do not include possession of an epitope or antigenic site that is capable of cross-reacting with antibodies raised against native sequence NTNRα.

An "antigenic function" means possession of an epitope or antigenic site that is capable of cross-reacting with antibodies raised against native sequence NTNRα. The principal antigenic function of a NTNRα polypeptide is that it binds with an affinity of at least about $10^6$ L/mole to an antibody raised against native sequence NTNRα. Ordinarily, the polypeptide binds with an affinity of at least about $10^7$ L/mole. The antibodies used to define "antigenic function" are rabbit polyclonal antibodies raised by formulating the NTNRα in Freund's complete adjuvant, subcutaneously injecting the formulation, and boosting the immune response by intraperitoneal injection of the formulation until the titer of the anti-NTNRα antibody plateaus.

"Biologically active" when used in conjunction with either "NTNRα" or "isolated NTNRα" means a NTNRα polypeptide that exhibits or shares an effector function of native sequence NTNRα and that may (but need not), in addition, possess an antigenic function. A principal effector function of the NTNRα is its ability to bind NTN. Another principal effector function of NTNRα is activating Ret tyrosine kinase (resulting in Ret autophosphorylation) to activate downstream pathways mediated by Ret signaling function.

"Antigenically active" NTNRα is defined as a polypeptide that possesses an antigenic function of NTNRα and that may (but need not) in addition possess an effector function.

"Percent amino acid sequence identity" with respect to the NTNRα sequence is defined herein as the percentage of amino acid residues in the candidate sequence that are identical with the residues in the NTNRα sequence, after aligning the sequences and introducing gaps, if necessary, to achieve the maximum percent sequence identity, and not considering any conservative substitutions as part of the sequence identity. None of N-terminal, C-terminal, or internal extensions, deletions, or insertions into the candidate NTNRα sequence shall be construed as affecting sequence identity or homology.

"NTN ligand" is a molecule which binds to and preferably activates native sequence NTNRα. The ability of a molecule to bind to NTNRα can be determined, for example, by the ability of the putative ligand to bind to NTNRα immunoadhesin coated on an assay plate, for example. Specificity of binding can be determined by comparing binding to GDNFRα. Competitive binding of NTN to NTNRα is a preferred property of the ligand. The thymidine incorporation assay provides another means for screening for ligands which activate NTNRα function.

A "thymidine incorporation assay" can be used to screen for molecules which activate the NTNRα. In order to perform this assay, IL-3 dependent Baf3 cells (Palacios et al., Cell, 41:727–734 (1985)) are stably transfected with full length native sequence NTNRα as described herein and Ret. The NTNRα/Ret/Baf3 cells so generated are starved of IL-3 for 24 hours in a humidified incubator at 37° C. in 5%$CO_2$ and air. Following IL-3 starvation, the cells are plated out in 96 well culture dishes with, or without, a test sample containing a potential agonist (such test samples are optionally diluted) and cultured for 24 hours in a cell culture incubator. 20 µl of serum free RPMI media containing 1 µCi of $^3$H thymidine is added to each well for the last 6–8 hours. The cells are then harvested in 96 well filter plates and washed with water. The filters are then counted using a Packard Top Count Microplate Scintillation Counter, for example. Agonists are expected to induce a statistically significant increase (to a P value of 0.05) in $^3$H uptake, relative to control. Preferred agonists leads to an increase in $^3$H uptake which is at least two fold of that of the control. Other assays are described herein.

An "isolated" NTNRα nucleic acid molecule is a nucleic acid molecule that is identified and separated from at least one contaminant nucleic acid molecule with which it is ordinarily associated in the natural source of the NTNRα nucleic acid. An isolated NTNRα nucleic acid molecule is other than in the form or setting in which it is found in nature. Isolated NTNRα nucleic acid molecules therefore are distinguished from the NTNRα nucleic acid molecule as it exists in natural cell. However, an isolated NTNRα nucleic acid molecule includes NTNRα nucleic acid molecules contained in cells that ordinarily express NTNRα where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

The term "antibody" is used in the broadest sense and specifically covers monoclonal antibodies, antibody compositions with polyepitopic specificity, bispecific antibodies, diabodies, and single-chain molecules, as well as antibody fragments (e.g., Fab, F(ab')$_2$, and Fv), so long as they exhibit the desired biological activity.

The term "monoclonal antibody" as used herein refers to an antibody obtained from a population of substantially homogeneous antibodies, ie., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256: 495 (1975), or may be made by recombinant DNA methods (see, e.g., U.S. Pat. No. 4,816,567 (Cabilly et al.)). The "monoclonal antibodies" may also be isolated from phage antibody libraries using the techniques described in Clackson et al., 624–628 (1991) and Marks et al., J. Mol. Biol., 222:581–597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Cabilly et al., supra; Morrison et al., Proc. Natl. Acad. Sci. USA, 81:6851–6855 (1984)).

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., *Nature,* 321:522–525 (1986); Reichmann et al., *Nature,* 332:323–329 (1988); and Presta, *Curr. Op. Struct. Biol.,* 2:593–596 (1992). The humanized antibody includes a Primatized™ antibody wherein the antigen-binding region of the antibody is derived from an antibody produced by immunizing macaque monkeys with the antigen of interest.

"Non-immunogenic in a human" means that upon contacting the polypeptide of interest in a physiologically acceptable carrier and in a therapeutically effective amount with the appropriate tissue of a human, no state of sensitivity or resistance to the polypeptide of interest is demonstrable upon the second administration of the polypeptide of interest after an appropriate latent period (e.g. 8 to 14 days).

By "agonist antibody" is meant an antibody which is a NTNRα ligand, able to activate native sequence NTNRα.

A "neutralizing antibody" is one which is able to block or significantly reduce an effector function of native sequence NTNRα. For example, a neutralizing antibody may inhibit or reduce NTNRα activation by a NTN ligand, as determined, for example, in a neurite survival assays, a NTN binding assay, or other assays taught herein or known in the art.

The phrase "enhancing proliferation of a cell" encompasses the step of increasing the extent of growth and/or reproduction of the cell relative to an untreated cell either in vitro or in vivo. An increase in cell proliferation in cell culture can be detected by counting the number of cells before and after exposure to a molecule of interest. The extent of proliferation can be quantified via microscopic examination of the degree of confluence. Cell proliferation can also be quantified using the thymidine incorporation assay described herein.

By "enhancing differentiation of a cell" is meant the act of increasing the extent of the acquisition or possession of one or more characteristics or functions which differ from that of the original cell (ie. cell specialization). This can be detected by screening for a change in the phenotype of the cell (e.g., identifying morphological changes in the cell).

"Physiologically acceptable" carriers, excipients, or stabilizers are ones which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

As used herein, the term "salvage receptor binding epitope" refers to an epitope of the Fc region of an IgG molecule (e g., IgG1, IgG2, IgG3, and IgG4) that is responsible for increasing the in vivo serum half-life of the IgG molecule. Exemplary salvage receptor binding epitope sequences include HQNLSDGK; HQNISDGK; HQSLGTQ; VISSHLGQ; and PKNSSMISNTP.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α, and -β, mullerian-inhibiting substance; mouse gonadotropin-associated peptide; inhibin; activin; vascular endothelial growth factor, integrin; thrombopoietin (TPO); neurotrophic factors or nerve growth factors such as NGF-β, NT-3, NT-4, NT-6, BDNF, CNTF, GDNF, AL-1 and other eph-receptor family ligands; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-11, IL-12; and other polypeptide factors including LIF and kit ligand (KL). As used herein, the term cytokine includes proteins from natural sources or from recombinant cell culture and biologically active equivalents of the native sequence cytokines. Also included are genetically engineered molecules with cytokine activity such as TrkA-IgG or other soluble receptor chimeras.

"Treatment" refers to both therapeutic treatment and prophylactic or preventative measures. Those in need of treatment include those already with the disorder as well as those in which the disorder is to be prevented.

"Mammal" for purposes of treatment refers to any animal classified as a mammal, including humans, domestic and farm animals, and zoo, sports, or pet animals, such as dogs, horses, cats, cows, etc. Preferably, the mammal is human.

By "solid phase" is meant a non-aqueous matrix to which a reagent of interest (e.g., the NTNRα or an antibody thereto) can adhere. Examples of solid phases encompassed herein include those formed partially or entirely of glass (e.g., controlled pore glass), polysaccharides (e.g, agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

Modes for carrying out the invention are presented herein. Glial cell line-derived neurotrophic factor ("GDNF") and Neurturin ("NTN") are two structurally related, potent survival factors for sympathetic sensory and central nervous system neurons (Lin et al. *Science* 260:1130–1132 (1993); Henderson et al. *Science* 266:1062–1064 (1994); Buj-Bello et al., *Neuron* 15:821–828 (1995); Kotzbauer et al. *Nature* 384:467–470 (1996)). Whereas GDNF was shown to mediate its actions through a multi-component receptor system composed of a ligand binding glycosyl-phosphatidyl inositol (GPI) linked protein (designated GDNFRα) and the transmembrane tyrosine kinase Ret (Treanor et al. *Nature* 382:80–83 (1996); Jing et al. *Cell* 85:1113–1124 (1996); Trupp et al. *Nature* 381:785–789 (1996); Durbec et al. *Nature* 381:789–793 (1996)), the mechanism by which the NTN signal is transmitted has not been previously elucidated. Described herein is the isolation, sequence, and tissue distribution of a GPI-linked protein and its gene, designated NTNRα, which is shown to modulate response to NTN but not GDNF. It is shown herein that it is structurally related to GDNFRα. Using recombinant proteins in a cell free system, it is shown that NTNRα binds NTN (Kd~10 pM) but not GDNF, and that NTN does not bind GDNFRα with a high affinity. Also shown is that cellular responses to NTN require the presence of NTNRα. Ligand bound NTNRα induces phosphorylation of the tyrosine kinase receptor Ret. These findings identify Ret and NTNRα, respectively, as signalling and ligand binding components of a receptor for NTN and related ligands. This defines a novel neurotrophic and differentiation factor receptor family of receptors containing a shared transmembrane protein tyrosine kinase (Ret) and a ligand specific GPI-linked protein (NTNRα).

Glial cell line-derived neurotrophic factor ("GDNF") (Lin et al., *Science,* 260:1130–1132 (1993); WO 93/06116, which are incorporated herein in its entirety), is a potent survival factor for midbrain dopaminergic (Lin et al., *Science,* 260:1130–1132 (1993); Strömberg et al., *Exp. Neurol.,* 124:401–412 (1993); Beck et al., *Nature,* 373:339–341 (1995); Kearns et al., *Brain Res.,* 672:104–111 (1995); Tomac et al., *Nature,* 373:335–339 (1995)) spinal motor (Henderson et al., *Science,* 266:1062–1064 (1994); Oppenheim et al., *Nature,* 373:344–346 (1995); Yan et al., *Nature,* 373:341–344 (1995)) and noradrenergic neurons (Arenas et al., *Neuron,* 15:1465–1473 (1995)), which degenerate in Parkinson's disease (Hirsch et al., *Nature,* 334:345–348 (1988); Hornykiewicz *Mt. Sinai J. Med.,* 55:11–20(1988)), amyotrophic lateral sclerosis (Hirano, Amyotrophic Lateral Sclerosis and Other Motor Neuron Diseases, P. Rowland, ed. (New York: Raven Press, Inc.) pp. 91–101 (1991)), and Alzheimer's disease (Marcynuik et al., *J. Neurol. Sci.,* 76:335–345 (1986); Cash et al., *Neurology,* 37:42–46 (1987); Chan-Palay et al., *Comp. Neurol.,* 287:373–392 (1989)) respectively. Based on mice genetically engineered to lack GDNF, additional biological roles for GDNF have been reported: the development and/or survival of enteric, sympathetic, and sensory neurons and the renal system, but not for catecholaminergic neurons in the central nervous system (CNS) (Moore et al. *Nature* 382:76–79 (1996); Pichel et al. *Nature* 382:73–76 (1996); Sanchez et al. *Nature* 382:70–73 (1996)). Despite the physiological and clinical importance of GDNF, little is known about its mechanism of action.

Cytokine receptors frequently assemble into multisubunit complexes. Sometimes, the a subunit of this complex is involved in binding the cognate growth factor and the β-subunit may contain an ability to transduce a signal to the cell. Without wishing to be bound by theory, these receptors have been assigned to three subfamilies depending on the complexes formed. Subfamily 1 includes the receptors for EPO, granulocyte colony-stimulating factor (G-CSF), interleukin-4 (IL-4), interleukin-7 (IL-7), growth hormone (GH), and prolactin (PRL). Ligand binding to receptors belonging to this subfamily is thought to result in homodimerization of the receptor. Subfamily 2 includes receptors for IL-3, granulocyte-macrophage colony-stimulating factor (GM-CSF), interleukin-5 (IL-S), interleukin-6 (IL-6), leukemia inhibitory factor (LIF), oncostatin M (OSM), and ciliary neurotrophic factor (CNTF). Subfamily 2 receptors are heterodimers having an α-subunit for ligand binding, and P-subunit (either the shared β-subunit of the IL-3, GM-CSF, and IL-5 receptors or the gpt30 subunit of the IL-6, LIF, OSM, and CNTF receptors) for signal transduction. Subfamily 3 contains only the interleukin-2 (IL-2) receptor. The β and γ subunits of the IL-2 receptor complex are cytokine-receptor polypeptides which associate with the α-subunit of the unrelated Tac antigen.

The present invention is based on the discovery of the NTNRα, a protein that binds NTN with a high affinity. The experiments described herein demonstrate that this molecule is a receptor which appears to play a role in mediating responses to NTN. In particular, this receptor has been found to be present in a variety of tissue and cell populations, including neurons, thus indicating that NTN ligands, such as agonist antibodies, can be used to stimulate proliferation, growth, survival, differentiation, metabolism, or regeneration of NTNRα- and Ret-containing cells.

Techniques suitable for the production of NTNRα are well known in the art and include isolating NTNRα from an endogenous source of the polypeptide, peptide synthesis (using a peptide synthesizer) and recombinant techniques (or any combination of these techniques). The preferred technique for production of NTNRα is a recombinant technique to be described below.

Most of the discussion below pertains to recombinant production of NTNRα by culturing cells transformed with a vector containing NTNRα nucleic acid and recovering the polypeptide from the cell culture. It is further envisioned that the NTNRα of this invention may be produced by homologous recombination, as provided for in WO 91/06667, published May 16, 1991.

Briefly, this method involves transforming primary human cells containing a NTNRα-encoding gene with a construct (ie., vector) comprising an amplifiable gene (such as dihydrofolate reductase (DHFR) or others discussed below) and at least one flanking region of a length of at least about 150 bp that is homologous with a DNA sequence at the locus of the coding region of the NTNRα gene to provide amplification of the NTNRα gene. The amplifiable gene must be at a site that does not interfere with expression of the NTNRα gene. The transformation is conducted such that the construct becomes homologously integrated into the genome of the primary cells to define an amplifiable region.

Primary cells comprising the construct are then selected for by means of the amplifiable gene or other marker present in the construct. The presence of the marker gene establishes the presence and integration of the construct into the host genome. No further selection of the primary cells need be made, since selection will be made in the second host. If desired, the occurrence of the homologous recombination event can be determined by employing PCR and either sequencing the resulting amplified DNA sequences or determining the appropriate length of the PCR fragment when DNA from correct homologous integrants is present and expanding only those cells containing such fragments. Also if desired, the selected cells may be amplified at this point by stressing the cells with the appropriate amplifying agent (such as methotrexate if the amplifiable gene is DHFR), so that multiple copies of the target gene are obtained. Preferably, however, the amplification step is not conducted until after the second transformation described below.

After the selection step, DNA portions of the genome, sufficiently large to include the entire amplifiable region, are isolated from the selected primary cells. Secondary mammalian expression host cells are then transformed with these genomic DNA portions and cloned, and clones are selected that contain the amplifiable region. The amplifiable region is then amplified by means of an amplifying agent if not already amplified in the primary cells. Finally, the secondary expression host cells now comprising multiple copies of the amplifiable region containing NTNRα are grown so as to express the gene and produce the protein.

The conserved structure and sequence of the mammalian NTNRα and the elucidation of the cDNA sequence which encodes the rat and mouse receptor, as well as human sequences disclosed herein, make it possible to clone gene sequences from other mammals which encode the NTNRα. Of particular interest to the present invention is the ability to clone the human NTNRα molecules using the sequences disclosed herein. The DNA encoding NTNRα may be obtained from any cDNA library prepared from tissue believed to possess the NTNRα mRNA and to express it at a detectable level, as shown herein in the Examples. Accordingly, NTNRα DNA can be conveniently obtained from a cDNA library prepared, for example, from mammalian fetal liver, brain, muscle, intestine, and peripheral nerves. The NTNRα-encoding gene may also be obtained from a genomic library or by oligonucleotide synthesis.

Libraries are screened with probes (such as antibodies to the NTNRα or oligonucleotides of about 20–80 bases) designed to identify the gene of interest or the protein encoded by it. Screening the cDNA or genomic library with the selected probe may be conducted using standard procedures as described in chapters 10–12 of Sambrook et al., *Molecular Cloning: A Laboratory Manual* (New York: Cold Spring Harbor Laboratory Press, 1989). An alternative means to isolate the gene encoding NTNRα is to use PCR methodology as described in section 14 of Sambrook et al., supra.

A preferred method of practicing this invention is to use carefully selected oligonucleotide sequences to screen cDNA libraries from various human tissues, preferably human fetal liver. The oligonucleotide sequences selected as probes should be of sufficient length and sufficiently unambiguous that false positives are minimized. Preferred sequences are obtained from the naturally-occurring NTNRα disclosed herein.

The oligonucleotide must be labeled such that it can be detected upon hybridization to DNA in the library being screened. The preferred method of labeling is to use $^{32}$P-labeled ATP with polynucleotide kinase, as is well known in the art, to radiolabel the oligonucleotide. However, other methods may be used to label the oligonucleotide, including, but not limited to, biotinylation or enzyme labeling.

Amino acid sequence variants of NTNRα are prepared by introducing appropriate nucleotide changes into the NTNRα DNA, or by synthesis of the desired NTNRα polypeptide. Such variants represent insertions, substitutions, and/or specified deletions of, residues within or at one or both of the ends of the amino acid sequence of a naturally occurring NTNRα, such as the NTNRα shown in FIGS. 1A–1C or 2A–2D or sequences disclosed herein. Preferably, these variants represent insertions and/or substitutions within or at one or both ends of the mature sequence, and/or insertions, substitutions and/or specified deletions within or at one or both of the ends of the signal sequence of the NTNRα. Any combination of insertion, substitution, and/or specified deletion is made to arrive at the final construct, provided that the final construct possesses the desired biological activity as defined herein. The amino acid changes also may alter post-translational processes of the NTNRα, such as changing the number or position of glycosylation sites, altering the membrane anchoring characteristics, and/or altering the intracellular location of the NTNRα by inserting, deleting, or otherwise affecting the leader sequence of the NTNRα.

Variations in the native sequence as described above can be made using any of the techniques and guidelines for conservative and non-conservative mutations set forth in U.S. Pat. No. 5,364,934. These include oligonucleotide-mediated (site-directed) mutagenesis, alanine scanning, and PCR mutagenesis. See also, for example, Table I therein and the discussion surrounding this table for guidance on selecting amino acids to change, add, or delete.

The nucleic acid (e.g., cDNA or genomic DNA) encoding the NTNRα is inserted into a replicable vector for further cloning (amplification of the DNA) or for expression. Many vectors are available. The vector components generally include, but are not limited to, one or more of the following: a signal sequence, an origin of replication, one or more marker genes, an enhancer element, a promoter, and a transcription termination sequence.

The NTNRαs of this invention may be produced recombinantly not only directly, but also as a fusion polypeptide with a heterologous polypeptide, which is preferably a signal sequence or other polypeptide having a specific cleavage site at the N-terminus of the mature protein or polypeptide. In general, the signal sequence may be a component of the vector, or it may be a part of the NTNRα DNA that is inserted into the vector. The heterologous signal sequence selected preferably is one that is recognized and processed (i.e., cleaved by a signal peptidase) by the host cell. For prokaryotic host cells that do not recognize and process the native NTNRα signal sequence, the signal sequence is substituted by a prokaryotic signal sequence selected, for example, from the group of the alkaline phosphatase, penicillinase, lpp, or heat-stable enterotoxin 11 leaders. For yeast secretion the native signal sequence may be substituted by, eg., the yeast invertase leader, a factor leader (including Saccharomyces and Kluyveromyces α-factor leaders, the latter described in U.S. Pat. No. 5,010, 182 issued Apr. 23, 1991), or acid phosphatase leader, the *C. albicans* glucoarnylase leader (EP 362,179 published Apr. 4, 1990), or the signal described in WO 90/13646 published Nov. 15, 1990. In mammalian cell expression the native signal sequence (eg., the NTNRα presequence that normally directs secretion of NTNRα from human cells in vivo) is satisfactory, although other mammalian signal sequences may be suitable, such as signal sequences from other animal NTNRαs, and signal sequences from secreted polypeptides of the same or related species, as well as viral secretory leaders, for example, the herpes simplex gD signal.

The DNA for such precursor region is ligated in reading frame to DNA encoding the mature NTNRα or a soluble variant thereof.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Most expression vectors are "shuttle" vectors, ie., they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA may also be amplified by insertion into the host genome. This is readily accomplished using Bacillus species as hosts, for example, by including in the vector a DNA sequence that is complementary to a sequence found in Bacillus genomic DNA. Transfection of Bacillus with this vector results in homologous recombination with the genome and insertion of NTNRα DNA. However, the recovery of genomic DNA encoding NTNRα is more complex than that of an exogenously replicated vector because restriction enzyme digestion is required to excise the NTNRα DNA.

Expression and cloning vectors should contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the NTNRα nucleic acid,. such as DHFR or thymidine kinase. The mammalian cell transformants are placed under selection pressure that only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes NTNRα. Amplification is the process by which genes in greater demand for the production of a protein critical for growth are reiterated in tandem within the chromosomes of successive generations of recombinant cells. Increased quantities of NTNRα are synthesized from the amplified DNA. Other examples of amplifiable genes include met allothionein-I and -II, preferably primate met allothionein genes, adenosine deaminase, ornithine decarboxylase, etc. A preferred vector system is provided in U.S. Pat. No. 5,561,053.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub et al., *Proc. Natl. Acad. Sci. USA*, 77:4216 (1980). The transformed cells are then exposed to increased levels of methotrexate. This leads to the synthesis of multiple copies of the DHFR gene, and, concomitantly, multiple copies of other DNA comprising the expression vectors, such as the DNA encoding NTNRα. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060).

Alternatively, host cells (particularly wild-type hosts that contain endogenous DHFR) transformed or co-transformed with DNA sequences encoding NTNRα, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et at., *Nature*, 282:39 (1979)). The trp1 gene provides a selection marker for a mutant strain of yeast lacking the ability to grow in tryptophan, for example, ATCC No. 44076 or PEP4-1. Jones, *Genetics*, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of Kluyveromyces yeasts. Bianchi et al., *Curr. Genet.*, 12:185 (1987). More recently, an expression system for large-scale production of recombinant calf chymosin was reported for *K. lactis*. Van den Berg, *Bio/Technology*, 8:135 (1990). Stable multicopy expression vectors for secretion of mature recombinant human serum albumin by industrial strains of Kluyveromyces have also been disclosed. Fleer et al., *Bio/Technology*, 9:968–975 (1991).

Expression and cloning vectors usually contain a promoter that is recognized by the host organism and is operably linked to the NTNRα nucleic acid. Promoters are untranslated sequences located upstream (5') to the start codon of a structural gene (generally within about 100 to 1000 bp) that control the transcription and translation of particular nucleic acid sequence, such as the NTNRα nucleic acid sequence, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to NTNRα-encoding DNA by removing the promoter from the source DNA by restriction enzyme digestion and inserting the isolated promoter sequence into the vector. Both the native NTNRα promoter sequence and many heterologous promoters may be used to direct amplification and/or expression of the NTNRα DNA. However, heterologous promoters are preferred, as they generally permit greater transcription and higher yields of NTNRα as compared to the native NTNRα promoter.

Promoters suitable for use with prokaryotic hosts include the β-lactamase and lactose promoter systems (Chang et al., *Nature*, 275:615 (1978); Goeddel et al., *Nature*, 281:544 (1979)), alkaline phosphatase, a tryptophan (trp) promoter system (Goeddel, *Nucleic Acids Res.*, 8:4057 (1980); EP 36,776), and hybrid promoters such as the tac promoter. deBoer et al., *Proc. Natl. Acad Sci. USA*, 80:21–25 (1983). However, other known bacterial promoters are suitable. Their nucleotide sequences have been published, thereby enabling a skilled worker operably to ligate them to DNA encoding NTNRα (Siebenlist et al., *Cell*, 20:269 (1980)) using linkers or adaptors to supply any required restriction sites. Promoters for use in bacterial systems also will contain a Shine-Delgarno (S.D.) sequence operably linked to the DNA encoding NTNRα.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase (Hitzeman et al., *J. Biol. Chem.*, 255:2073 (1980)) or other glycolytic enzymes (Hess et al., *J. Adv. Enzyme Reg.*, 7:149 (1968); Holland, *Biochemistry*, 17:4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, met allothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

NTNRα transcription from vectors in mammalian host cells is controlled, for example, by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, and from the promoter normally associated with the NTNRα sequence, provided such promoters are compatible with the host cell systems.

The early and late promoters of the SV40 virus are conveniently obtained as an SV40 restriction fragment that also contains the SV40 viral origin of replication. Fiers et al., *Nature*, 273:113 (1978); Mulligan et al., *Science*, 209:1422–1427(1980); Pavlakis et al., *Proc. Natl. Acad. Sci. USA*, 78:7398–7402 (1981). The immediate early promoter of the human cytomegalovirus is conveniently obtained as a HindIII E restriction fragment. Greenaway et al., *Gene*, 18:355–360 (1982). A system for expressing DNA in mammalian hosts using the bovine papilloma virus as a vector is disclosed in U.S. Pat. No. 4,419,446. A modification of this system is described in U.S. Pat. No. 4,601,978. See also Gray et al., *Nature*, 295:503–508 (1982) on expressing cDNA encoding immune interferon in monkey cells; Reyes et al., *Nature*, 297:598–601 (1982) on expression of human β-interferon cDNA in mouse cells under the control of a thymidine kinase promoter from herpes simplex virus; Canaani et al., *Proc. Natl. Acad. Sci. USA*, 79:5166–5170 (1982) on expression of the human interferon β1 gene in cultured mouse and rabbit cells; and Gorman et al., *Proc. Natl. Acad. Sci. USA*, 79:6777–6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

Transcription of a DNA encoding the NTNRα of this invention by higher eukaryotes is often increased by inserting an enhancer sequence into the vector. Enhancers are cis-acting elements of DNA, usually about from 10 to 300 bp, that act on a promoter to increase its transcription. Enhancers are relatively orientation and position independent, having been found 5' (Laimins et al., *Proc. Natl. Acad. Sci. USA*, 78:993 (1981)) and 3' (Lusky et al., *Mol. Cell Bio.*, 3:1108 (1983)) to the transcription unit, within an intron (Banerji et al., *Cell*, 33:729 (1983)), as well as within the coding sequence itself. Osborne et al., *Mol. Cell Bio.*, 4:1293 (1984). Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, *Nature*, 297:17–18 (1982) on enhancing elements for activation of eukaryotic promoters. The enhancer may be spliced into the vector at a position 5' or 3' to the NTNRα-encoding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding NTNRα.

Construction of suitable vectors containing one or more of the above-listed components employs standard ligation techniques. Isolated plasmids or DNA fragments are cleaved, tailored, and re-ligated in the form desired to generate the plasmids required.

For analysis to confirm correct sequences in plasmids constructed, the ligation mixtures are used to transform *E.* coli K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.,* 9:309 (1981) or by the method of Maxam et al., *Methods in Enzymology,* 65:499 (1980).

Particularly useful in the practice of this invention are expression vectors that provide for the transient expression in mammalian cells of DNA encoding NTNRα. In general, transient expression involves the use of an expression vector that is able to replicate efficiently in a host cell, such that the host cell accumulates many copies of the expression vector and, in turn, synthesizes high levels of a desired polypeptide encoded by the expression vector. Sambrook et al., supra, pp. 16.17–16.22. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying analogs and variants of NTNRα that are biologically active NTNRα.

Other methods, vectors, and host cells suitable for adaptation to the synthesis of NTNRα in recombinant vertebrate cell culture are described in Gething et al., *Nature,* 293:620–625 (1981); Mantei et al., *Nature,* 281:40–46 (1979); EP 117,060; and EP 117,058. A particularly useful plasmid for mammalian cell culture expression of NTNRα is pRK5 (EP 307,247) or pSV16B. WO 91/08291 published Jun. 13, 1991.

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as Escherichia, e.g., *E. coli,* Enterobacter, Erwinia, Klebsiella, Proteus, Salmonella, e.g., *Salmonella typhimurium,* Serratia, e.g., *Serratia marcescans,* and Shigella, as well as Bacilli such as *B. subtilis* and *B. licheniformis* (e.g., *B. licheniformis* 41P disclosed in DD 266,710 published Apr. 12, 1989), Pseudomonas such as *P. aeruginosa,* and Streptomyces. One preferred *E. coli* cloning host is *E. coil* 294 (ATCC 31,446), although other strains such as *E. coli* B, *E. coli* X1776 (ATCC 31,537), and *E. coil* W3110 (ATCC 27,325) are suitable. These examples are illustrative rather than limiting. Strain W3110 is a particularly preferred host or parent host because it is a common host strain for recombinant DNA product fermentations. Preferably, the host cell should secrete minimal amounts of proteolytic enzymes. For example, strain W3110 may be modified to effect a genetic mutation in the genes encoding proteins, with examples of such hosts including *E. coi* W3110 strain 27C7. The complete genotype of 27C7 is tonAΔptr3 phoAΔE15 Δ(argF-lac)169 ompTΔdegP41kan'. Strain 27C7 was deposited on Oct. 30, 1991 in the American Type Culture Collection as ATCC No. 55,244. Alternatively, the strain of *E. coli* having mutant periplasmic protease disclosed in U.S. Pat. No. 4,946,783 issued Aug. 7, 1990 may be employed. Alternatively still, methods of cloning, e.g., PCR or other nucleic acid polymerase reactions, are suitable.

In addition to prokaryotes, eukaryotic microbes such as filamentous fungi or yeast are suitable cloning or expression hosts for NTNRα-encoding vectors. *Saccharomyces cerevisiae,* or common baker's yeast, is the most commonly used among lower eukaryotic host microorganisms. However, a number of other genera, species, and strains are commonly available and useful herein, such as *Schizosaccharomyces pombe* (Beach et al., *Nature,* 290:140 (1981); EP 139,383 published May 2, 1985); Kluyveromyces hosts (U.S. Pat. No. 4,943,529; Fleer et al., supra) such as, e.g., *K. lactis* (MW98-8C, CBS683, CBS4574; Louvencourt et al., *J. Bacteriol.,* 737 (1983)), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., supra), *K. thermotolerans,* and *K. marxianus; yarrowia* (EP 402,226); *Pichia pastoris* (EP 183,070; Sreekrishna et al., *J. Basic Microbiol.,* 28:265–278 (1988)); *Candida; Trichoderma reesia* (EP 244,234); *Neurospora crassa* (Case et al., *Proc. Natl. Acad. Sci. USA,* 76:5259–5263 (1979)); Schwanniomyces such as *Schwanniomyces occidentalis* (EP 394,538 published Oct. 31, 1990); and filamentous fungi such as, e.g., Neurospora, Penicillium, Tolypocladium (WO 91/00357 published Jan. 10, 1991), and Aspergillus hosts such as *A. nidulans* (Ballance et al., *Biochem. Biophys. Res. Commun.,* 112:284–289 (1983); Tilbum et a., *Gene,* 26:205–221 (1983); Yelton et al., *Proc. Natl. Acad Sci. USA,* 81:1470–1474 (1984)) and *A. niger.* Kelly et al., *EMBO J.,* 4:475–479 (1985).

Suitable host cells for the expression of glycosylated NTNRα are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. See, e.g., Luckow et al., *Bio/Technology,* 6:47–55 (1988); Miller et al., in *Genetic Engineering,* Setlow et al., eds., Vol. 8 (Plenum Publishing, 1986), pp. 277–279; and Maeda et al., *Nature,* 315:592–594 (1985). A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens,* which has been previously manipulated to contain the NTNRα-encoding DNA. During incubation of the plant cell culture with *A. tumefaciens,* the DNA encoding the NTNRα is transferred to the plant cell host such that it is transfected, and will, under appropriate conditions, express the NTNRα-encoding DNA. In addition, regulatory and signal sequences compatible with plant cells are available, such as the nopaline synthase promoter and polyadenylation signal sequences. Depicker et al., *J. Mol. Appl. Gen.,* 1:561 (1982). In addition, DNA segments isolated from the upstream region of the T-DNA 780 gene are capable of activating or increasing transcription levels of plant-expressible genes in recombinant DNA-containing plant tissue. EP 321,196 published Jun. 21, 1989.

However, interest has been greatest in vertebrate cells, and propagation of vertebrate cells in culture (tissue culture) has become a routine procedure. See, e.g., *Tissue Culture,* Academic Press, Kruse and Patterson, editors (1973). Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); baby hamster kidney cells (BHK, ATCC CCL 10); Chinese hamster ovary cellst-DHFR (CHO, Urlaub et al., *Proc. Natl. Acad. Sci. USA*, 77:4216 (1980)); mouse sertoli cells (TM4, Mather, *Biol. Reprod.*, 23:243–251 (1980)); monkey kidney cells (CVI ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.*, 383:44–68 (1982)); MRC 5 cells; FS4 cells; and a human hepatoma line (Hep G2).

Host cells are transfected and preferably transformed with the above-described expression or cloning vectors for NTNRα production and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene*, 23:315 (1983) and WO 89/05859 published Jun. 29, 1989. In addition, plants may be transfected using ultrasound treatment as described in WO 91/00358 published Jan. 10, 1991.

For mammalian cells without such cell walls, the calcium phosphate precipitation method of Graham et al., *Virology*, 52:456–457 (1978) is preferred. General aspects of mammalian cell host system transformations have been described in U.S. Pat. No. 4,399,216 issued Aug. 16, 1983. Transformations into yeast are typically carried out according to the method of Van Solingen et al., *J. Bact.*, 130:946 (1977) and Hsiao et al., *Proc. Natl. Acad. Sci. USA*, 76:3829 (1979). However, other methods for introducing DNA into cells, such as by nuclear microinjection, electroporation, bacterial protoplast fusion with intact cells, or polycations, e.g., polybrene, polyornithine, etc., may also be used. For various techniques for transforming mammalian cells, see Keown et al., *Methods in Enzymology*, 185:527–537 (1990) and Mansour et al., *Nature*, 336:348–352 (1988).

Prokaryotic cells used to produce the NTNRα polypeptide of this invention are cultured in suitable media as described generally in Sambrook et al., supra.

The mammalian host cells used to produce the NTNRα of this invention may be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. In addition, any of the media described in Ham et al. *Meth. Enz.*, 58:44 (1979), Barnes et al., *Anal. Biochem.*, 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In general, principles, protocols, and practical techniques for maximizing the productivity of mammalian cell cultures can be found in *Mammalian Cell Biotechnology: a Practical Approach*, M. Butler, ed. (IRL Press, 1991).

The host cells referred to in this disclosure encompass cells in culture as well as cells that are within a host animal.

Gene amplification and/or expression may be measured in a sample directly, for example, by conventional Southern blotting, Northern blotting to quantitate the transcription of mRNA (Thomas, *Proc. Natl. Acad. Sci. USA*, 77:5201–5205 (1980)), dot blotting (DNA analysis), or in situ hybridization, using an appropriately labeled probe, based on the sequences provided herein. Various labels may be employed, most commonly radioisotopes, particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, can be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hsu et al., *Am. J. Clin. Path.*, 75:734–738 (1980).

Antibodies useful for immunohistochemical staining and/or assay of sample fluids may be either monoclonal or polyclonal, and may be prepared as described herein.

NTNRα (e.g., NTNRα ECD) preferably is recovered from the culture medium as a secreted polypeptide, although it also may be recovered from host cell lysates. If the NTNRα is membrane-bound, it can be released from the membrane using a suitable detergent solution (e.g. Triton-X 100).

When NTNRα is produced in a recombinant cell other than one of human origin, the NTNRα is completely free of proteins or polypeptides of human origin. However, it is necessary to purify NTNRα from recombinant cell proteins or polypeptides to obtain preparations that are substantially homogeneous as to NTNRα. As a first step, the culture medium or lysate can be centrifuged to remove particulate cell debris. NTNRα can then be purified from contaminant soluble proteins and polypeptides with the following procedures, which are exemplary of suitable purification procedures: by fractionation on an ion-exchange column; ethanol precipitation; reverse phase HPLC; chromatography on silica; chromatofocusing; immunoaffinity; epitope-tag binding resin; SDS-PAGE; ammonium sulfate precipitation; gel filtration using, for example, Sephadex G-75; and protein A Sepharose columns to remove contaminants such as IgG.

NTNRα variants in which residues have been deleted, inserted, or substituted are recovered in the same fashion as native sequence NTNRα, taking account of any substantial changes in properties occasioned by the variation. Immunoaffinity resins, such as a monoclonal anti-NTNRα resin, can be employed to absorb the NTNRα variant by binding it to at least one remaining epitope.

A protease inhibitor such as phenyl methyl sulfonyl fluoride (PMSF) also may be useful to inhibit proteolytic degradation during purification, and antibiotics may be included to prevent the growth of adventitious contaminants.

Covalent modifications of NTNRα polypeptides are included within the scope of this invention. Both native sequence NTNRα and amino acid sequence variants of the NTNRα may be covalently modified. One type of covalent modification of the NTNRα is introduced into the molecule by reacting targeted amino acid residues of the NTNRα with an organic derivatizing agent that is capable of reacting the N-terminal residue, the C-terminal residue, or with selected side chains.

Cysteinyl residues most commonly are reacted with a-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmalcimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Parabromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed under alkaline conditions because of the high $pK_a$ of the guanidine functional group. Furthermore, these reagents may react with the groups of lysine as well as with the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method being suitable.

Carboxyl side groups (aspartyl or glutamyl) are selectively modified by reaction with carbodiimides (R—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking NTNRα to a water-insoluble support matrix or surface for use in the method for purifying anti-NTNRα antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-((p-azidophenyl)dithio) propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties,* W. H. Freeman & Co., San Francisco, pp. 79–86 (1983)), acetylation of the N-terminal amine, and amidation of any C-terminal carboxyl group.

Another type of covalent modification of the NTNRα polypeptide included within the scope of this invention comprises altering the native glycosylation pattern of the polypeptide. By altering is meant deleting one or more carbohydrate moieties found in native NTNRα, and/or adding one or more glycosylation sites that are not present in the native NTNRα.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxylamino acid, most commonly serine or threonine, although 5-hydroxyproline or 5-hydroxylysine may also be used.

Addition of glycosylation sites to the NTNRα polypeptide is conveniently accomplished by altering the amino acid sequence such that it contains one or more of the above-described tripeptide sequences (for N-linked glycosylation sites). The alteration may also be made by the addition of, or substitution by, one or more serine or threonine residues to the native NTNRα sequence (for O-linked glycosylation sites). For ease, the NTNRα amino acid sequence is preferably altered through changes at the DNA level, particularly by mutating the DNA encoding the NTNRα polypeptide at preselected bases such that codons are generated that will translate into the desired amino acids. The DNA mutation(s) may be made using methods described above and in U.S. Pat. No. 5,364,934, supra.

Another means of increasing the number of carbohydrate moieties on the NTNRα polypeptide is by chemical or enzymatic coupling of glycosides to the polypeptide. These procedures are advantageous in that they do not require production of the polypeptide in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published Sep. 11, 1987, and in Aplin et al., CRC Crit. *Rev. Biochem.,* 259–306 (1981).

Removal of carbohydrate moieties present on the NTNRα polypeptide may be accomplished chemically or enzymatically. Chemical deglycosylation requires exposure of the polypeptide to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin, et al., *Arch. Biochem. Biophys.,* 259:52(1987) and by Edge et al., *Anal. Biochem.,* 118:131 (1981). Enzymatic cleavage of carbohydrate moieties on polypeptides can be achieved by the use of a variety of endo- and exo-glycosidases as described by Thotakura et al., *Meth. Enzymol.,* 138:350 (1987).

Glycosylation at potential glycosylation sites may be prevented by the use of the compound tunicamycin as described by Duskin et al., *J. Biol. Chem.,* 257:3105 (1982). Tunicamycin blocks the formation of protein-N-glycoside linkages.

Another type of covalent modification of NTNRα comprises linking the NTNRα polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Variants can be assayed as taught herein. A change in the immunological character of the NTNRα molecule, such as affinity for a given antibody, can be measured by a competitive-type immunoassay. Other potential modifications of protein or polypeptide properties such as redox or thermal stability, hydrophobicity, susceptibility to proteolytic degradation, or the tendency to aggregate with carriers or into multimers are assayed by methods well known in the art This invention encompasses chimeric polypeptides comprising NTNRα fused to a heterologous polypeptide. A chimeric NTNRα is one type of NTNRα variant as defined herein. In one preferred embodiment, the chimeric polypeptide comprises a fusion of the NTNRα with a tag polypeptide which provides an epitope to which an anti-tag antibody or molecule can selectively bind. The epitope-tag is generally provided at the amino- or carboxyl-terminus of the NTNRα. Such epitope-tagged forms of the NTNRα are desirable, as the presence thereof can be detected using a labeled antibody against the tag polypeptide. Also, provision of the epitope tag enables the NTNRα to be readily purified by affinity purification using the anti-tag antibody. Affinity purification techniques and diagnostic assays involving antibodies are described later herein.

Tag polypeptides and their respective antibodies are well known in the art. Examples include the flu HA tag polypeptide and its antibody 12CA5 (Field et al., *Mol. Cell. Biol.,* 8:2159–2165 (1988)); the c-myc tag and the 8F9, 3C7, 6E10, G4, B7 and 9E10 antibodies thereto (Evan et al., *Molecular and Cellular Biology,* 5:3610–3616 (1985)); and the Herpes Simplex virus glycoprotein D (gD) tag and its antibody. Paborsky et al., *Protein Engineering,* 3(6) :547–553 (1990). Other tag polypeptides have been disclosed. Examples include the Flag-peptide (Hopp et al., *BioTechnology,* 6:1204–1210 (1988)); the KT3 epitope peptide (Martin et al., *Science,* 255:192–194 (1992)); an α-tubulin epitope peptide (Skinner et al., *J. Biol. Chem.,* 266:15163–15166 (1991)); and the T7 gene 10 protein peptide tag. Lutz-Freyermuth et al., *Proc. Natl. Acad. Sci. USA,* 87:6393–6397 (1990). Once the tag polypeptide has been selected, an antibody thereto can be generated using the techniques disclosed herein. A C-terminal poly-histidine sequence tag is preferred. Poly-histidine sequences allow isolation of the tagged protein by Ni-NTA chromatography as described (Lindsay et al. *Neuron* 17:571–574 (1996)), for example.

The general methods suitable for the construction and production of epitope-tagged NTNRα are the same as those disclosed hereinabove. NTNRα-tag polypeptide fusions are most conveniently constructed by fusing the cDNA sequence encoding the NTNRα portion in-frame to the tag polypeptide DNA sequence and expressing the resultant DNA fusion construct in appropriate host cells. Ordinarily, when preparing the NTNRα-tag polypeptide chimeras of the present invention, nucleic acid encoding the NTNRα will be fused at its 3' end to nucleic acid encoding the N-terminus of the tag polypeptide, however 5' fusions are also possible.

Epitope-tagged NTNRα can be conveniently purified by affinity chromatography using the anti-tag antibody. The matrix to which the affinity antibody is attached is most often agarose, but other matrices are available (e.g. controlled pore glass or poly(styrenedivinyl)benzene). The epitope-tagged NTNRα can be eluted from the affinity column by varying the buffer pH or ionic strength or adding chaotropic agents, for example.

Chimeras constructed from a receptor sequence linked to an appropriate immunoglobulin constant domain sequence (immunoadhesins) are known in the art. Immunoadhesins reported in the literature include fusions of the T cell receptor* (Gascoigne et al., *Proc. Natl.Acad Sci. USA,* 84: 2936–2940 (1987)); CD4* (Capon et al., *Nature* 337: 525–531 (1989); Traunecker et al., *Nature,* 339: 68–70 (1989); Zettmeissl et al., *DNA Cell Biol. USA,* 9:347–353 (1990); Byrn et al., *Nature,* 344: 667–670 (1990)); L-selectin (homingreceptor)((Watson etal., *J. Cell. Biol.,* 110:2221–2229(1990); Watson et al., *Nature,* 349: 164–167 (1991)); CD44* (Aruffo et al., *Cell,* 61: 1303–1313 (1990)); CD28* and B7* (Linsley et al., *J. Exp. Med.,* 173: 721–730 (1991));CTLA-4* (Lisley et al., *J. Exp. Med.* 174:561–569 (1991)); CD22* (Stamenkovic et al., *Cell,* 66:1133–1144 (1991)); TNF receptor(Ashkenazi et al., *Proc. Natl. Acad Sci. USA,* 88: 10535–10539(1991); Lesslauer et al., *Eur. J. Immunol.,* 27:2883–2886(1991); Peppel et al., *J. Exp. Med.,* 174:1483–1489(1991)); NP receptors (Bennett et al., *J. Biol. Chem.* 266:23060–23067(1991)); and IgE receptor α* (Ridgway et al., *J. Cell. Biol.,* 115:abstr. 1448 (1991)), where the asterisk (*) indicates that the receptor is member of the immunoglobulin superfamily.

The simplest and most straightforward immunoadhesin design combines the binding region(s) of the "adhesin" protein with the hinge and Fc regions of an immunoglobulin heavy chain. Ordinarily, when preparing the NTNRα-immunoglobulin chimeras of the present invention, nucleic acid encoding the extracellular domain of the NTNRα will be fused C-terminally to nucleic acid encoding the N-terminus of an immunoglobulin constant domain sequence, however N-terminal fusions are also possible.

Typically, in such fusions the encoded chimeric polypeptide will retain at least functionally active hinge and CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain.

The precise site at which the fusion is made is not critical; particular sites are well known and may be selected in order to optimize the biological activity, secretion or binding characteristics of the NTNRα-immunoglobulin chimeras.

In some embodiments, the NTNRa-immunoglobulin chimeras are assembled as monomers, or hetero- or homo-multimer, and particularly as dimers or tetramers, essentially as illustrated in WO 91/08298.

In a preferred embodiment, the NTNRα extracellular domain sequence is fused to the N-terminus of the C-terminal portion of an antibody (in particular the Fc domain), containing the effector functions of an immunoglobulin, e.g. immunoglobulin $G_1$ (IgG1). It is possible to fuise the entire heavy chain constant region to the NTNRα extracellular domain sequence. However, more preferably, a sequence beginning in the hinge region just upstream of the papain cleavage site (which defines IgG Fc chemically; residue 216, taking the first residue of heavy chain constant region to be 114, or analogous sites of other immunoglobulins) is used in the fusion. In a particularly preferred embodiment, the NTNRα amino acid sequence is fused to the hinge region and CH2 and CH3, or to the CH1, hinge, CH2 and CH3 domains of an IgG1, IgG2, or IgG3 heavy chain. The precise site at which the fusion is made is not critical, and the optimal site can be determined by routine experimentation.

In some embodiments, the NTNRα-immunoglobulin chimeras are assembled as multimer, and particularly as homodimers or -tetramers. Generally, these assembled immunoglobulins will have known unit structures. A basic four chain structural unit is the form in which IgG, IgD, and IgE exist. A four unit is repeated in the higher molecular weight immunoglobulins; IgM generally exists as a pentamer of basic four units held together by disulfide bonds. IgA globulin, and occasionally IgG globulin, may also exist in multimeric form in serum. In the case of multimer, each four unit may be the same or different.

Alternatively, the NTNRα extracellular domain sequence can be inserted between immunoglobulin heavy chain and light chain sequences such that an immunoglobulin comprising a chimeric heavy chain is obtained. In this embodiment, the NTNRα sequence is fused to the 3' end of an immunoglobulin heavy chain in each arm of an immunoglobulin, either between the hinge and the CH2 domain, or between the CH2 and CH3 domains. Similar constructs have been reported by Hoogenboom et al., *Mol. Immunol.,* 28:1027–1037(1991).

Although the presence of an immunoglobulin light chain is not required in the immunoadhesins of the present invention, an immunoglobulin light chain might be present either covalently associated to an NTNRα-immunoglobulin heavy chain fusion polypeptide, or directly fused to the NTNRα extracellular domain. In the former case, DNA encoding an immunoglobulin light chain is typically coexpressed with the DNA encoding the NTNRα-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Methods suitable for the preparation of such structures are, for example, disclosed in U.S. Pat. No. 4,816,567 issued Mar. 28, 1989.

In a preferred embodiment, the immunoglobulin sequences used in the construction of the immunoadhesins of the present invention are from an IgG immunoglobulin heavy chain constant domain. For human immunoadhesins, the use of human IgG1 and IgG3 immunoglobulin sequences is preferred. A major advantage of using IgG1 is that IgG1 immunoadhesins can be purified efficiently on immobilized protein A. In contrast, purification of IgG3 requires protein G, a significantly less versatile medium. However, other structural and functional properties of immunoglobulins should be considered when choosing the Ig fusion partner for a particular immunoadhesin construction. For example, the IgG3 hinge is longer and more flexible, so it can accommodate larger adhesin domains that may not fold or function properly when fused to IgG1. Another consideration may be valency; IgG immunoadhesins are bivalent homodimers, whereas Ig subtypes like IgA and IgM may give rise to dimeric or pentameric structures, respectively, of the basic Ig homodimer unit. For NTNRα immunoadhesins designed for in vivo application, the pharmacokinetic properties and the effector functions specified by the Fc region are important as well. Although IgG1, IgG2 and IgG4 all have in vivo half-lives of 21 days, their relative potencies at activating the complement system are different. IgG4 does not activate complement, and IgG2 is significantly weaker at complement activation than IgG1. Moreover, unlike IgG1, IgG2 does not bind to Fc receptors on mononuclear cells or neutrophils. While IgG3 is optimal for complement activation, its in vivo half-life is approximately one third of the other IgG isotypes. Another important consideration for immunoadhesins designed to be used as human therapeutics is the number of allotypic variants of the particular isotype. In general, IgG isotypes with fewer serologically-defined allotypes are preferred. For example, IgG1 has only four serologically-defined allotypic sites, two of which (G1m and 2) are located in the Fc region; and one ofthese sites G1m1, is non-immunogenic. In contrast, there are 12 serologically-defined allotypes in IgG3, all of which are in the Fc region; only three of these sites (G3m5, 11 and 21) have one allotype which is nonimmunogenic. Thus, the potential immunogenicity of a γ3 immunoadhesin is greater than that of a γ1 immunoadhesin.

With respect to the parental immunoglobulin, a useful joining point is just upstream of the cysteines of the hinge that form the disulfide bonds between the two heavy chains. In a frequently used design, the codon for the C-terminal residue of the NTNRα part of the molecule is placed directly upstream of the codons for the sequence DKTHTCPPCP of the IgG1 hinge region.

The general methods suitable for the construction and expression of immunoadhesins are the same as those disclosed hereinabove with regard to NTNRα. NTNRα immunoadhesins are most conveniently constructed by fusing the cDNA sequence encoding the NTNRα portion in-frame to an Ig cDNA sequence. However, fusion to genomic Ig fragments can also be used (see, e.g., Gascoigne et al., *Proc. Natl. Acad. Sci. USA*, 84:2936–2940(1987); Aruffo et al., *Cell*, 61:1303–1313 (1990); Stamenkovic et al., *Cell*, 66:1133–1144(1991)). The latter type of fusion requires the presence of Ig regulatory sequences for expression. cDNAs encoding IgG heavy-chain constant regions can be isolated based on published sequence from cDNA libraries derived from spleen or peripheral blood lymphocytes, by hybridization or by polymerase chain reaction (PCR) techniques. The cDNAs encoding the NTNRα and Ig parts of the immunoadhesin are inserted in tandem into a plasmid vector that directs efficient expression in the chosen host cells. For expression in mammalian cells, pRK5-based vectors (Schall et al., *Cell*, 61:361–370(1990)) and CDM8-based vectors (Seed, *Nature*, 329:840(1989)) can be used. The exact junction can be created by removing the extra sequences between the designed junction codons using oligonucleotide-directed deletional mutagenesis (Zoller et al., *Nucleic Acids Res.*, 10:6487 (1982); Capon et al., *Nature*, 337:525–531 (1989)). Synthetic oligonucleotides can be used, in which each half is complementary to the sequence on either side of the desired junction; ideally, these are 36 to 48-mers. Alternatively, PCR techniques can be used to join the two parts of the molecule in-frame with an appropriate vector.

The choice of host cell line for the expression of NTNRα immunoadhesins depends mainly on the expression vector. Another consideration is the amount of protein that is required. Milligram quantities often can be produced by transient transfections. For example, the adenovirus EIA-transformed 293 human embryonic kidney cell line can be transfected transiently with pRK5-based vectors by a modification of the calcium phosphate method to allow efficient immunoadhesin expression. CDM8-based vectors can be used to transfect COS cells by the DEAE-dextran method (Aruffo et al., *Cell*, 61:1303–1313 (1990); Zettmeissl et al., *DNA Cell Biol. US*, 9:347–353 (1990)). If larger amounts of protein are desired, the immunoadhesin can be expressed after stable transfection of a host cell line. For example, a pRK5-based vector can be introduced into Chinese hamster ovary (CHO) cells in the presence of an additional plasmid encoding dihydrofolate reductase (DHFR) and conferring resistance to G418. Clones resistant to G418 can be selected in culture; these clones are grown in the presence of increasing levels of DHFR inhibitor methotrexate; clones are selected, in which the number of gene copies encoding the DHFR and immunoadhesin sequences is co-amplified. If the immunoadhesin contains a hydrophobic leader sequence at its N-terminus, it is likely to be processed and secreted by the transfected cells. The expression of immunoadhesins with more complex structures may require uniquely suited host cells; for example, components such as light chain or J chain may be provided by certain myeloma or hybridoma cell hosts (Gascoigne et al., 1987, supra, Martin et al., *J. Virol.*, 67:3561–3568 (1993)).

Immunoadhesins can be conveniently purified by affinity chromatography. The suitability of protein A as an affinity ligand depends on the species and isotype of the immunoglobulin Fc domain that is used in the chimera. Protein A can be used to purify immunoadhesins that are based on human γ1, γ2, or γ4 heavy chains (Lindmark et al., *J. Immunol. Meth.*, 62:1–13 (1983)). Protein G is recommended for all mouse isotypes and for human γ3 (Guss et al., *EMBO J.*, 5:1567–1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. The conditions for binding an immunoadhesin to the protein A or G affinity column are dictated entirely by the characteristics of the Fc domain; that is, its species and isotype. Generally, when the proper ligand is chosen, efficient binding occurs directly from unconditioned culture fluid. One distinguishing feature of immunoadhesins is that, for human γ1 molecules, the binding capacity for protein A is somewhat diminished relative to an antibody of the same Fc type. Bound immunoadhesin can be efficiently eluted either at acidic pH (at or above 3.0), or in a neutral pH buffer containing a mildly chaotropic salt. This affinity chromatography step can result in an immunoadhesin preparation that is >95% pure.

Other methods known in the art can be used in place of, or in addition to, affinity chromatography on protein A or G to purify immunoadhesins. Immunoadhesins behave similarly to antibodies in thiophilic gel chromatography (Hutchens et al., *Anal. Biochem.*, 159:217–226 (1986)) and immobilized metal chelate chromatography (Al-Mashikhi et al., *J. Dairy Sci.*, 71:1756–1763 (1988)). In contrast to antibodies, however, their behavior on ion exchange columns is dictated not only by their isoelectric points, but also by a charge dipole that may exist in the molecules due to their chimeric nature.

If desired, the immunoadhesins can be made bispecific. Thus, the immunoadhesins of the present invention may combine a NTNRα extracellular domain and a domain, such as the extracellular domain, of another cytokine or neurotrophic factor receptor subunit. Exemplary cytokine receptors from which such bispecific immunoadhesin molecules can be made include TPO (or mpl ligand), EPO, G-CSF, IL-4, IL-7, GH, PRL, IL-3, GM-CSF, IL-5, IL-6, LIF, OSM, CNTF, GDNF and IL-2 receptors. For bispecific molecules, trimeric molecules, composed of a chimeric antibody heavy chain in one arm and a chimeric antibody heavy chain-light chain pair in the other arm of their antibody-like structure are advantageous, due to ease of purification. In contrast to antibody-producing quadromas traditionally used for the production of bispecific immunoadhesins, which produce a mixture of ten tetramers, cells transfected with nucleic acid encoding the three chains of a trimeric immunoadhesin structure produce a mixture of only three molecules, and purification of the desired product from this mixture is correspondingly easier.

The NTNRα protein and NTNRα gene are believed to find ex vivo or in vivo therapeutic use for administration to a mammal, particularly humans, in the treatment of diseases or disorders, related to neurturin activity or benefited by neurturin-responsiveness. See Kotzbauer et al *Nature* 384:467–470 (1996), which is specifically incorporated herein by reference. Conditions particularly amenable to treatment with the embodiments of the invention are those related to Ret expression or that benefit by Ret activation, particularly of the downstream pathways mediated by Ret See Treanor et al. *Nature* 382:80–83 (1996); Jing et al. *Cell* 85:1113–1124 (1996); Trupp et al. *Nature* 381:785–789 (1996); and Durbec et al. *Nature* 381:789–793 (1996), which are specifically incorporated herein by reference. Particularly preferred are neurologic disorders, preferably central nervous system disorders, disorders of the kidney, hematopoietic disorders related to the spleen, and enteric nervous system disorders. The patient is administered an effective amount of NTNRα protein, peptide fragment, or variant of the invention. Therapeutic methods comprising administering NTNRα, NTNRα agonists (e.g. NTN), NTNRα antagonists (which compete with and bind endogenous NTN but fail to activate Ret), or anti-NTNRα antibodies are within the scope of the present invention. The present invention also provides for pharmaceutical compositions comprising NTNRα protein, peptide fragment, or derivative in a suitable pharmacologic carrier. The NTNRα protein, peptide fragment, or variant may be administered systemically or locally. Applicable to the methods taught herein, the receptor protein can be optionally administered prior to, after, or preferably concomitantly with (or in complex with) NTN or other NTNRα ligand. As taught herein, NTNRα can be provided to target cells in the absence of NTN to increase the responsiveness of those cells to subsequently administered NTN or NTN agonist.

Certain conditions can benefit from an increase in NTN (or other NTNRα-ligand) responsiveness. It may therefore be beneficial to increase the number of or binding afftnity of NTNRα in cells of patients suffering from such conditions. This can be achieved through administration of soluble NTNRα, optionally complexed with NTNRα-ligand, preferably NTN, or by gene therapy using NTNRα-encoding nucleic acid. Selective expression of recombinant NTNRα in appropriate cells could be achieved using NTNRα genes controlled by tissue specific or inducible promoters or by producing localized infection with replication defective viruses carrying a recombinant NTNRα gene. Conditions which may benefit from increased sensitivity to NTN include, but are not limited to, motoneuron disorders including amyotrophic lateral sclerosis, Werdnig-Hoffmann disease, chronic proximal spinal muscular atrophy, and Guillain-Barre syndrome. Additional conditions include those involving sympathetic neurons, particularly where increased survival or NTN-responsiveness is desired. Conditions where increased survival or NTN-responsiveness of sensory neurons, including peripheral sensory neurons, and central nervous system neurons, including dopaminergic neurons, is desirable are also suitably treated with embodiments of the invention. Accordingly, treatment of neurological disorders associated with diabetes, Parkinson's disease, Alzheimer's disease, and Huntington's chorea are provided herein. NTN finds particular use in treatment of Parkinson's disease. The present methods can also be applied to conditions related to non-neuronal cells that express NTNRα. In fact, since NTNRα serves to activate Ret, conditions associated with Ret-expressing cells can be treated with the embodiments of the invention.

A disease or medical disorder is considered to be nerve damage if the survival or function of nerve cells and/or their axonal processes is compromised. Such nerve damage occurs as the result conditions including (a) Physical injury, which causes the degeneration of the axonal processes and/or nerve cell bodies near the site of the injury; (b) Ischemia, as a stroke; (c) Exposure to neurotoxins, such as the cancer and AIDS chemotherapeutic agents such as cisplatin and dideoxycytidine (ddC), respectively; (d) Chronic metabolic diseases, such as diabetes or renal dysfunction; and (e) Neurodegenerative diseases such as Parkinson's disease, Alzheimer's disease, and Amyotrophic Lateral Sclerosis (ALS), which cause the degeneration of specific neuronal populations. Conditions involving nerve damage include Parkinson's disease, Alzheimer's disease, Amyotrophic Lateral Sclerosis, stroke, diabetic polyneuropathy, toxic neuropathy, and physical damage to the nervous system such as that caused by physical injury of the brain and spinal cord or crush or cut injuries to the arm and hand or other parts of the body, including temporary or permanent cessation of blood flow to parts of the nervous system, as in stroke.

The NTNRα gene is expressed in muscle cells and associated neurons. Accordingly, the present invention provides for methods of treating muscle cell disorders comprising administering to a patient in need of such treatment the compounds of the invention. Muscle cell disorders which may benefit from such treatment include but are not limited to the following progressive muscular dystrophies: Duchenne, Becker, Emery-Dreifuss, Landouzy-Dejerine, scapulohumeral, limb-girdle, Von Graefe-Fuchs, oculopharyngeal, myotonic and congenital. In addition, such molecules may be of use in the treatment of congenital (central core, nemaline, centronuclear and congenital fiber-type disproportion) and acquired (toxic, inflammatory) myopathies. The present invention further provides for a method of treating a muscle cell disorder comprising administering to the patient an effective amount of NTNRα protein or an active portion thereof.

In a further embodiment of the invention, patients that suffer from an excess of NTNR, hypersensitivity to NTN, excess NTN, etc. may be treated by administering an effective amount of anti-sense RNA or anti-sense oligodeoxyribonucleotides corresponding to the NTNRα gene coding region thereby decreasing expression of NTNR.

The compounds and methods of the invention may have use in conditions associated with a decrease in hematopoietic cells. Examples of these diseases include: anemia (including macrocytic and aplastic anemia); thrombocytopenia; hypoplasia; disseminated intravascular coagulation (DIC); myelodysplasia; immune (autoimmune) thrombocytopenic purpura (ITP), and HIV induced ITP. Additionally, these NTNRα molecules may be useful in treating myeloproliferative thrombocytotic diseases as well as thrombocytosis from inflammatory conditions and in iron deficiency. NTNRα polypeptide and NTNRα gene which lead to an increase in hematopoietic cell proliferation may also be used to enhance repopulation of mature blood cell lineages in cells having undergone chemo- or radiation therapy or bone marrow transplantation therapy. Generally, the NTNRα molecules are expected to lead to an enhancement of the proliferation and/or differentiation (but especially proliferation) of hematopoietic cells. Preferred embodiments provide for treatment to enhance hematopoiesis occurring in the spleen.

Other potential therapeutic applications for NTNRα and NTNRα gene include treatment to promote kidney or liver cell growth, survival, and repair. For example, acute renal failure refers to the abrupt disruption of previously normal kidney function. This serious clinical condition is due to a wide variety of mechanisms including circulatory failure (shock), vascular blockage, glomerulonephritis, and obstruction to urine flow. Acute renal failure frequently arises as a complication of abdominal or vascular surgery. Also, low birth weight, high-risk neonates may now survive lung and heart problems due to continued improvements in prenatal care, only to die from complications of acute renal failure caused by infection or drug toxicity. Of particular clinical importance are cases of acute renal failure associated with trauma, sepsis, postoperative complications, or medication, particularly antibiotics. In particular, the compounds of the invention find use in etiologies, directly or indirectly, related to dysfunction of the enteric nervous system or renal system. Specific conditions affecting the GI include but are not limited to Achalasia, Esophageal spasm, Scleroderma (related to muscular atrophy of the smooth muscle portion of the esophagus, weakness of contraction of the lower two-thirds of the esophageal body, and incompetence of the lower esophageal sphincter, but also caused by treatment with immunosuppressive agents), disorders such as duodenal ulcer, Zollinger-Ellison Syndrome (hypersecretion of acid caused by factors including genetic factors, smoking, neural influences), hypersecretion of gastric acid, malabsorptive disorder for example, in diabetes (and hypoparathyroidism, hyperthyroidism, and adrenal insufficiency) where gastric atony, nausea, vomiting, etc. are at least in part related to dysfunction of the sympathetic/parasympathetic nervous system. Additional disorders include disorders of intestinal motility, including: Diverticulosis/diverticulitis; Hirschsprung's disease (a congenital disorder caused by absence of ganglion cells (Meissner's and Auerbach's plexuses) in a small segment of the distal colon, usually near the anus, typically presented in infants, but in less severe cases, may not be diagnosed until adolescence or early adulthood; Megacolon of other types (Hirschsprung's is a type of megacolon); Intestinal pseudo-obstruction, acute or chronic, which is a severe dysmotility due to abnormalities of sympathetic innervation of the muscle layers of the intestine, or secondarily may result from scleroderma, diabetes, amyloidosis, other neurologic diseases, drugs, or sepsis; chronic constipation, which is a serious problem in patients with mental retardation or neurological diseases, wherein a contributing factor is disordered gut motility. Also include are treatments for kidney diseases and disorders. Additional conditions include but not limited to: Spinal cord dysfunction, due to an obvious disruption of enteric nervous system; Guillain Barre syndrome; Multiple sclerosis; Pandysautonomia (dysfunction of autonomic nervous system); Parkinsonism (frequently associated with disordered gastrointestinal motility); Multiple System Atrophy (Shy Drager Syndrome), which has been documented to have as a feature disordered gut motility; and porphyria and amyloidosis which are diffuse diseases manifested by neuropathy and often with accompanying GI motility disorders.

The necrosis or damage of NTNR-expressing or NTN-responsive tissue includes a necrosis due to microbiologic infection such as vital hepatitis, tuberculosis, typhoid fever, tularemia, brucellosis, yellow fever, and the like, or necrosis due to ischemic injury resulting from shock, heart failure, and the like, or necrosis due to acute or chronic reaction with drugs and toxic substances such as chloroform, carbon tetrachloride, phosphorous poisoning, and the like. As taught herein cellular growth enhancement, including renal cells such as renal epithelial cells and neuron innervating the kidney, is useful in treating kidney disease. The compounds and methods of the present invention provide for the repair of kidney damage. Not to be bound by theory, it is believed that this can be accomplished, either directly or indirectly, by stimulating kidney cells, including innervating neurons, to grow and divide. Accordingly, a method for regenerating kidney tissue is provided that includes the steps of preparing a NTNRα agonist (e.g. soluble NTNRα optionally complexed with NTN) as disclosed herein, optionally in combination with a pharmacologically acceptable carrier or additional growth factor or cytokine, and contacting the kidney tissue with the composition. A therapeutic amount of the composition is administered. Localized injections or implants are a preferred delivery method. Alternatively, damaged kidneys could be removed, treated ex vivo, and returned to the host after the kidney is repaired.

NTNRα agonists, including NTN, can be administered during hemodialysis. Hemodialysis is defined as the temporary removal of blood from a patient for the purpose of extracting or separating toxins therefrom and the return of the cleansed blood to the same patient. Hemodialysis is indicated in patients where renal impairment or failure exists, that is, in cases where the blood is not being properly or sufficiently cleansed, (particularly to remove water) by the kidneys. In the case of chronic renal impairment or failure, hemodialysis has to be carried out on a repetitive basis For example, in end stage kidney disease where transplantation of kidneys is not possible or for medical reasons is contra-indicated, the patient will have to be dialyzed about 100 to 150 times per year. This can result in several thousand accesses to the blood stream to enable the active hemodialysis to be performed over the remaining life of the patient.

The invention finds use in some immunosuppressive therapies where there is the side-effect of kidney damage. For example, therapy of IDDM in humans by methods designed to suppress the autoimmune response. Therapy utilizing cyclosporin A in diabetes can result in kidney damage. The invention finds use in disorders or conditions that can result in kidney damage. For example, diabetes can result in the typical late damages of blood vessels of the kidneys. Other examples include immunologically- or non-immunologically-caused kidney diseases, such as e.g. glomerulonephritis, acute kidney failure, transplant rejection and kidney damage caused by nephrotic substances, kidney transplants, toxic damage to the kidneys. Furthermore, the present invention finds use in organ transplantation, including organ transport for storing any organ enucleated from a donor to insure the protection of the organ at the time of its transplantation, minimizing any trouble occurring until the transplantation operation, and to ensure the preservation of said organ in a good condition. A prefereed organ is one having NTNR-bearing or NTN-responsive cells. In one specific embodiment the organ is the kidney. Use or intervention with NTNRα agonist, including NTN, promises success with regard to the maintenance of the kidney function.

As discussed herein, an object of the invention to provide methods for treatment of mammals with dysfunctional gastrointestinal muscle or disorders of smooth muscles elsewhere in the body. The gastrointestinal muscle is organized and regulated very differently than muscle elsewhere. Both skeletal and smooth muscle in the gastrointestinal tract are under the control of the enteric nervous system which is an extremely complex network of nerves and muscles, that resides within the gastrointestinal wall and orchestrates the entire digestive process including motility, secretion and absorption. The enteric nerves are also organized into interconnected networks called plexuses. Of these, the myenteric plexus, situated between the circular and longitudinal muscle layers, is the main modulator of gastrointestinal motility. It receives input from both the central nervous system (via vagal and sympathetic pathways) as well as from local reflex pathways. Its output consists of both inhibitory and excitatory signals to the adjacent muscle. The final neural pathway regulating muscle activity in the gastrointestinal tract is therefore represented by the neurons of the myenteric plexus. A useful, if somewhat simplistic concept is to visualize net muscle tone in the gastrointestinal tract as that resulting from the balance between the opposing effects of two neuronal systems in the myenteric plexus: one causing the muscle to contract (mainly via acetylcholine) and the other causing it to relax. Both types of neurons, however, are activated by acetylcholine within the myenteric plexus. The role of acetylcholine in the regulation of gastrointestinal muscle tone is therefore complex. Acetylcholine directly released by effector nerves near the muscle causes contraction; however, within the plexus, it may result in inhibition or excitation. This is in contrast to skeletal muscle outside the gastrointestinal tract which is directly innervated by nerves emanating from the central nervous system. The interaction between nerve and muscle in skeletal muscle outside the gastrointestinal tract is far more simple: nerves release acetylcholine which causes the muscle to contract. Finally, the myenteric plexus is probably the most important but not the only determinant of muscle tone in the gastrointestinal tract. In fact, basal smooth muscle tone may be visualized as resulting from the sum of many different factors including intrinsic (myogenic) tone, and circulating hormones, in addition to nerve activity. It should be clear therefore, that the regulation of gastrointestinal tract muscle motility is far more complex than that of skeletal muscle outside the gastrointestinal tract. While there have been isolated reports on the effects of botulinum toxin on in vitro preparations of gastrointestinal smooth muscle, the regulation of gastrointestinal muscle is so complex that the physiological consequences of blocking neurotransmitter release (by using toxin such as botulinum) in humans or in live animals were not predictable prior to the present invention. The present invention provides compositions, methods, and devices for treatment of gastrointestinal disorders including achalasia, other disorders of the lower esophageal sphincter, sphincter of Oddi dysfunction, irritable bowel syndrome, and others disorders as discussed herein.

For example, provided is a method to treat Irritable Bowel Syndrome (IBS), which is a motor disorder consisting of altered bowel habits, abdominal pain, and the absence of detectable pathology. IBS is recognized by its symptoms, which are markedly influenced by psychological factors and stressful life situations. IBS is one of the most commonly encountered gastrointestinal disorders. Between 20% and 50% of patients referred to gastrointestinal clinics suffer from IBS. Symptoms of IBS occur in approximately 14% of otherwise apparently healthy people. It is a syndrome composed of a number of conditions with similar manifestations. The major symptoms of IBS (altered bowel habits, abdominal pain and bloating) are manifestations of increased motility in the gut and hyper-secretion of gastric acid. Activity of the GI tract is modulated neurally by the central nervous system (CNS) via parasympathetic and sympathetic innervation and by the peripherally located enteric nervous system (ENS) which resides within the GI tract itself.

In another aspect is provided the administration of NTNRα to a mammal having depressed levels of endogenous NTNRα or a defective NTNRα gene, preferably in the situation where such depressed levels lead to a pathological disorder, or where there is lack of activation of the NTNRα and Ret. In these embodiments where the full length NTNRα is to be administered to the patient, it is contemplated that the gene encoding the receptor may be administered to the patient via gene therapy technology.

In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA*, 83:4143–4146 (1986)). The oligonucleotides can be modified to enhance their uptake, e.g., by substituting their negatively charged phosphodiester groups by uncharged groups.

There are a variety of techniques available for introducing nucleic acids into viable cells. The techniques vary depending upon whether the nucleic acid is transferred into cultured cells in vitro, ex vivo, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al, *Trends in Biotechnology,* 11:205–210(1993)). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., *J. Biol. Chem.,* 262:4429–4432(1987); and Wagner et al., *Proc. Natl. Acad. Sci. USA,* 87:3410–3414(1990). For review of the currently known gene marking and gene therapy protocols see Anderson et al, *Science,* 256:808–813 (1992).

The invention also provides antagonists of NTNRα activation (e.g., NTNRα antisense nucleic acid, neutralizing antibodies). Administration of NTNRα antagonist to a mammal having increased or excessive levels of endogenous NTNRα activation is contemplated, preferably in the situation where such increased levels of NTNRα or Ret activation lead to a pathological disorder.

In one embodiment, NTNRα antagonist molecules may be used to bind endogenous ligand in the body, thereby causing desensitized NTNRα to become responsive to NTN ligand, especially when the levels of NTN ligand in the serum exceed normal physiological levels. Also, it may be beneficial to bind endogenous NTN ligand which is activating undesired cellular responses (such as proliferation of tumor cells).

Pharmaceutical compositions of the soluble NTNRα can further include a NTN or other NTNRα agonist. Such dual compositions may be beneficial where it is therapeutically useful to prolong half-life of NTN, provide a slow-release reservoir for NTN, activate endogenous NTNRα or Ret, and/or to supplement the lack of NTNRα in a target Ret-expressing cell, thereby rendering the cell responsive to NTN.

Therapeutic formulations of NTNRα are prepared for storage by mixing NTNRα having the desired degree of purity with optional physiologically acceptable carriers, excipients, or stabilizers (*Remington's Pharmaceutical Sciences*, 16th edition, Osol, A., Ed., (1980)), in the form of lyophilized cake or aqueous solutions. Acceptable carriers, excipients, or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counter-ions such as sodium; and/or non-ionic surfactants such as Tween, Pluronics or polyethylene glycol (PEG).

The NTNRα also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles, and nanocapsules), or in macroemulsions. Such techniques are disclosed in *Remington's Pharmaceutical Sciences*, supra.

NTNRα to be used for in vivo administration must be sterile. This is readily accomplished by filtration through sterile filtration membranes, prior to or following lyophilization and reconstitution. NTNRα ordinarily will be stored in lyophilized form or in solution.

Therapeutic NTNRα compositions generally are placed into a container having a sterile access port, for example, an intravenous solution bag or vial having a stopper pierceable by a hypodermic injection needle.

The route of NTNRα administration is in accord with known methods, e.g., those routes set forth above for specific indications, as well as the general routes of injection or infusion by intravenous, intraperitoneal, intracerebral, intramuscular, intraocular, intraarterial, or intralesional means, or sustained release systems as noted below. NTNRα is administered continuously by infusion or by bolus injection. Generally, where the disorder permits, one should formulate and dose the NTNRα for site-specific delivery. Administration can be continuous or periodic. Administration can be accomplished by a constant- or programmable-flow implantable pump or by periodic injections.

Suitable examples of sustained-release preparations include semipermeable matrices of solid hydrophobic polymers containing the protein, which matrices are in the form of shaped articles, e.g., films, or microcapsules. Examples of sustained-release matrices include polyesters, hydrogels (e.g., poly(2-hydroxyethyl-methacrylate) as described by Langer et al., *J. Biomed. Mater. Res.*, 15:167–277 (1981) and Langer, *Chem. Tech.*, 12:98–105 (1982) or poly (vinylalcohol)), polylactides (U.S. Pat. No. 3,773,919, EP 58,481), copolymers of L-glutamic acid and γ ethyl-L-glutamate (Sidman et al., *Biopolymers*, 22:547–556 (1983)), non-degradable ethylene-vinyl acetate (Langer et al., supra), degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release NTNRα compositions also include liposomally entrapped NTNRα. Liposomes containing NTNRα are prepared by methods known per se: DE 3,218, 121; Epstein et al., *Proc. Natl. Acad Sci USA*, 4,82:3688–3692(1985); Hwang et al., *Proc. Natl. Acad. Sci. USA*, 77:4030–4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200–800 Angstroms) unilamellar type in which the lipid content is greater than about 30 mol. % cholesterol, the selected proportion being adjusted for the optimal NTNRα therapy.

When applied topically, the NTNRα is suitably combined with other ingredients, such as carriers and/or adjuvants. There are no limitations on the nature of such other ingredients, except that they must be physiologically acceptable and efficacious for their intended administration, and cannot degrade the activity of the active ingredients of the composition. Examples of suitable vehicles include ointments, creams, gels, or suspensions, with or without purified collagen. The compositions also may be impregnated into transdermal patches, plasters, and bandages, preferably in liquid or semi-liquid form.

For obtaining a gel formulation, the NTNRα formulated in a liquid composition may be mixed with an effective amount of a water-soluble polysaccharide or synthetic polymer such as PEG to form a gel of the proper viscosity to be applied topically. The polysaccharide that may be used includes, for example, cellulose derivatives such as etherified cellulose derivatives, including alkyl celluloses, hydroxyalkyl celluloses, and alkylhydroxyalkyl celluloses, for example, methylcellulose, hydroxyethyl cellulose, carboxymethyl cellulose, hydroxypropyl methylcellulose, and hydroxypropyl cellulose; starch and fractionated starch; agar, alginic acid and alginates; gum arabic; pullullan; agarose; carrageenan; dextrans; dextrins; fructans; inulin; mannans; xylans; arabinans; chitosans; glycogens; glucans; and synthetic biopolymers; as well as gums such as xanthan gum; guar gum; locust bean gum; gum arabic; tragacanth gum; and karaya gum; and derivatives and mixtures thereof. The preferred gelling agent herein is one that is inert to biological systems, nontoxic, simple to prepare, and not too runny or viscous, and will not destabilize the NTNRα held within it.

Preferably the polysaccharide is an etheri fed cellulose derivative, more preferably one that is well defined, purified, and listed in USP, e.g., methylcellulose and the hydroxyalkyl cellulose derivatives, such as hydroxypropyl cellulose, hydroxyethyl cellulose, and hydroxypropyl methylcellulose. Most preferred herein is methylcellulose.

The polyethylene glycol useful for gelling is typically a mixture of low and high molecular weight PEGs to obtain the proper viscosity. For example, a mixture of a PEG of molecular weight 400–600 with one of molecular weight 1500 would be effective for this purpose when mixed in the proper ratio to obtain a paste.

The term "water soluble" as applied to the polysaccharides and PEGs is meant to include colloidal solutions and dispersions. In general, the solubility of the cellulose derivatives is determined by the degree of substitution of ether groups, and the stabilizing derivatives useful herein should have a sufficient quantity of such ether groups per anhydroglucose unit in the cellulose chain to render the derivatives water soluble. A degree of ether substitution of at least 0.35 ether groups per anhydroglucose unit is generally sufficient. Additionally, the cellulose derivatives may be in the form of alkali metal salts, for example, the Li, Na, K, or Cs salts.

If methylcellulose is employed in the gel, preferably it comprises about 2–5%, more preferably about 3%, of the gel and the NTNRα is present in an amount of about 300–1000 mg per ml of gel.

Semipermeable, implantable membrane devices are useful as means for delivering drugs in certain circumstances. For example, cells that secrete soluble NTNRα or chimeras can be encapsulated, and such devices can be implanted into a patient. For example, into the brain of patients suffering from Parkinson's Disease. See, U.S. Pat. No. 4,892,538 of Aebischer et al.; U.S. Pat. No. 5,011,472 of Aebischer et al.; U.S. Pat. No. 5,106,627 of Aebischer et al.; PCT Application WO 91/10425; PCT Application WO 91/10470; Winn et al., *Exper. Neurology*, 11 3:322–329 (1991); Aebischer et al., Exper. Neurology, 111:269–275 (1991); and Tresco et al., *ASAIO*, 38:17–23 (1992). Accordingly, also included is a method for preventing or treating damage to a nerve or damage to other NTNR-expressing or NTN-responsive cells, e.g. kidney, as taught herein, which comprises implanting cells that secrete NTNRα, its agonists or antagonists as may be required for the particular condition, into the body of patients in need thereof. Finally, the present invention includes a device for preventing or treating nerve damage or damage to other cells as taught herein by implantation into a patient comprising a semipermeable membrane, and a cell that secretes NTNRα (or its agonists or antagonists as may be required for the particular condition) encapsulated within said membrane and said membrane being permeable to NTNRα (or its agonists or antagonists) and impermeable to factors from the patient detrimental to the cells. The patient's own cells, transformed to produce NTN or NTNRα ex vivo, could be implanted directly into the patient, optionally without such encapsulation. The methodology for the membrane encapsulation of living cells is familiar to those of ordinary skill in the art, and the preparation of the encapsulated cells and their implantation in patients may be accomplished without under experimentation.

The present invention includes, therefore, a method for preventing or treating nerve damage by implanting cells, into the body of a patient in need thereof, cells either selected for their natural ability to generate NTNRα or engineered to secrete NTNRα. Preferably, the secreted NTNRα being soluble, human mature NTNRα when the patient is human. The implants are preferably non-immunogenic and/or prevent immunugenic implanted cells from being recognized by the immune system. For CNS delivery, a preferred location for the implant is the cerebral spinal fluid of the spinal cord.

An effective amount of NTNRα to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. Typically, the clinician will administer the NTNRα until a dosage is reached that achieves the desired effect. A typical daily dosage for systemic treatment might range from about 1 μg/kg to up to 10 mg/kg or more, depending on the factors mentioned above. As an alternative general proposition, the NTNRα is formulated and delivered to the target site or tissue at a dosage capable of establishing in the tissue a NTNRα level greater than about 0.1 ng/cc up to a maximum dose that is efficacious but not unduly toxic. This intra-tissue concentration should be maintained if possible by continuous infusion, sustained release, topical application, NTNRα-expressing cell implant, or injection at empirically determined frequencies. The progress of this therapy is easily monitored by conventional assays. When administered in complex with or concomitantly with NTN, a 100:1 to 1:100 ratio of NTNRα to NTN dimer is useful. Preferably the ratio is 10:1 to 1:10, more preferably 1:1, and even more preferably 2:1, which may reflect the natural binding ratio of NTNRα to NTN. An amount of NTN effective to produce the desired result is administered. A typical daily dosage for systemic treatment might also range from about 1 μg/kg to up to 10 mg/kg or more, depending on the factors mentioned above.

NTNRα nucleic acid is useful for the preparation of NTNRα polypeptide by recombinant techniques exemplified herein which can then be used for production of anti-NTNRα antibodies having various utilities described below.

The NTNRα (polypeptide or nucleic acid) can be used to increase NTN-responsiveness (and thus increase cell survival and modulate Ret-mediated downstream pathways) of cells in vitro. Such cells must contain or be modified to contain cell surface Ret. Cultured ex vivo, these cells may simultaneously be exposed to other known neurotrophic factors or cytokines, such as those described herein.

In yet another aspect of the invention, the NTNRα may be used for affinity purification of ligands that bind to the NTNRα, either naturally-occurring or synthetic ligands. NTN is a preferred ligand for purification. Briefly, this technique involves: (a) contacting a source of NTN ligand with an immobilized NTNRα under conditions whereby the NTN ligand to be purified is selectively adsorbed onto the immobilized receptor, (b) washing the immobilized NTNRα and its support to remove non-adsorbed material; and (c) eluting the NTN ligand molecules from the immobilized NTNRα to which they are adsorbed with an elution buffer. In a particularly preferred embodiment of affinity purification, NTNRα is covalently attaching to an inert and porous matrix or resin (e.g., agarose reacted with cyanogen bromide). Especially preferred is a NTNRα immunoadhesin immobilized on a protein A column. A solution containing NTN ligand is then passed through the chromatographic material. The NTN ligand adsorbs to the column and is subsequently released by changing the elution conditions (e.g. by changing pH or ionic strength). Novel ligands can be detected by monitoring displacement of a known, labelled NTNRα ligand, such as $I^{125}$- or biotinylated-NTN.

The NTNRα may be used for competitive screening of potential agonists or antagonists for binding to the NTNRα. Such agonists or antagonists may constitute potential therapeutics for treating conditions characterized by insufficient or excessive NTNRα activation, respectively.

The preferred technique for identifying molecules which bind to the NTNRα utilizes a chimeric receptor (e.g., epitope-tagged NTNRα or NTNRα immunoadhesin) attached to a solid phase, such as the well of an assay plate. The binding of the candidate molecules, which are optionally labelled (e.g., radiolabeled), to the immobilized receptor can be measured. Alternatively, competition for binding of a known, labelled NTNRα ligand, such as $I^{125}$-NTN, can be measured. For screening for antagonists, the NTNRα can be exposed to a NTN ligand followed by the putative antagonist, or the NTN ligand and antagonist can be added to the NTNRα simultaneously, and the ability of the antagonist to block receptor activation can be evaluated.

The present invention also provides for assay systems for detecting NTN activity, comprising cells which express high levels of NTNRα, and which are, therefore, extremely sensitive to even very low concentrations of NTN or NTN-like molecules. The present invention provides for assay systems in which NTN activity or activities similar to NTN activity resulting from exposure to a peptide or non-peptide compound may be detected by measuring a physiological response to NTN in a cell or cell line responsive to NTN which expresses the NTNRα molecules of the invention. A physiological response may comprise any of the biological effects of NTN, including but not limited to, those described herein, as well as the transcriptional activation of certain nucleic acid sequences (e.g. promoter/enhancer elements as well as structural genes), NTN-related processing, translation, or phosphorylation, the induction of secondary processes in response to processes directly or indirectly induced by NTN, including Ret-mediated effects, and morphological changes, such as neurite sprouting, or the ability to support the survival of cells, for example, nodose or dorsal root ganglion cells, motoneurons, dopaminergic neurons, sensory neurons, Purkinje cells, or hippocampal neurons In one embodiment of the invention, the functional interaction between NTN and the NTNRα may be observed by detecting an increase in the production autophosphorylated Ret protein, or alternatively, phosphorylated ERK-1 or ERK-2 homologs (See Kotzbauer et al., supra).

The present invention provides for the development of novel assay systems which can be utilized in the screening of compounds for NTN- or NTN-like activity. Target cells which bind NTN may be produced by transfection with NTNRα-encoding nucleic acid or may be identified and segregated by, for example, fluorescent-activated cell sorting, sedimentation of rosettes, or limiting dilution. Once target cell lines are produced or identified, it may be desirable to select for cells which are exceptionally sensitive to NTN. Such target cells may bear a greater number of NTNRα molecules; target cells bearing a relative abundance of NTNRα can be identified by selecting target cells which bind to high levels of NTN, for example, by marking high-expressors with fluorophore tagged-NTN followed by immunofluorescence detection and cell sorting. Alternatively, cells which are exceptionally sensitive to NTN may exhibit a relatively strong biological response in response to NTN binding, such as a sharp increase in Ret-mediated effects or in immediate early gene products such as c-fos or c-jun. By developing assay systems using target cells which are extremely sensitive to NTN, the present invention provides for methods of screening for NTN or NTN-like activity which are capable of detecting low levels of NTN activity.

In particular, using recombinant DNA techniques, the present invention provides for NTN target cells which are engineered to be highly sensitive to NTN. For example, the NTN-receptor gene can be inserted into cells which are naturally NTN responsive such that the recombinant NTNRα gene is expressed at high levels and the resulting engineered target cells express a high number of NTNRs on their cell surface. Alternatively, or additionally, the target cells may be engineered to comprise a recombinant gene which is expressed at high levels in response to NTN/receptor binding. Such a recombinant gene may preferably be associated with a readily detectable product. For example, and not by way of limitation, transcriptional control regions (i.e. promoter/enhancer regions) from an immediate early gene may be used to control the expression of a reporter gene in a construct which may be introduced into target cells. The immediate early gene/reporter gene construct, when expressed at high levels in target cells by virtue of a strong promoter/enhancer or high copy number, may be used to produce an amplified response to NTNRα binding. For example, and not by way of limitation, a NTN-responsive promoter may be used to control the expression of detectable reporter genes including β-galactosidase, growth hormone, chloramphenicol acetyl transferase, neomycin phosphotransferase, luciferase, or β-glucuronidase. Detection of the products of these reporter genes, well known to one skilled in the art, may serve as a sensitive indicator for NTN or NTN-like activity of pharmaceutical compounds.

The NTNRα-encoding or reporter gene constructs discussed herein (e.g., soluble ECD) can be inserted into target cells using any method known in the art, including but not limited to transfection, electroporation, calcium phosphate/DEAE dextran methods, and cell gun. The constructs and engineered target cells can be used for the production of transgenic animals bearing the above-mentioned constructs as transgenes, from which NTNRα-expressing target cells may be selected using the methods discussed.

Nucleic acids which encode NTNR, preferably from non-human species, such as murine or rat protein, can be used to generate either transgenic animals or "knock out" animals which, in turn, are useful in the development and screening of therapeutically useful reagents. A transgenic animal (e.g., a mouse) is an animal having cells that contain a transgene, which transgene was introduced into the animal or an ancestor of the animal at a prenatal, e.g., an embryonic, stage. A taansgene is a DNA which is integrated into the genome of a cell from which a transgenic animal develops. In one embodiment, the human and /or rat cDNA encoding NTNRα, or an appropriate sequence thereof, can be used to clone genomic DNA encoding NTNRα in accordance with established techniques and the genomic sequences used to generate transgenic animals that contain cells which express DNA encoding NTNR. Methods for generating transgenic animals, particularly animals such as mice, have become conventional in the art and are described, for example, in U.S. Pat. Nos. 4,736,866 and 4,870,009. Typically, particular cells would be targeted for NTNRα transgene incorporation with tissue-specific enhancers, which could result in desired effect of treatment. Transgenic animals that include a copy of a transgene encoding NTNRα introduced into the germ line of the animal at an embryonic stage can be used to examine the effect of increased expression of DNA encoding NTNR. Such animals can be used as tester animals for reagents thought to confer protection from, for example, diseases related to NTN. In accordance with this facet of the invention, an animal is treated with the reagent and a reduced incidence of the disease, compared to untreated animals bearing the transgene, would indicate a potential therapeutic intervention for the disease.

Transgenic mice bearing minigenes are currently preferred. First a fusion enzyme expression construct is created and selected based on expression in cell culture as described in the Examples. Then a minigene capable of expressing that fusion enzyme is constructed using known techniques. Particularly preferred hosts are those bearing minigene constructs comprising a transcriptional regulatory element that is tissue-specific for expression.

Transgenic mice expressing NTNRα minigene are made using known techniques, involving, for example, retrieval of fertilized ova, microinjection of the DNA construct into male pronuclei, and re-insertion of the fertilized transgenic ova into the uteri of hormonally manipulated pseudopregnant foster mothers. Alternatively, chimeras are made using known techniques employing, for example, embryonic stem cells (Rossant et al., *Philos. Trans. R. Soc. Lond. Biol.* 339:207–215 (1993)) or primordial germ cells (Vick et al. *Philos. Trans. R. Soc. Lond. Biol.* 251:179–182 (1993)) of the host species. Insertion of the transgene can be evaluated by Southern blotting of DNA prepared from the tails of offspring mice. Such transgenic mice are then back-crossed to yield homozygotes.

It is now well-established that transgenes are expressed more efficiently if they contain introns at the 5' end, and if these are the naturally occurring introns (Brinster et al. *Proc. Natl. Acad. Sci. USA* 85:836 (1988); Yokode et al., *Science* 250:1273 (1990)).

Transgenic mice expressing NTNRα minigene are created using established procedures for creating transgenic mice. Transgenic mice are constructed using now standard methods (et al *Proc. Natl. Acad. Sci. USA* 85:836 (1988); Yokode et al., *Science* 250:1273 (1990); Rubin et al., *Proc Natl Acad Sci USA* 88:434 (1991); Rubin et al. *Nature* 353:265 (1991)). Fertilized eggs from timed matings are harvested from the oviduct by gentle rinsing with PBS and are microinjected with up to 100 nanoliters of a DNA solution, delivering about $10^4$ DNA molecules into the male pronucleus. Successfully injected eggs are then re-implanted into pseudopregnant foster mothers by oviduct transfer. Less than 5% of microinjected eggs yield transgenic offspring and only about ⅓ of these actively express the transgene: this number is presumably influenced by the site at which the transgene enters the genome.

Transgenic offspring are identified by demonstrating incorporation of the microinjected transgene into their genomes, preferably by preparing DNA from short sections of tail and analyzing by Southern blotting for presence of the transgene ("Tail Blots"). A preferred probe is a segment of a minigene fusion construct that is uniquely present in the transgene and not in the mouse genome. Alternatively, substitution of a natural sequence of codons in the transgene with a different sequence that still encodes the same peptide yields a unique region identifiable in DNA and RNA analysis. Transgenic "founder" mice identified in this fashion are bred with normal mice to yield heterozygotes, which are back-crossed to create a line of transgenic mice. Tail blots of each mouse from each generation are examined until the strain is established and homozygous. Each successfully created founder mouse and its strain vary from other strains in the location and copy number of transgenes inserted into the mouse genome, and hence have widely varying levels of transgene expression. Selected animals from each established line are sacrificed at 2 months of age and the expression of the transgene is analyzed by Northern blotting of RNA from liver, muscle, fat, kidney, brain, lung, heart, spleen, gonad, adrenal and intestine.

Alternatively, the non-human homologs of NTNRα can be used to construct a NTNRα "knock out" animal, i.e., having a defective or altered gene encoding NTNR, as a result of homologous recombination between the endogenous NTNRα gene and an altered genomic NTNRα DNA introduced into an embryonic cell of the animal. For example, murine NTNRα cDNA can be used to clone genomic NTNRα DNA in accordance with established techniques. A portion of the genomic NTNRα DNA (e.g., such as an exon which encodes e.g., an extracellular domain) can be deleted or replaced with another gene, such as a gene encoding a selectable marker which can be used to monitor integration. Typically, several kilobases of unaltered flanking DNA (both at the 5' and 3' ends) are included in the vector (see e.g., Thomas and Capecchi, *Cell* 51:503 (1987) for a description of homologous recombination vectors). The vector is introduced into an embryonic stem cell line (e.g., by electroporation) and cells in which the introduced DNA has homologously recombined with the endogenous DNA are selected (see e.g., Li et al., *Cell* 69: 915 (1992)). The selected cells are then injected into a blastocyst of an animal (e.g., a mouse) to form aggregation chimeras (see e.g., Bradley, in Teratocarcinomas and Embryonic Stem Cells: A Practical Approach, E. J. Robertson, ed. (IRL, Oxford, 1987), pp. 113–152). A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for their ability to accept grafts, reject tumors and defend against infectious diseases and can be used in the study of basic immunobiology.

In addition to the above procedures, which can be used for preparing recombinant DNA molecules and transformed host animals in accordance with the practices of this invention, other known techniques and modifications thereof can be used in carrying out the practice of the invention. For example, U.S. Pat. No. 4,736,866 discloses vectors and methods for production of a transgenic non-human eukaryotic animal whose germ cells and somatic cells contain a gene sequence introduced into the animal, or an ancestor of the animal, at an embryonic stage. U.S. Pat. No. 5,087,571 discloses a method of providing a cell culture comprising (1) providing a transgenic non-human mammal, all of whose germ cells and somatic cells contain a recombinant gene sequence introduced at an embryonic stage; and (2) culturing one or more of said somatic cells. U.S. Pat. No. 5,175,385 discloses vectors and methods for production of a transgenic mouse whose somatic and germ cells contain and express a gene at sufficient levels to provide the desired phenotype in the mouse, the gene having been introduced into said mouse or an ancestor of said mouse at an embryonic stage, preferably by microinjection. A partially constitutive promoter, the metallothionein promoter, was used to drive heterologous gene expression. U.S. Pat. No. 5,175,384 discloses a method of introducing a transgene into an embryo by infecting the embryo with a retrovirus containing the transgene. U.S. Pat. No. 5,175,383 discloses DNA constructs having a gene, homologous to the host cell, operably linked to a heterologous and inducible promoter effective for the expression of the gene in the urogenital tissues of a mouse, the transgene being introduced into the mouse at an embryonic stage to produce a transgenic mouse. Even though a homologous gene is introduced, the gene can integrate into a chromosome of the mouse at a site different from the location of the endogenous coding sequence. The vital MMTV promoter was disclosed as a suitable inducible promoter. U.S. Pat. No. 5,162,215 discloses methods and vectors for transfer of genes in avian species, including livestock species such as chickens, turkeys, quails or ducks, utilizing pluripotent stem cells of embryos to produce transgenic animals. U.S. Pat. No. 5,082,779 discloses pituitary-specific expression promoters for use in producing transgenic animals capable of tissue-specific expression of a gene. U.S. Pat. No. 5,075,229 discloses vectors and methods to produce transgenic, chimeric animals whose hemopoietic liver cells contain and express a functional gene driven by a liver-specific promoter, by injecting into the peritoneal cavity of a host fetus the disclosed vectors such that the vector integrates into the genome of fetal hemopoietic liver cells.

Although some of the above-mentioned patents and publications are directed to the production or use of a particular gene product or material that are not within the scope of the present invention, the procedures described therein can easily be modified to the practice of the invention described in this specification by those skilled in the art of fermentation and genetic engineering.

Assay systems of the present invention enable the efficient screening of pharmaceutical compounds for use in the treatment of NTN-associated diseases. For example, and not by way of limitation, it may be desirable to screen a pharmaceutical agent for NTN activity and therapeutic efficacy in cerebellar degeneration. In a one embodiment of the invention, cells responsive to NTN may be identified and isolated, and then cultured in microwells in a multiwell culture plate. Culture medium with added test agent, or added NTN, in numerous dilutions may be added to the wells, together with suitable controls. The cells may then be examined for improved survival, neurite sprouting, and the like, and the activity of test agent and NTN, as well as their relative activities, can be determined. For example, one can now identify NTN-like compounds which can, like NTN, prevent motoneuron cell death in response to toxic assault or axotomy, for example. NTN responsive motoneurons could be utilized in assay systems to identify compounds useful in treating motoneuron diseases. If a particular disease is found to be associated with a defective NTN response in a particular tissue, a rational treatment for the disease would be supplying the patient with exogenous NTN. However, it may be desirable to develop molecules which have a longer half-life than endogenous NTN, or which act as NTN agonists, or which are targeted to a particular tissue. Accordingly, the methods of the invention can be used to produce efficient and sensitive screening systems which can be used to identify molecules with the desired properties. Similar assay systems could be used to identify NTN antagonists.

In addition, the present invention provides for experimental model systems for studying the physiological role of NTN and its receptor. Such systems include animal models, such as (i) animals exposed to circulating NTNRα peptides which compete with cellular receptor for NTN binding and thereby produce a NTN-depleted condition, (ii) animals immunized with NTNR; (iii) transgenic animals which express high levels of NTNRα and therefore are hypersensitive to NTN; and (iv) animals derived using embryonic stem cell technology in which the endogenous NTNRα genes were deleted from the genome.

The present invention also provides for experimental model systems for studying the physiological role of NTN and its receptor. In these model systems. NTNRα protein, peptide fragment, or a derivative thereof, may be either supplied to the system or produced within the system. Such model systems could be used to study the effects of NTN excess or NTN depletion. The experimental model systems may be used to study the effects of increased or decreased response to NTN in cell or tissue cultures, in whole animals, in particular cells or tissues within whole animals or tissue culture systems, or over specified time intervals (including during embryogenesis) in embodiments in which NTNRα expression is controlled by an inducible or developmentally regulated promoter. In a particular embodiment of the invention, the CMV promoter may be used to control expression of NTNRα in transgenic animals. Transgenic animals, as discussed herein, are produced by any method known in the art, including, but not limited to microinjection, cell fusion, transfection, and electroporation.

The present invention also provides for model systems for autoimmune disease in which an autoimmune response is directed toward NTNRα. Such models comprise animals which have been immunized with immunogenic amounts of NTNRα and preferably found to produce anti-NTNRα antibodies and/or cell-mediated immunity. To produce such a model system, it may be desirable to administer the NTNRα in conjunction with an immune adjuvant.

For example, and not by way of limitation, an experimental model system may be created which may be used to study the effects of excess NTN activity. In such a system, the response to NTN may be increased by engineering an increased number of NTNRs on cells of the model system relative to cells which have not been so engineered. These cells should also express Ret or another signalling molecule capable of interacting with NTNRα and mediating an NTN signal. It may be preferable to provide an increased number of NTNRs selectively on cells which normally express NTNRs. Cells may be engineered to produce increased numbers of NTNRα by infection with a virus which carries a NTNRα gene of the invention. Alternatively, the NTNRα gene may be provided to the cells by transfection. If the model system is an animal, a recombinant NTNRα gene may be introduced into the cells of the animal by infection with a virus which carries the NTNRα gene or other means as discussed herein. For example, a transgenic animal may be created which carries the NTNRα gene as a transgene. In order to ensure expression of NTNR, the NTNRα gene should be placed under the control of a suitable promoter sequence. It may be desirable to put the NTNRα gene under the control of a constitutive and/or tissue specific promoter. By increasing the number of cellular NTNRs, the response to endogenous NTN may be increased. If the model system contains little or no NTN, NTN may be added to the system. It may also be desirable to add additional NTN to the model system in order to evaluate the effects of excess NTN activity. Over expressing NTN (or secreted NTN) may be the preferable method for studying the effects of elevated levels of NTN on cells already expressing NTNR. More preferably would be to express NTNRα in all cells (general expression) and determine which cells are then endowed with functional responsiveness to NTN, thus allowing the potential identification of a second receptor component, if one exists.

An experimental model system may be created which may be used to study the effects of diminished NTN activity.

This system may permit identification of processes or neurons which require NTN, and which may represent potential therapeutic targets. In such a system, the response to NTN may be decreased by providing recombinant NTNRs which are not associated with a cell surface or which are engineered so as to be ineffective in transducing a response to NTN. For example, NTNRα protein, peptide, or derivative may be supplied to the system such that the supplied receptor may compete with endogenous NTNRα for NTN binding, thereby diminishing the response to NTN. The NTNRα may be a cell free receptor which is either added to the system or produced by the system. For example, a NTNRα protein which lacks the transmembrane domain may be produced by cells within the system, such as an anchorless NTNRα that may be secreted from the producing cell. Alternatively, NTNRα protein, peptide or derivative may be added to an extracellular space within the system. In additional embodiments of the invention, a recombinant NTNRα gene may be used to inactivate or "knock out" the endogenous gene by homologous recombination, and thus create a NTNRα deficient cell, tissue, or animal. For example, and not by way of limitation, a recombinant NTNRα gene may be engineered to contain an insertional mutation, for example the neo gene, which inactivates NTNR. Such a construct, under the control of a suitable promoter, may be introduced into a cell, such as an embryonic stem cell, by a technique such as transfection, transduction, injection, etc. Cells containing the construct may then be selected by G418 resistance. Cells which lack an intact NTNRα gene may then be identified, e.g. by Southern blotting or Northern blotting or assay of expression. Cells lacking an intact NTNRα gene may then be fused to early embryo cells to generate transgenic animals deficient in NTNR. A comparison of such an animal with an animal not expressing endogenous NTN would reveal that either the two phenotypes match completely or that they do not, implying the presence of additional NTN-like factors or receptors. Such an animal may be used to define specific cell populations, e.g., neuronal populations, or any other in vivo processes, normally dependent upon NTN or its receptor. Thus, these populations or processes may be expected to be effected if the animal did not express NTNRα and therefore could not respond to NTN. Alternatively, a recombinant NTNRα protein, peptide, or derivative which competes with endogenous receptor for NTN may be expressed on the surface of cells within the system, but may be engineered so as to fail to transduce a response to NTN binding. The recombinant NTNRα proteins, peptides or derivatives described above may bind to NTN with an affinity that is similar to or different from the affinity of endogenous NTNRα to NTN. To more effectively diminish the response to NTN, the NTNRα protein, peptide, or derivative may desirably bind to NTN with a greater affinity than that exhibited by the native receptor. If the NTNRα protein, peptide, or derivative is produced within the model system, nucleic acid encoding the NTNRα protein, peptide, or derivative may be supplied to the system by infection, transduction, transfection, etc. or as a transgene. As discussed supra, the NTNRα gene may be placed under the control of a suitable promoter, which may be, for example, a tissue-specific promoter or an inducible promoter or developmentally regulated promoter. In a specific embodiment of the invention the endogenous NTNRα gene of a cell may be replaced by a mutant NTNRα gene by homologous recombination. In a further embodiment of the invention, NTNRα expression may be reduced by providing NTNRα expressing cells with an amount of NTNRα antisense RNA or DNA effective to reduce expression of NTNRα protein.

The polypeptides of the invention also find use as feed additives for animals. The nucleic acids of the invention find use in preparing these polypeptides.

The NTNRα polypeptides are also useful as molecular weight markers. To use a NTNRα polypeptide as a molecular weight marker, gel filtration chromatography or SDS-PAGE, for example, will be used to separate protein(s) for which it is desired to determine their molecular weight(s) in substantially the normal way. NTNRα, preferably a soluble NTNR, and other molecular weight markers will be used as standards to provide a range of molecular weights. For example, phosphorylase b (mw=97,400), bovine serum albumin (mw=68,000), ovalbumin (mw=46,000), trypsin inhibitor (mw=20,100), and lysozyme (mw=14,400) can be used as MW markers. The other molecular weight markers mentioned here can be purchased commercially from Amersham Corporation, Arlington Heights, Ill. The molecular weight markers are generally labeled to facilitate detection thereof. For example, the markers may be biotinylated and, following separation, can be incubated with streptavidin-horseradish peroxidase so that the various markers can be detected by light detection.

The purified NTNRα, and the nucleic acid encoding it, may also be sold as reagents for mechanism studies of NTNRα and its ligands, to study the role of the NTNRα and NTN ligand in normal growth and development, as well as abnormal growth and development, e.g., in malignancies. NTNRα probes can be used to identify cells and tissues which are responsive to NTN in normal or diseased states. For example, a patient suffering from a NTN-related disorder may exhibit an aberrancy of NTNRα expression. The present invention provides for methods for identifying cells which are responsive to NTN comprising detecting NTNRα expression in such cells. NTNRα expression may be evidenced by transcription of NTNRα mRNA or production of NTNRα protein. NTNRα expression may be detected using probes which identify NTNRα nucleic acid or protein. One variety of probe which may be used to detect NTNRα expression is a nucleic acid probe, which may be used to detect NTNR-encoding RNA by any method known in the art, including, but not limited to, in situ hybridization, Northern blot analysis, or PCR related techniques. Another variety of probe which may be used is tagged NTN as discussed herein.

According to the invention, tagged NTN may be incubated with cells under conditions which would promote the binding or attachment of NTN to said cells. In most cases, this may be achieved under standard culture conditions. For example, in one embodiment of the invention, cells may be incubated for about 30 minutes in the presence of tagged NTN. If the tag is an antibody molecule, it may be preferable to allow NTN to bind to cells first and subsequently wash cells to remove unbound ligand and then add anti-NTN antibody tag. In another embodiment of the invention, tagged NTN on the surface of NTN-responsive cells, hereafter called target cells, may be detected by resetting assays in which indicator cells that are capable of binding to the tag are incubated with cells bearing tagged-NTN such that they adhere to tagged-NTN on the target cells and the bound indicator cells form rosette-like clusters around NTN-tag bearing cells. These rosettes may be visualized by standard microscopic techniques on plated cells, or, alternatively, may allow separation of rosetted and non-rosetted cells by density centrifugation. In a preferred specific embodiment of the invention, target cells, such as neuronal cells. In alternative embodiments of the invention, tagged-NTN on the surface of target cells may be detected using immunofluorescent techniques in which a molecule which reacts with the tag, preferably an antibody, directly or indirectly produces fluorescent light The fluorescence may either be observed under a microscope or used to segregate tagged-NTN-bearing cells by fluorescence activated cell sorting techniques. The present invention also provides for methods for detecting other forms of tags, such as chromogenic tags and catalytic tags. An anti-NTNRα antibody can also be used as a probe. The detection methods for any particular tag will depend on the conditions necessary for producing a signal from the tag, but should be readily discernible by one skilled in the art.

NTNRα variants are useful as standards or controls in assays for the NTNRα for example ELISA, RIA, or RRA, provided that they are recognized by the analytical system employed, e.g., an anti-NTNRα antibody.

Polyclonal antibodies are generally raised in animals by multiple subcutaneous (sc) or intraperitoneal (ip) injections of the relevant antigen and an adjuvant. In that the preferred epitope is in the ECD of the NTNRα, it is desirable to use NTNRα ECD or a molecule comprising the ECD (e.g., NTNRα immunoadhesin) as the antigen for generation of polyclonal and monoclonal antibodies. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining 1 mg or 1 μg of the peptide or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, the monoclonal antibodies may be made using the hybridoma method first described by Kohler et al., Nature, 256:495 (1975), or may be made by recombinant DNA methods (Cabilly et al., supra).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp.59–103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, pp. 51–63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al, Anal. Biochem., 107:220 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

The ability of the MAbs to block binding of NTN to its receptor can be evaluated by ELISA and bioassay utilizing available reagents (rhNTNr-IgG; a stable transfected CHO cell line expressing. NTNRα). Neutralizing activities can also be evaluated by neuronal survival assay(s).

NTNR-specific MAbs can be developed as discussed above using for example, the receptor immunoadhesin and transfected cell line) to initiate new immunization protocols to generate NTNR-specific MAbs for use as potential agonists or antagonists, as well as for immunohistochemistry, immunocytochemistry, and assay development. The MAbs generated from fusion of the immunized animals can be screened for agonist and antagonist activities by bioassay (e.g., neuron survival assays, signal transduction/ phosphorylation, kidney cell survival assays) as well as by ELISA and FACS (functional blocking of NTN-NTNRα binding). Suitable techniques are provided in, for example, Lucas et al., *J. Immunol.* 145:1415–1422 (1990); Hoogenraad et al *J. Immunol. Methods* 6:317–320 (1983); Moks et al, *Eur. J. Biochem.* 85:1205–1210 (1986); Laemmli, *Nature* (London) 227:680–685 (1970); and, Towbin et al., *Proc Natl Acad Sci USA* 76:43504354 (1979).

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., *Curr. Opinion in Immunol.*, 5:256–262 (1993) and Plückthun, *Immunol. Revs.*, 130:151–188 (1992).

In a further embodiment, antibodies or antibody fragments can be isolated from antibody phage libraries generated using the techniques described in McCafferty et al., *Nature*, 348:552–554 (1990). Clackson etal., *Nature*, 352:624628 (1991) and Marks et al., *J Mol. Biol.*, 222:581–597(1991) describe the isolation of murine and human antibodies, respectively, using phage libraries. Subsequent publications describe the production of high affinity (nM range) human antibodies by chain shuffling (Mark et al., *Bio/Technoloy*, 10:779–783 (1992)), as well as combinatorial infection and in vivo recombination as a strategy for constructing very large phage libraries (Waterhouse et al., *Nuc. Acids. Res.*, 21:2265–2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (Cabilly et al., supra; Morrison, et al., *Proc. Nat. Acad Sci. USA*, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antiger-combining site of an antibody to create a chimeric bivalent antibody comprising one antigen-combining site having specificity for an antigen and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al, *Nature*, 321:522–525 (1986); Riechmann et al., *Nature*, 332:323–327 (1988); Verhoeyen et al., *Science*, 239:1534–1536 (1988)), by substituting rodent CDRs or CDR sequences for the corresponding sequences of a human antibody. Accordingly, such "humanized" antibodies are chimeric antibodies (Cabilly et al., supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.*, 151:2296(1993); Chothiaetal.,*J. Mol. Biol.*, 196:901 (1987)). Another method uses a particular framework derived from the consensus sequence of all human antibodies of a particular subgroup of light or heavy chains. The same framework may be used for several different humanized antibodies (Carter et al., *Proc. Nati. Acad Sci. USA*, 89:4285 (1992); Presta et al., *J. Immnol*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and gern-line mutant mice results in complete inhibition of endogenous antibody production. Transfer of the human germ-line immunogtobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al,*Nature*, 362:255–258 (1993); Bruggermann et al., *Year in Immuno.*, 7:33 (1993). Human antibodies can also be produced in phage-display libraries (Hoogenboom et al.,*J. Mol. Biol.*, 227:381 (1991); Marks et al.,*J. Mol. Biol.*, 222:581(1991)).

Bispecific antibodies (BsAbs) are antibodies that have binding specificities for at least two different antigens. BsAbs can be used as tumor targeting or imaging agents and can be used to target enzymes or toxins to a cell possessing the NTNRα. Such antibodies can be derived from full length antibodies or antibody fragments (e.g. F(ab')$_2$ bispecific antibodies). In accordance with the present invention, the BsAb may possess one arm which binds the NTNRα and another armn which binds to a cytokine or another cytokine receptor (or a subunit thereof) such as the receptors for TPO, EPO, G-CSF, IL-4, IL-7, GH, PRL; the α or β subunits of the IL-3, GM-CSF, IL-5, IL-6, LIF, OSM and CNTF receptors; or the α, β or γ subunits of the IL-2 receptor complex. For example, the BsAb may bind both NTNRα and gp130.

Methods for making bispecific antibodies are known in the art. Traditional production of full length bispecific antibodies is based on the coexpression of two immunoglobulin heavy chain-light chain pairs, where the two chains have different specificities (Millstein et al., *Nature*, 305:537–539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, published May 13, 1993, and in Traunecker et al., *EMBO J.*, 10:3655–3659 (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690 published Mar. 3, 1994. For further details of generating bispecific antibodies see, for example, Suresh et al., *Methods in Enzymology*, 121:210 (1986).

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. The following techniques can also be used for the production of bivalent antibody fragments which are not necessarily bispecific. According to these techniques, Fab'-SH fragments can be recovered from *E. coli*, which can be chemically coupled to form bivalent antibodies. Shalaby et al., *J Exp. Med.*, 175:217–225 (1992) describe the production of a fully humanized BsAb F(ab')$_2$ molecule. Each Fab' fragment was separately secreted from *E. coli* and subjected to directed chemical coupling in vitro to form the BsAb. The BsAb thus formed was able to bind to cells overexpressing the HER2 receptor and normal human T cells, as well as trigger the lytic activity of human cytotoxic lymphocytes against human breast tumor targets. See also Rodriguez et al., *Int. J. Cancers*, (Suppl.) 7:45–50 (1992).

Various techniques for making and isolating bivalent antibody fragments directly from recombinant cell culture have also been described. For example, bivalent heterodimers have been produced using leucine zippers. Kostelny et al., *J. Immunol.*, 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. The "diabody" technology described by Hollinger et al., *Proc. Natl. Acad. Sci. USA*, 90:6444–6448 (1993) has provided an alternative mechanism for making BsAb fragments. The fragments comprise a heavy-chain variable domain (VH) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making BsAb fragments by the use of single-chain Fv (sFv) dimers has also been reported. See Gruber et al., *J. Immunol.*, 152:5368 (1994).

The NTNRα agonists (including NTN) and agonist NTNRα antibodies of the present invention can be used to enhance splenic hematopoiesis, allowing some repopulation of blood cell lineages in patients having undergone chemo- or radiation therapy and transplantation. Generally, the antibodies will act to enhance proliferation and/or differentiation (but especially proliferation) of hematopoietic cells in the spleen. Without being bound by theory, NTNRα agonists may act directly as a growth, survival or differentiation factor for hematopoietic cells in the spleen and/or may indirectly act on the splenic stromal environment (possibly neurons involved in the splenic innervation) to produce another factor that is responsible for the maintenance of hematopoietic lineages. In any event, as taught herein NTNRα agonist, including NTN, have therapeutic benefit in facilitating the splenic engraftment of bone marrow transplants following irradiation or chemotherapy or for stimulating extramedullary hematopoiesis in the spleen (which is normal in rodents, but not normally seen in man) in those conditions where there is an increased demand for blood cell production due to anemia (red blood cells), chronic infection (neutrophils), bone marrow failure (all lineages), and immune deficiency (lymphocytes). The agonists may similarly be useful for treating diseases characterized by a decrease in blood cells. Examples of these diseases include: anemia (including macrocytic and aplastic anemia); thrombocytopenia; hypoplasia; immune (autoimmune) thrombocytopenic purpura (ITP); and HIV induced ITP. Also, the agonists may be used to treat a patient having suffered a hemorrhage.

Therapeutic applications for NTNRα neutralizing antibodies include the treatment of metabolic disorders and cell tumors at sites of NTNRα expression, especially those tumors characterized by overexpression of NTNRα.

For therapeutic applications, the NTNRα antibodies of the invention are administered to a mammal, preferably a human, in a physiologically acceptable dosage form, including those that may be administered to a human intravenously as a bolus or by continuous infusion over a period of time, by intramuscular, intraperitoneal, intra-cerebrospinal, subcutaneous, intra-articular, intrasynovial, intrathecal, oral, topical, or inhalation routes. The NTNRα antibodies also are suitably administered by intratumoral, peritumoral, intralesional, or perilesional routes or to the lymph, to exert local as well as systemic therapeutic effects.

Such dosage forms encompass physiologically acceptable carriers that are inherently non-toxic and non-therapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and PEG. Carriers for topical or gel-based forms of NTNRα antibodies include polysaccharides such as sodium carboxymethylcellulose or methylcellulose, polyvinylpyrrolidone, polyacrylates, polyoxyethylene-polyoxypropylene-block polymers, PEG, and wood wax alcohols. For all administrations, conventional depot forms are suitably used. Such forms include, for example, microcapsules, nano-capsules, liposomes, plasters, inhalation forms, nose sprays, sublingual tablets, and sustained-release preparations. The NTNRα antibody will typically be formulated in such vehicles at a concentration of about 0.1 mg/ml to 100 mg/ml.

Suitable examples of sustained-release preparations include semipermeable matrices of solid hydrophobic polymers containing the NTNRα antibody, which matrices are in the form of shaped articles, e.g. films, or microcapsules. Examples of sustained-release matrices include polyesters, hydrogels (for example, poly(2-hydroxyethyl-methacrylate) as described by Langer et al., supra and Langer, supra, or poly(vinylalcohol), polylactides (U.S. Pat. No. 3,773,919), copolymers of L-glutamic acid and γ ethyl-L-glutamate (Sidman et al., supra), non-degradable ethylene-vinyl acetate (Langer et al., supra), degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated NTNRα antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release NTNRα antibody compositions also include liposomally entrapped antibodies. Liposomes containing the NTNRα antibodies are prepared by methods known in the art, such as described in Epstein et al., *Proc. Natl. Acad. Sci. USA,* 82:3688 (1985); Hwang et al., *Proc. Natl. Acad. Sci. USA,* 77:4030 (1980); and U.S. Pat. Nos. 4,485,045 and 4,544,545. Ordinarily, the liposomes are the small (about 200–800 Angstroms) unilamellar type in which the lipid content is greater than about 30 mol. % cholesterol, the selected proportion being adjusted for the optimal NTNRα antibody therapy. Liposomes with enhanced circulation time are disclosed in U.S. Pat. No. 5,013,556.

For the prevention or treatment of disease, the appropriate dosage of NTNRα antibody will depend on the type of disease to be treated, as defined above, the severity and course of the disease, whether the antibodies are administered for preventive or therapeutic purposes, previous therapy, the patient's clinical history and response to the NTNRα antibody, and the discretion of the attending physician. The NTNRα antibody is suitably administered to the patient at one time or over a series of treatments.

Depending on the type and severity of the disease, about 1 μg/kg to 15 mg/kg of NTNRα antibody is an initial candidate dosage for administration to the patient, whether, for example, by one or more separate administrations, or by continuous infusion. A typical daily dosage might range from about 1 μg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

Animal model are available to assess effects of the compounds and method of the invention. For example, to assess the effects of treating damaged kidneys with compositions that affect growth (Toback, 1977; Toback et al. 1977), an intravenous injection of 1.0 to 1.1 mg of mercury per kg of body weight as HgC12 is given to rats to induce a reversible syndrome of acute nonoliguric acute renal failure. After one day, there are marked increases in serum urea nitrogen concentration (SUN), urinary excretion of sodium and protein, and necrosis of proximal tubular cells. By day two, increases in phospholipid, DNA and RNA synthesis, and mitotic index indicate that cellular regeneration is underway. By day three, the SUN reaches a maximum, and squamoid epithelial cells appear on the tubular basement membrane. At day five, the SUN returns to normal, the maximal rate of phospholipid synthesis is reached, and the tubules are repopulated with more mature cells. The effects of infusion of a composition of autocrine growth factors on renal structure is compared with untreated rats and animals infused with vehicle alone during the course of the mercuric chloride-induced acute tubular necrosis syndrome discussed above.

The NTNRα antibodies of the invention are also useful as affinity purification agents. In this process, the antibodies against NTNRα are immobilized on a suitable support, such a Sephadex resin or filter paper, using methods well known in the art. The immobilized antibody then is contacted with a sample containing the NTNRα to be purified, and thereafter the support is washed with a suitable solvent that will remove substantially all the material in the sample except the NTNRα, which is bound to the immobilized antibody. Finally, the support is washed with another suitable solvent, such as glycine buffer, pH 5.0, that will release the NTNRα from the antibody.

NTNRα antibodies may also be useful in diagnostic assays for NTNRα, e.g., detecting its expression in specific cells, tissues, or serum. For diagnostic applications, antibodies typically will be labeled with a detectable moiety. The detectable moiety can be any one which is capable of producing, either directly or indirectly, a detectable signal. For example, the detectable moiety may be a radioisotope, such as $^3$H, $^{14}$C, 32P, $^{35}$S, or $^{125}$I; a fluorescent or chemiluminescent compound, such as fluorescein isothiocyanate, rhodamine, or luciferin; radioactive isotopic labels, such as, e.g., $^{125}$I, $^{32}$P, $^{14}$C, or $^3$H; or an enzyme, such as alkaline phosphatase, beta-galactosidase, or horseradish peroxidase.

Any method known in the art for separately conjugating the polypeptide variant to the detectable moiety may be employed, including those methods described by Hunter et al., *Nature,* 144:945 (1962); David et al., *Biochemistry,* 13:1014 (1974); Pain et al., *J. Immunol. Meth.,* 40:219 (1981); and Nygren, *J. Histochem. and Cytochem.,* 30:407 (1982).

The antibodies of the present invention may be employed in any known assay method, such as competitive binding assays, direct and indirect sandwich assays, and immunoprecipitation assays. Zola, *Monoclonal Antibodies: A Manual of Techniques,* pp. 147–158 (CRC Press, Inc., 1987).

Competitive binding assays rely on the ability of a labeled standard to compete with the test sample analyte for binding with a limited amount of antibody. The amount of NTNRα in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

The following Examples of specific embodiments for carrying out the present invention are offered for illustrative purposes only, and are not intended to limit the scope of the present invention in any way.

The disclosures of all publications, patents and patent applications cited herein are hereby incorporated by reference in their entirety.

EXAMPLES

Example 1

Cloning of Human NTNRα

Eight partial human cDNAs (Genbank accession numbers: R02249 (SEQ ID NO.: 7), H12981 (SEQ ID NO.: 8), W73681 (SEQ ID NO.: 9), W73633 (SEQ ID NO.: 10), H05619 (SEQ ID NO.: 11), R02135 (SEQ ID NO.: 12), T03342 (SEQ ID NO.: 13), and HSC1KA111 (SEQ ID NO.: 14)) were identified as having similarity to the GDNF receptor α component (Jing et al. *Cell* 85:1113–1124 (1996); Treanor et al. *Nature* 382:80–83 (1996)), but were not identical to GDNFR sequences. A DNA sequence, determined by aligning these expressed-sequence-tag ("EST") cDNA sequences, was extended using 5' and 3' Marathon RACE reactions (Clonetech Inc.) on human spleen mRNA, using conditions supplied by the manufacturer, to obtain an initial set of human cDNA clones. Additional cDNA clones were identified by screening a human fetal brain cDNA library (Stratagene) using standard protocols. Lambda cDNA libraries were plated using standard protocols and a coding region probe, obtained by PCR amplification of the NTNRα gene using the 3' and 5' RACE information, was hybridized to the library. From an alignment of the cloned human cDNA sequences, a full length cDNA sequence was obtained (SEQ ID NO: 1), which was referred to as the human Neurturin receptor a ("hNTNRα") cDNA sequence. This sequence contained a open reading frame sequence (SEQ ID NO: 2) that encoded a single 464 amino acid protein sequence (SEQ ID NO: 3), which was designated human Neurturin receptor a ("hNTNRα").

Human NTNRα ("hNTNRα") displays an overall 47% similarity at the amino acid level to both hGDNFRα and rGDNFRα.

hNTNRα, like hGDNFRα, is an extracellular protein that is attached to the outer cell membrane via a glycosylphosphatidyl inositol ("GPI") modification. It has an amino terminal signal peptide for secretion, 3 potential glycosylation sites, and a stretch of 17 carboxy terminal hydrophobic amino acids preceded by a group of 3 small amino acids (Gly, Ser, Asn) defining a cleavage/binding site for GPI linkage (FIGS. 4A and 4B; Micanovic et al., *Proc. Natl. Acad. Sci. USA,* 87:157–161 (1990); Moran et al., *J. Biol. Chem.,* 266:1250–1257(1991)). The position of their 30 cysteine residues are completely conserved between NTNRα and GDNFRα (FIGS. 5A and 5B). The extracellular domain ("ECD") is flanked by the signal peptide and the GPI-attachment site.

Example 2

Cloning of Rat NTNRα ("rNTNRα")

Rat NTNRα ("rNTNRα") was cloned by-screening a rat brain cDNA library (Clonetech) using standard protocols. A full-length human NTNRα probe was hybridized to the rat cDN library at moderate stringency (e.g., 30% formamide at 42° C., wash in 0.1×SSC at 55° C.). The cDNA, having (SEQ ID NO: 4) and containing the complete open reading frame (SEQ ID NO: 5), was designated as rNTNRα cDNA. The open reading frame sequence encoded a single 464 amino acid protein sequence (SEQ ID NO: 6), which was designated rat Neurturin receptor a ("rNTNRα").

Rat NTNRα and human NTNRα display an overall 94% similarity at the amino acid level. At the DNA level, a 79% identity was observed. Rat NTNRα is 46% identical to both rat GDNFRα and human GDNFRα at the protein level. Rat NTNRα is 53% identical to rat GDNFRα at the DNA level.

rNTNRα, like rGDNFRα, hGDNFRα, and hNTNRα, is an extracellular protein that is attached to the outer cell membrane via a glycosyl-phosphatidyl inositol ("GPI") modification. It has an amino terminal signal peptide for secretion, 3 potential glycosylation sites, and a stretch of 17 carboxy terminal hydrophobic amino acids preceded by a group of 3 small amino acids (Gly, Ser, Asn) defining a cleavage/binding site for GPI linkage (FIGS. 4A and 4B). Surprisingly, the position of the 30 cysteine residues, which are conserved between human and rat GDNFRα, are conserved between human and rat NTNRα (FIGS. 5A and 5B). These cysteine residues are completely conserved between NTNTRα and GDNFRα (FIGS. 5A and 5B). The extracellular domain ("ECD") is flanked by the signal peptide and the GPI-attachment site.

Example 3
Vectors for Expression of Membrane-Bound and Soluble NTNRα

For mammalian protein expression the complete open reading frame of human NTNRα was amplified using PCR and cloned into a CMV based expression vector pRK5 or pRK7. The plasmid was designated pRK-hNTNRα for the human NTNR.

To make soluble forms rat and human NTNRα, both rat and human NTNRα-IgG expression construct were made by cloning the first 432 amino acids of each receptor (which lacks a GPI linkage site) in front of the human Fc sequence. For example, the NTNRα-IgG expression construct was made by cloning the first 432 amino acids of the receptor (which lacks a GPI linkage site) in front of the human Fc (IfF2a) sequence. Plasmids were designated pRK-hNTNRα-IgG for hNTNRα fusion and pRK-rNTNRα-IgG for rat NTNRα fusion. The human gene fusion coding nucleic acid sequence is SEQ ID NO: 15, which encodes the human fusion protein SEQ ID NO: 16. Suitable locations for attachment of structure to the ECD are within, or preferably C-terminal to, the CFTELTrNIIPG sequence of NTNRα ECD. The rat gene fusion coding nucleic acid sequence is SEQ ID NO: 17, which encodes the rat fusion protein SEQ ID NO: 18.

Example 4
Tissue Distribution of NTNRα

The tissue distribution of the NTNRα mRNA was examined using in situ hybridization analysis. Its distribution was compared to that of GDNFRα.

For in situ hybridization, E15.5 rat embryos were immersion-fixed overnight at 4° C. in 4% paraformaldehyde, then cryoprotected overnight in 15% sucrose. Adult rat brains and spinal cords were frozen fresh. All tissues were sectioned at 16 um, and processed for in situ hybridization using $^{33}$P-UTP labelled RNA probes as described (Davis et al. *Science* 259:1736–1739 (1993)) Sense and antisense probes were derived from the N-terminal region of GDNFRα using T7 polymerase. NTNRα RNA was detected with a probe, derived from hNTNRα, designated hNTNRα.T7insitu probe (SEQ ID NO: 19).

In the embryonic and adult rat nervous system, mRNA for NTNRα was found in the ventral midbrain, where dopaminergic neurons are located, in parts of the ventral spinal cord where motoneurons are located, and in the dorsal root ganglia (DRG) were sensory neurons reside. In addition, high levels of NTNRα transcripts were found in tissues such as the embryonic gut, bladder, cardiac conduction system and diaphragm. In the adult rat brain NTNRα was found mainly in the substantia nigra, cortex and olfactory bulb as well as in the dorsal horn of the spinal cord. Although NTNRα was occasionally found in tissues that express GDNFRα, the two transcripts were most often present adjacent to each other. For example, in the limb, GDNFRα is expressed in muscle cells, whereas NTNRα is found in the brachial plexus nerve which enervates the muscle. Likewise, in the embryonic bladder, NTNRα is expressed in the muscle layer, while GDNFRα is expressed in the underlying epithelia. Finally, in the gut NTNRα is expressed in the mucosal epithelium, while GDNFRα is expressed only in the adjacent smooth muscles. This pattern of expression is consistent with the notion that NTNRα mediates signals inside, as well as outside, the nervous system, and suggests distinct, complementary biological roles fbr NTNRα and GDNFRα.

Example 5
NTNRα Specifically Binds NTN

Figure 6B:
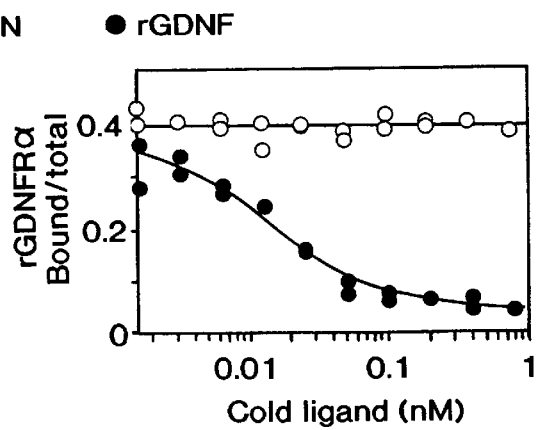
Figure 6C:
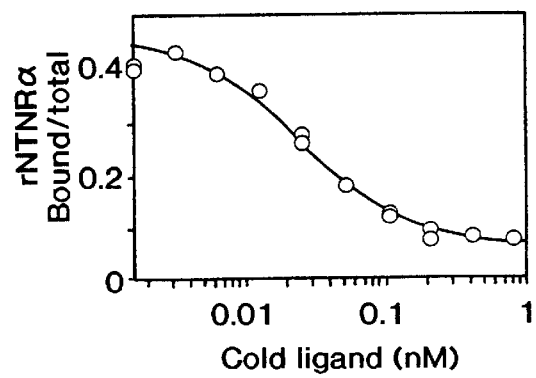
Figure 6D:
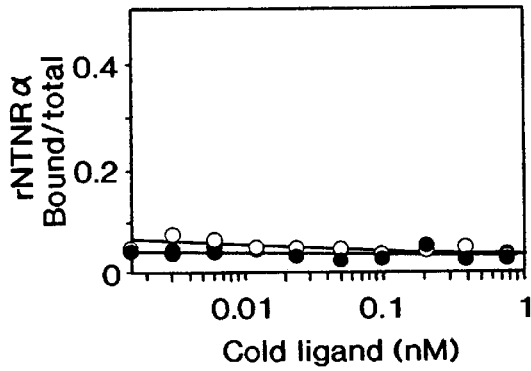
Figure 6E:
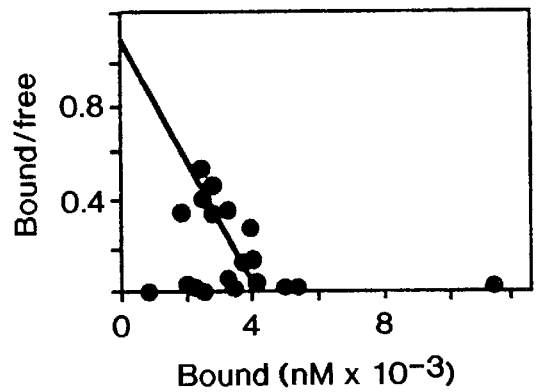
Figure 6F:
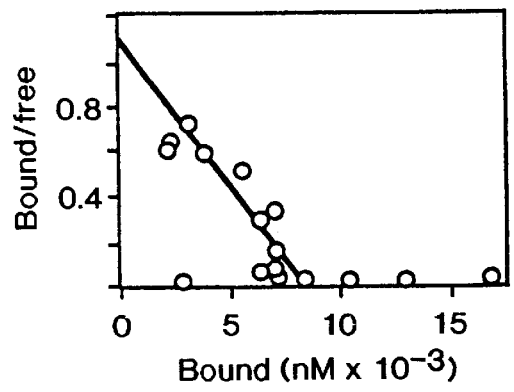

Equilibrium binding experiments were performed to determine the binding of NTNRα to NTN. Conditioned media from 293 cells transiently transfected with either the pRK-hNTNRα-IgG or pRK-rNTNRα-IgG constructs provided soluble receptor. The conditioned media was incubated with approximately 5 pM $^{125}$I human Neurturin, mouse Neurturin, or RGDNF along with different concentrations of the appropriate cold ligand in PBS containing 2 mg/ml BSA (Sigma) and 0.05% Brij 96 (Fluka) for 4 hours at room temperature. Ligand is in excess over the receptor. Receptor/ligand complexes were then incubated with protein A Sepharose CL-4B (Pharmacia) for an additional 1 hour at room temperature. After washing with PBS containing 0.2 mg/ml BSA, specific perceptible counts were measured. The IGOR program was used to determine Kd. It was found that both human and mouse $^{125}$I-NTN can bind to recombinant soluble human NTNRα (data not shown) or soluble rNTNRα protein, specifically and reversibly with an approximate $K_4$ of 10 pM (inset to FIG. 6F). In contrast neither human NTN (data not shown) nor mouse NTN were able to displace $^{125}$I-rGDNF from rGDNFRα (FIG. 6E), and no high affinity binding of human or mouse $^{125}$I-NTN to rGDNFRα was detected (FIG. 6A). Accordingly, NTN specifically binds NTNRα, interacting with high affinity with NTNRα but not with rGDNFRα. To further confirm that NTNRα is a specific receptor for NTN, competition binding experiments were performed using $^{125}$I-rGDNF. Displaceable high affinity binding of 125I-rGDNF to recombinant soluble rGDNFRα was readily observed ($K_d$ of 3 pM) (FIG. 6B inset); however, binding of $^{125}$I-rGDNF (iodinated either on tyrosine by the Bolton Hunter method or on lysine using lactoperoxidase) to either human or rat NTNRα was not detected. GDNF interacts at high affinity with GDNFRα but not with NTNRα. And, NTN specifically binds NTNRα. While no high affinity interaction between NTN and GDNFRα was detected, a low affinity interaction (Kd>1 nM) was observed when higher concentrations of unlabeled NTN (10 nm) displaced labelled rGDNF from GDNFRα.

Cell based equilibrium binding analysis, performed as described (Treanor et al. *Nature* 382:80–83 (1996)), confirmed the specificity of GDNFRα and NTNRα for GDNF and Neurturin, respectively. 293 cells, which were transiently transfected with either the full length NTNRα expression construct (or GDNFRα) or an irrelevant (control) construct, provided membrane-bound receptor. The observed specific associations between GDNF and GDNFRα and between NTN and NTNRα using competition binding to cells that express unmodified receptors were in agreement with the soluble receptor data (data not shown).

Figure 7A:
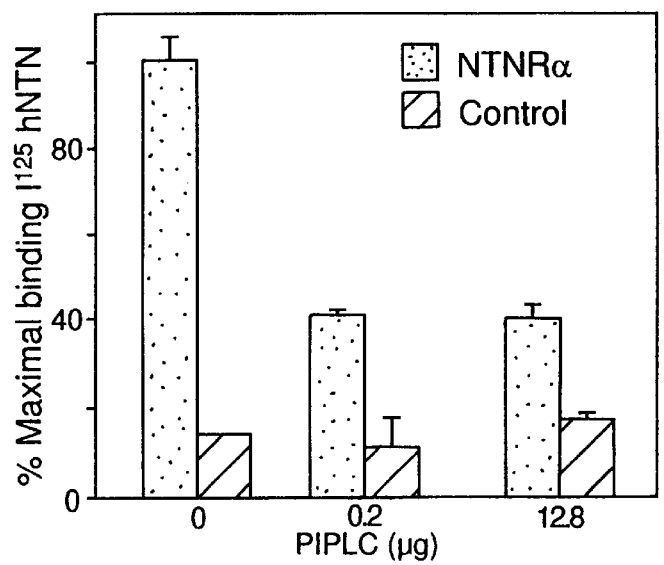
FIGS. 7A–7F depict interaction between NTN, NTNRα and Ret.

The ligand-binding effect of phosphoinositide-specific phospholipase C ("PIPLC") treatment of the membrane bound receptor was determined. PIPLC is an enzyme that specifically cleaves GPI linkage (Koke et al. *Prot. Express. Purification* 2:51–58 (1991); Shukla, *Life Sci.,* 10:1323–1335 (1982); Rhee et al., *Science,* 244:546–550 (1989)). 293 cells, which were transiently transfected with either the full length NTNRα expression construct or an irrelevant (control) construct, were incubated with ~20,000 cpm $^{125}$I human NTN in the presence of the indicated amounts of PIPLC for 90 minutes at room temperature (FIG. 7A). The cells were washed with ice-cold PBS containing 0.2 mg/ml BSA, after which cell associated $^{125}$I was measured. Consistent with the prediction that NTNRα is anchored to the cell surface by a GPI linkage, the binding of $^{125}$I-NTN to cells expressing NTNRα was significantly reduced following treatment with (FIG. 7A). Accordingly, NTNRα is a specific high affinity GPI-linked receptor for NTN.

Example 6
NTNRα Mediates Biological Response to NTN

Figure 7B:
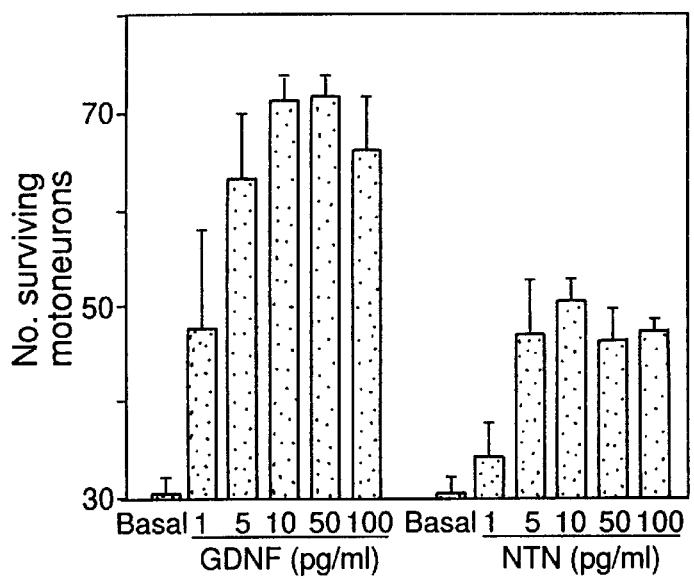

To confirm that NTNRα mediates the biological response to NTN, the effect of NTN on the survival of cells that express NTNRα was determined. For survival assays E14 rat motoneurons were isolated, plated, and grown in triplicate wells as described. After addition of the indicated growth factors, the number of surviving neurons was determined 72 hours later (FIG. 7B). It was observed that NTN can prevent the death of primary motoneurons (FIG. 7B) that express NTNRα (as determined by in situ hybridization). Moreover, in agreement with the finding that NTN and GDNF utilize distinct receptors, quantitative differences in the survival response of motoneurons to the two factors was detected: GDNF at saturating concentrations promoted the survival of 100% of the BDNF-responsive motoneurons; NTN, whose receptor is sparsely distributed in the embryonic ventral horn were motoneurons reside, prevented the death of only 50% of these cells (FIG. 7B). It was also observed that NTN can prevent the death of primary embryonic dopaminergic neurons that express NTNRα.

Figure 7C:
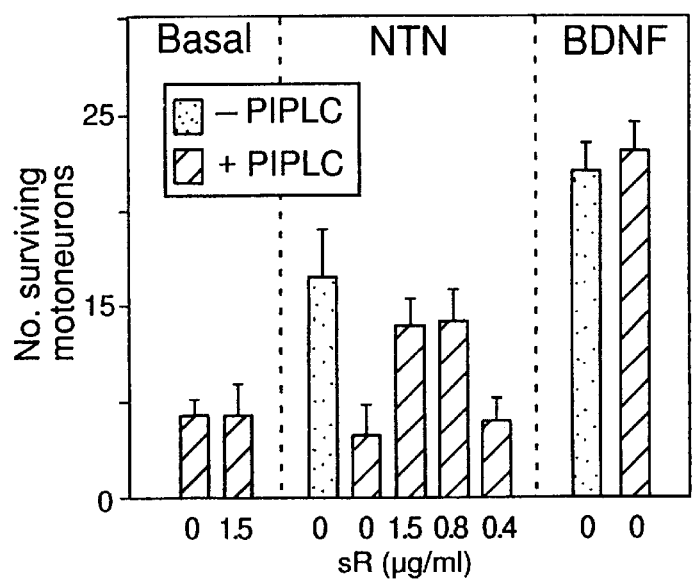

To further confirm that NTNRα is a required mediator of the NTN signal, embryonic motoneurons were treated with PIPLC and their survival in the presence of NTN or BDNF was monitored in culture. E14 rat motoneurons were isolated, plated, and grown in triplicate wells as described. PIPLC (2–4 ug/ml) was added to the indicated samples 1–2 h prior to, as well as 12 h and 24 h following, addition of the indicated growth factors, and the number of surviving neurons was determined 72 h later (FIG. 7C). The number of embryonic rat spinal motoneurons that remained alive at saturating concentrations of NTN was reduced by 70–90% following PIPLC treatment, whereas no decrease in the response of PIPLC-treated neurons to brain-derived neurotrophic factor (BDNF) was noted. Moreover, when NTN was added to these motoneurons in combination with soluble NTNRα (IgG fusion), the response to NTN was restored (FIG. 7C). Accordingly, NTNRα appears to be an essential component of the NTN signaling cascade and has the properties expected of the ligand-binding subunit of a functional NTN receptor. In addition, the soluble NTNRα receptor can impart a NTN-responsiveness to cells that lack cell surface NTNRα, but express the complementing Ret transmembrane protein.

Example 7
NTNRα Can Act Via Ret

Figure 7D:
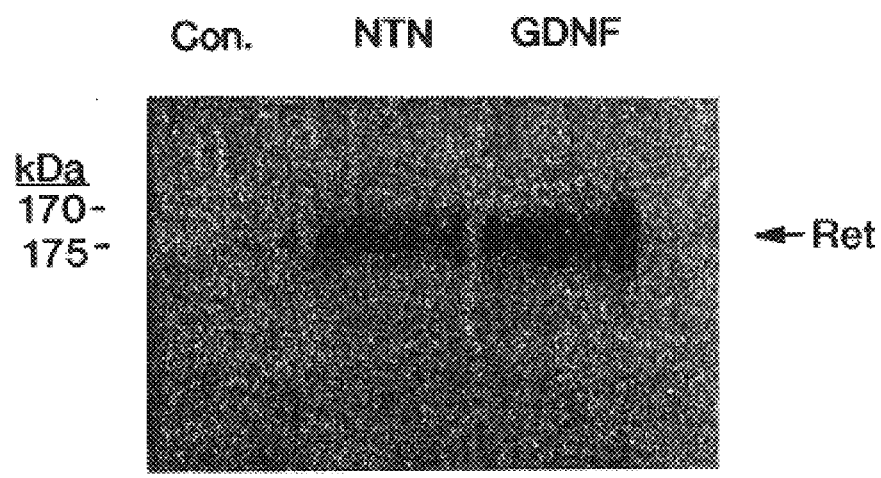
Figure 7E:
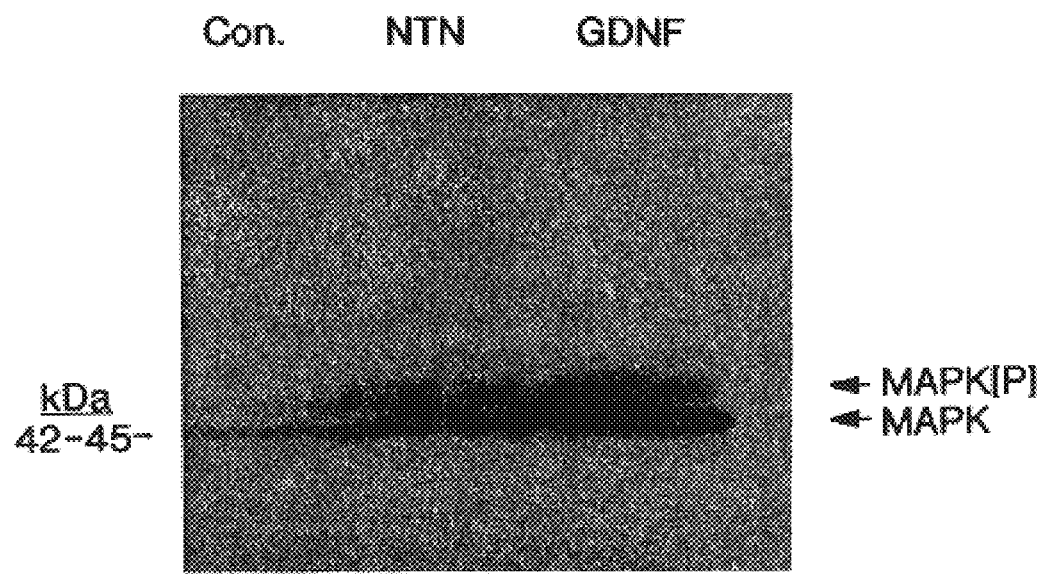
Figure 7F:
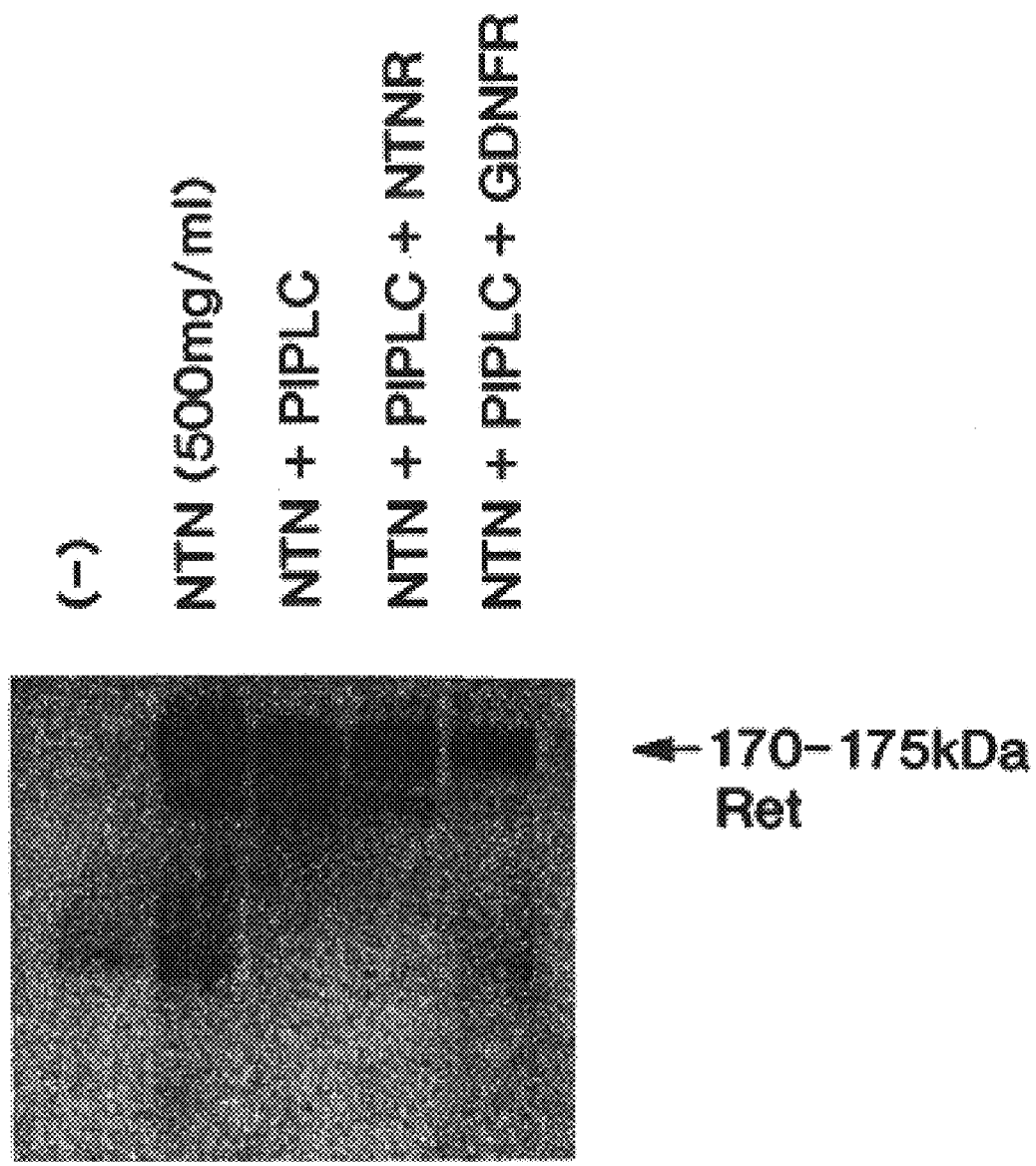

Since NTNRα, like GDNFRα, lacks a cytoplasmic domain and appears to be anchored to the outer surface of the cell via GPI, transmission of the NTN signals to the cell interior must involve additional proteins. As the tyrosine kinase receptor Ret, which by itself does not bind GDNF or NTN with a high affinity (Jing et al. *Cell* 85:1113–1124 (1996)); Treanor et al. *Nature* 382:80–83 (1996); data not shown), appears to be a signaling component of the GDNF receptor, Ret transduction of the NTN response following binding of NTN to NTNRα was determined. To assay for tyrosine phosphorylation, cells were incubated for 1 h at 37° C. with or without PIPLC, and then exposed to various concentrations of NTN. Cells were then removed from the plates with 2 mM EDTA in PBS and lysed with ice-cold buffer (10 mM sodium phosphate (pH 7.0), 100 mM NaCl, 1% NP40, 5 mM EDTA, 100 mM sodium vanadate, 2 mM PMSF, and 0.2 units of aprotinin), and used for immunoprecipitation with antisera raised against the 19 amino acid carboxyl terminus of Ret, followed by binding to protein A sepharose. The immunoprecipitated proteins were released by boiling in SDS sample buffer, separated on an 8% SDS-polyacrylamide gel, transferred to a nitrocellulose membrane, and reacted with anti-phosphotyrosine antibody (Upstate Biotechnology, Inc.); detection was with an ECL Western blotting detection system (Amersham Life Science). The human neuroblastoma cell line, TGW-1, which expresses endogenous c-ret (Ikeda et al. *Oncogene* 5:1291 (1990); Takahashi et al. *Oncogene* 6:297 (1991)), was exposed to NTN for 5 minutes, and the level of Ret tyrosine phosphorylation was determined. NTN clearly induced phosphorylation of Ret (FIG. 7D), as well as of the receptor tyrosine kinase responsive, cytoplasmic kinase ERK (i.e., MAPK) in this cell line (FIG. 7E), but not in 4 other neuroblastoma lines that were examined (data not shown). Furthermore, consistent with the hypothesis that NTNRα is an essential mediator between NTN and Ret, NTN failed to induce significant tyrosine phosphorylation on Ret in cells that were treated with PIPLC (FIG. 7F). A similar result was obtained with GDNF. Tyrosine-phosphorylated RET protein was readily detected in PIPLC-treated TGW-1, cell when NTN was added together with a soluble NTNRα.

Since these findings herein suggested that Ret participates in the transmission of the NTN signal, it was determined whether Ret is part of a putative NTN receptor complex. To examine the formation of protein complexes upon exposure to NTN, co-immunoprecipitation experiments were done NTNRα-expressing TGW-1cells exposed to 500 ng/ml of NTN. After exposure, cells were lysed a mild detergent brij 96 (Sigma) (Davis et al. 1993). For mammalian protein expression the complete open reading frame was amplified using PCR and cloned into a CMV based expression vector. For co-precipitation experiments, an epitope tag was inserted between the signal peptide and the mature coding sequence of NTNRα. When protein complexes were immunoprecipitated with a polyclonal antibody to Ret and then analyzed on a western blot using a polyclonal antibody to NTN, NTN was readily co-immunoprecipitated by Ret antibodies, which is consistent with the notion that NTN and Ret physically interact on the cell surface. To confirm that NTNRα is part of the NTN/Ret protein complex, human embryonic kidney 293 cells were transiently transfected with expression vectors, Ret alone or with a combination of expression vectors for c-ret and an epitope tagged NTNRα, exposed to NTN, and lysed with a mild detergent brij 96 (Sigma) (Davis et al. 1993). Putative immune complexes were immunoprecipitated with a polyclonal antibody against Ret, transferred onto a nitrocellulose filter, and analyzed with a polyclonal antibody against the epitope tagged NTNRα. In agreement with the idea that NTNRα and Ret can be found in a protein complex, NTNRα, in the presence, but not in the absence of NTN was readily co-immunoprecipitated by Ret antibodies. These findings demonstrated that NTN, NTNRα and Ret can form a complex on the cell surface, that Ret and NTNRα are components of a functional NTN receptor, an that NTNRα is an intermediary in the interaction between NTN and Ret.

To ascertain the potential role of NTNRα in the survival responses of developing neurons to neurotrophic factors and compare its function with that of GDNFRα, microinjection was used to introduce expression plasmids encoding NTNRα and GDNFRα into cultured neurons that normally do not survive in response to either GDNF or neurturin. Although neurturin promotes the survival of late fetal rat sympathetic neurons (Kotzbauer, 1996), from a survey of several different populations of neurons, it was found herein that sympathetic neurons of the superior cervical sympathetic ganglion (SCG) of postnatal day 4 (P4) mice are not supported by either neurturin or GDNF in culture. Because these neurons are also relatively easy to microinject and die rapidly in defined medium lacking neurotrophic factors, they are very useful for examining the involvement of NTNRα in neuronal survival and neurotrophic factor responsiveness. Ectopic expression of either NTNRα or GDNFRα alone in SCG neurons had a negligible effect on the survival response of these neurons to either GDNF or neurturin (less than 5% survive in medium containing these factors following injection with either NTNRα or GDNFRα expression plasmids). This suggests that neither GDNFRα nor NTNRα alone are capable of mediating survival responses to GDNF and neurturin. This is consistent with the idea that GPI-linked receptors cannot mediate responses to their ligands without the appropriate transmembrane signaling proteins like Ret in the case of GDNFRα (Treanor et al., 1996); Jing et al., 1996) and gp130 and LIFRβ in the case of CNTFRα (Davis et al., 1993).

Ret was reported as an essential signaling component of the GDNF receptor complex (Treanor et al., 1996; Jing et al., 1996; Trupp et al., 1996; Durbec et al., 1996; Vega, 1996). To see if neurons expressing both of these receptor components would exhibit specific survival responses to GDNF and neurturin, neurons were co-injected with expression plasmids for Ret and NTNRα or GDNFRα. Ectopic expression of Ret alone had only a small effect on the number of SCG neurons surviving in the presence of neurturin or GDNF (between 10 and 15%). However, neurons co-expressing NTNRα plus Ret had a substantially enhanced survival response to neurturin that was significantly greater than that of neurons expressing Ret alone (p=0.003, t-test, n=6). Likewise, neurons co-expressing GDNFRα plus Ret had substantially enhanced survival response to GDNF that was also significantly greater than that of neurons expressing Ret alone (p=0.0002, t-test, n=9). In contrast, neurons co-expressing GDNFRα plus Ret showed no enhanced survival response to neurturin; there were no more Ret/GDNFRα-expressing neurons surviving with neurturin that Ret-expressing neurons. Likewise, the number of Ret/NTNRα-expressing neurons surviving with GDNF was not significantly different from the number of Ret-expressing neurons surviving with this factor (p=0.2, t-test, n=9). These data confirm the results reported above.

Example 8
NTN is a Neuron Survival Factor in Vivo

To determine whether NTN can act to promote survival of midbrain DA neurons, cultures of E14 rat ventral midbrain, enriched for DA neurons, were investigated. This culture system revealed that, like GDNF, NTN can exert potent actions on the survival of tyrosine hydroxylase-expressing cells of the developing midbrain. The potency and efficacy of NTN was similar to that of GDNF, with NTN displaying a trend towards promoting survival of greater numbers of cells than seen with maximally-effective doses of GDNF.

The ability of NTN to promote survival in vitro of embryonic rat midbrain DA neurons suggests that NTN can be effective in promoting survival of DA neurons in the intact adult brain. As indicated herein, the tyrosine kinase Ret is a critical component of both GDNF and NTN receptor complexes and is expressed in adult rat midbrain DA neurons. To determine whether NTNRα is expressed in adult nigral DA neurons, in situ hybridization was employed. While sections of the adult rat ventral midbrain displayed strong signal for GDNFRα, which was largely confined to the pars compacta of the substantia nigra and the ventral tegmental area, a more modest and diffuse signal for signal for NTNRα was observed in the ventral midbrain. In sections stained for tyrosine hydroxylase, the majority of TH+ nigral cells displayed weak or equivocal signal for NTNRα, while intense hybridization was observed for GDNFRα in association with TH+ cells of the substantia nigra. Strong signal for NTNRα was, however, observed in regions immediately adjacent to midbrain DA neurons, including cells bordering the dorsolateral aspect of the pars compacta of the substantia nigra, the medial and lateral nuclei of the accessory optic tract, and interpeduncular nuclei. Taken with the ability of soluble NTNRα expression in and near adult nigral DA neurons, these results suggest that NTN is acting on adult nigral neurons.

It was determined herein that intranigral injection of NTN can promote the survival and TH expression of DA neurons following striatal 6-OHDA administration, and that the potency and efficacy of NTN is similar to that of GDNF. In order to independently assess viability and phenotypic expression of nigral DA neurons, cells were counted using both a retrograde fluorescent tracer, flurogold, and by immunocytochemistry for tyrosine hydroxylase. A single intranigral injection of 1 or 10 ug of NTN administered one week following 6-OHDA administration lead to nearly 3 fold higher cell viability (as assessed by the retrograde tracer flurogold) at one month post-lesion than seen in vehicle-treated animals. Examination of the number of cells expressing tyrosine hydroxylase revealed a significant increase in protection in rats treated with 10, but not I microgram of NTN. The effects of single injections of NTN on cell survival and TH expression were indistinguishable from that seen with comparable does of GDNF. Both NTN and GDNF can promote the survival of nigral DA neurons following neurotoxic or traumatic injury.

As shown herein, NTN is expressed in the developing and adult nigrostriatal system and can exert potent influences on the survival and phenotypic expression of nigral dopaminergic neurons. The actions of NTN to protect DA neurons and promote TH expression following 6-OHDA administration indicate that this factor can be a useful agent in the treatment of Parkinson's disease.

Example 9
NTNRα and GDNFRα Extracellular Domains Act as Receptor Agonists

The effects of GDNFRα and NTNRα extracellular domains as receptor agonists were determined by observing survival of ventral mesencephalic, embryonic rat, dopaminergic neurons treated with exogenously added extracellular domain of either receptor. Cultures enriched for dopaminergic neurons of the ventral mesencephalon were dissected from E14 rats, in which Day 0 was the day of the first appearance of the vaginal plug. The tissue was treated with enzyme, triturated to a single cell suspension, and plated as previously described (Poulsen et al., *Neuron* 13(5):1245–52 (1994)) with a few exceptions. Cells were plated on glass coverslips, and all growth factors were diluted first into a 20× concentrated solution of 1 mM HCl before the final dilution (resulting in a final concentration of 20 uM HCl in the medium). All factors were added once, at the time of plating. The concentration of insulin in the medium was decreased from 5 ug/ml to 2.5 ug/ml. Cultures were plated in triplicate. Either GDNFRα or NTNRα at 1 ug/ml was added to the cultures 2 hours after cell plating. At the same time, parallel cultures received either GDNFRα or NTNRα plus 50 ng/ml of either GDNF or NTN, or received 50ng/ml of GDNF or NTN without exogenously added receptor. After 4 days in culture, the cells were fixed and stained for tyrosine hydroxylase (TH), a marker for dopaminergic neurons, and the number of TH+ cells in each condition was counted and compared to control cultures (parallel cultures grown in the presence of no added factors). Both the GDNFRα and the NTNRα extracellular domains contained a histidine tag (6 histidine residues) at the C-terminus, which provided a convenient handle for purification of the extracellular domains. The His-tagged-GDNFRα ECD C-terminal is DGLAGASSH HHHHH, where one of the His residues normally present in the GDNFR sequence was used to provide part of the tag sequence. The molecules were produced in 293 cells (by transient transfection, supernatant harvested 96 hr after transfection), purified over a Ni-NTA column using standard IMAC purification procedure. The isolated ECDs were dialyzed into PBS and subsequently stored at 4° C.

Figure 8A:
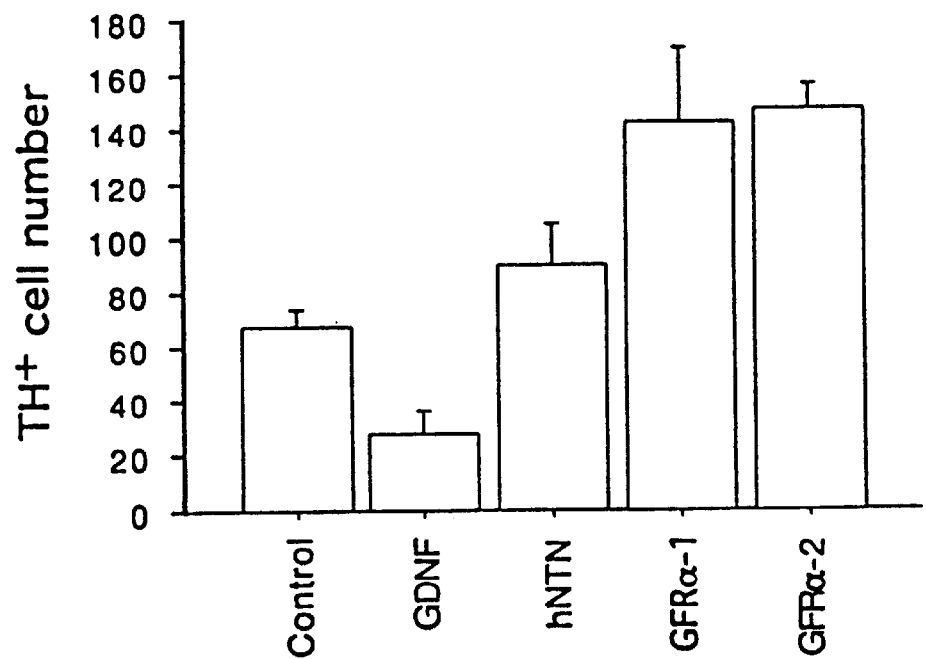
FIGS. 8A to 8C depict the survival response of dopaminergic neurons to soluble Ret-activating forms of NTNRα and GDNFRα extracellular domains.
Figure 8B:
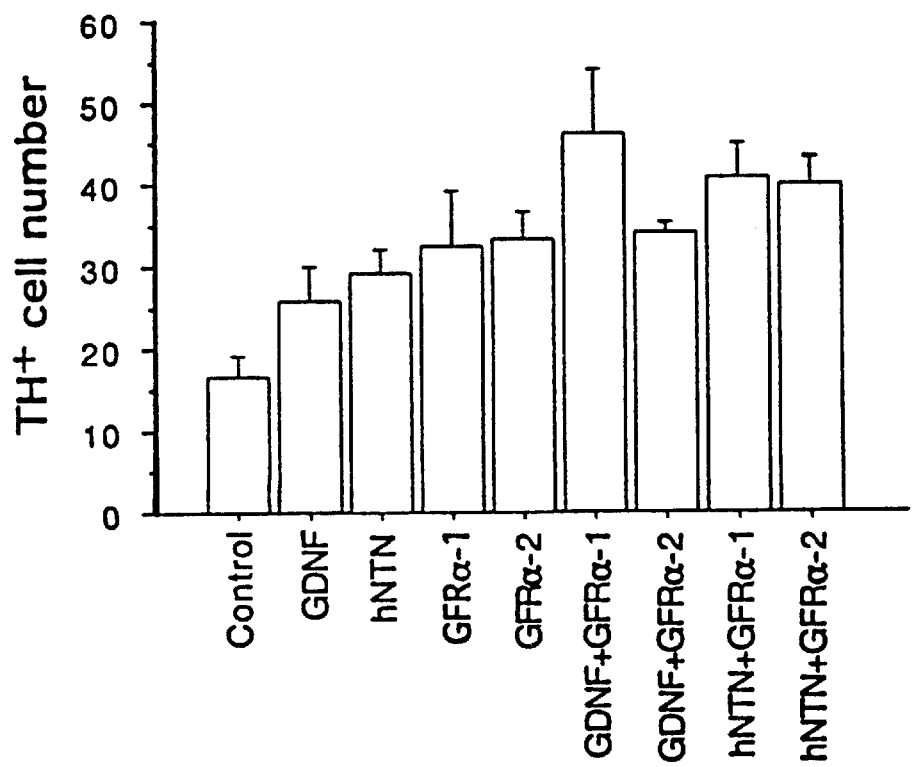
Figure 8C:
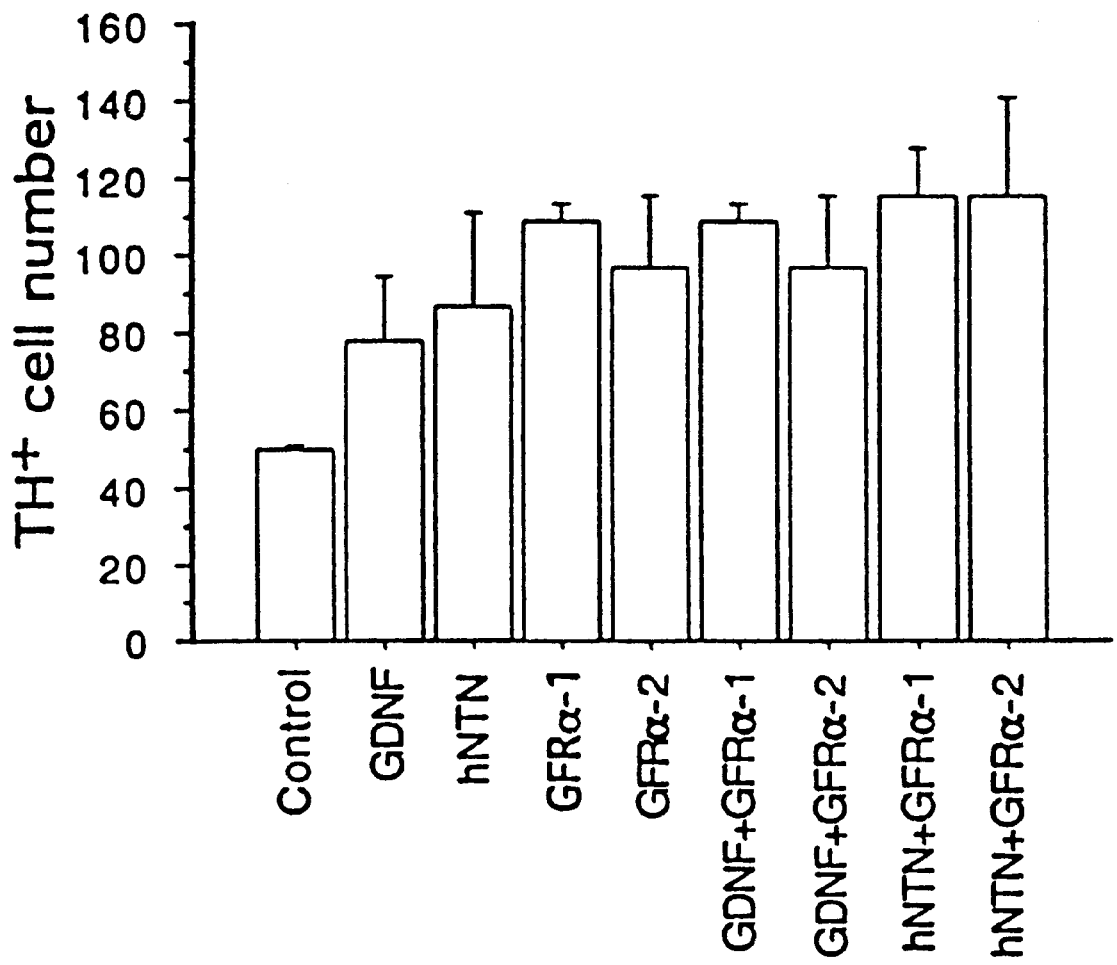

In three separate experiments GDNFRα and NTNRα extracellular domains, in both the absence and presence of exogenously added ligand, promoted survival of dopaminergic neurons that was significantly greater than control cultures (FIGS. 8A to 8C). In each case, the amount of survival was equal or slightly better than the amount of survival with ligand (GDNF or NTN) alone. Survival was further increased when both ligand and its particular receptor extracellular domain (e.g. NTN+NTNRα, GDNF+ GDNFRα) were added together. Anti-NTN monoclonal antibody added to a control culture (with no added factors) did not result in a decrease in the observed background level of cell growth, indicating that background growth during the test period was not due to endogenous NTN, if present. These results indicate that receptor extracellular domain addition of this family of receptors, without ligand, promotes a significant neuron survival effect over control.

Presented herein is a novel sequence encoding a novel receptor for neurturin, a recently discovered member of the GDNF protein family. The results presented herein reveal the existence of a novel family of multi-component receptors for growth and differentiation factors. The receptor complex is composed of a shared signaling subunit—the transmembrane tyrosine kinase receptor Ret—and a GPI-linked, receptor-specific-ligand-binding subunit—NTNRα in the case of NTN, and GDNFRα in the case of GDNF. In view of these findings, further details on the mechanism of action of NTN and GDNF on the molecular level can be determined. In addition, it is now clear that the distinct biological activities of the GDNF/NTN protein family are determined by the distinct tissue distribution of their respective ligand-binding-receptor components rather then by the ability to activate different signaling systems. Finally, the data presented herein provides a contrasting and simple biological rational for the involvement of what previously appeared to be a needlessly complex way to activate a tyrosine kinase receptor (reviewed in Lindsay and Yancopoulos, *Neuron* 17:571–574 (1996)). It is now apparent that changing the ligand-binding accessory molecule is a most economic way to recruit the same signalling system for usage by multiple growth factors, and that GPI-linked proteins are economic ligand-binding accessory molecules. Use of a single transmembrane signalling system by multiple growth factors appears to be employed by cytokines (Stahl and Yancopoulos, *Ann. Rev. Biophys, Biomol. Struct.* 24:269–291 (1993)) as well as by members of the transforming growth factor protein family (Wrana et al., *Nature* 370:341–347 (1994)). Likewise, GPI-linked proteins are used as ligand-binding accessory molecules in several multi-component receptors, such as the bacterial endotoxin receptor (Lee et al., *Proc. Natl Acad Sci. USA* 90:9930–9934 (1993); Pugin et al., *Proc. Natl. Acad Sci. USA* 90:2744–2748 (1993)) and the receptor for ciliary neurotrophic factor (Davies et al., *Science* 259:17361739 (1993)). The discovery of the receptor and associated receptor system presented herein defines a novel paradigm in signal transduction, highlights the diverse strategies which are used to transmit extracellular signals in the vertebrate nervous system, and provides means for modulating and controlling cell activity and survival that expand the treatment modalities available to the clinician.

What is claimed is:

1. A method for identifying a molecule which binds to an NTNRα comprising the amino acid sequence of SEQ ID NO: 3 or SEQ ID NO: 6, or an amino acid sequence having at least 90% sequence identity with SEQ ID NO: 3 or SEQ ID NO: 6 and having solely conservative mutations relative to SEQ ID NO: 3 or SEQ ID NO: 6, comprising (a) exposing said NTNRα to candidate molecule suspected of binding thereto in vitro, and (b) determining whether said candidate molecule binds to said NTNRα.

2. The method of claim 1, wherein the NTNRα is soluble NTNRα.

3. The method of claim 2 wherein said NTNRα is immobilized on a solid phase.

4. The method of claim 3 wherein said NTNRα is epitope-tagged.

5. The method of claim 3 wherein said NTNRα is in the for of an immunoadhesin comprising an NTNRα extracellular domain sequence fused to an immunoglobulin heavy chain constant domain.

6. The method of claim 3 wherein said candidate molecule is labeled.

7. The method of claim 6 wherein the kabek is radiolabel.

8. The method of claim 1 wherein said NTNRα comprises the amino acid sequence of SEQ ID NO: 3 or SEQ ID NO: 6.

9. The method of claim 1 wherein said NTNRα has the amino acid sequence of SEQ ID NO: 3 or SEQ ID NO: 6.

10. A method for purifying a molecule which binds to an NTNRα comprising the amino acid sequence of SEQ ID NO: 3 or SEQ ID NO: 6, or an amino acid sequence having at least 90% sequence identity with SEQ ID NO: 3 or SEQ ID NO: 6 and having solely conservative mutations relative to SEQ ID NO: 3 or SEQ ID NO: 6, comprising adsorbing the molecule to said NTNRα immobilized on a solid phase and recovering the molecule from the immobilized NTNRα.

11. The method of claim 10 wherein said solid surface is an inert and porous matrix or resin to which said NTNRα is covalently attached.

12. The method of claim 11 wherein said solid surface is a Protein A column.

13. The method of claim 12 wherein said NTNRα is in the form of an immunoadhesin comprising an NTNRα extracellular domain sequence fused to an immunoglobulin constant region.

14. A method for purifying a molecule which binds to amino acids 23 to 431 of SEQ ID NO: 3 or SEQ ID NO: 6, comprising adsorbing the molecule to a chimeric polypeptide comprising a fusion of amino acids 23 to 431 of SEQ ID NO: 3 or SEQ ID NO: 6 to an immunoglobulin constant domain sequence immobilized on a solid phase and recovering the molecule from the immobilized chimeric polypeptide.

15. A method for identifying a molecule which binds to an NTNRα comprising amino acids 23 to 431 of SEQ ID NO: 3 or SEQ D NO: 6, or an amino acid sequence having at least 95% sequence identity with amino acids 23 to 431 of SEQ ID NO: 3 or SEQ ID NO: 6 and comprising solely conservative mutations relative to amino aids 23 to 431 of SEQ ID NO: 3 or SEQ ID NO: 6, comprising (a) exposing said NTNRα to NTN and a candidate molecule suspected of binding to said NTNRα, in vitro, under conditions such that, but for the presence of the candidate molecule, said NTN binds to said NTNRα, and (b) detecting whether binding occurs between said NTN and NTNRα to determine whether the candidate molecule inhibits said binding.

16. The method of claim 15 wherein said NTNRα comprises the amino acid sequence of SEQ ID NO: 3 or SEQ ID NO: 6.

17. The method of claim 15 wherein said NTNRα has the amino acid sequence of SEQ ID NO: 3 or SEQ ID NO: 6.

18. The method of claim 15 wherein said NTNRα ligand is labeled.

19. The method of claim 18 wherein said NTNRα ligand is $I^{125}$-NTN.

20. The method of claim 19 wherein said NTNRα is exposed to said $I^{125}$-NTN before exposure to said candidate molecule.

21. The method of claim 19 wherein said $I^{125}$-NTN and said candidate molecule are added to said NTNRα simultaneously.

* * * * *

UNITED STATES PATENT AND TRADEMARK OFFICE
CERTIFICATE OF CORRECTION

PATENT NO. : 6,342,348 B1
DATED : January 29, 2002
INVENTOR(S) : Robert D. Klein et al.

It is certified that error appears in the above-identified patent and that said Letters Patent is hereby corrected as shown below:

Title page,
Item [60], The Related U.S. Application Data under item [60] instead of
"[60] Continuation of application No. 08/957,063, filed on Oct. 24, 1997, now Pat. No. 6,025,157, which is a division of application No. 08/802,805, filed on Feb. 18, 1997. [60] Provisional application No. 60/038,839, filed on Feb. 18, 1997, now abandoned, and provisional application No. 60/049,818, filed on Jun. 9, 1997, now abandoned."
should read
-- [60] Divisional of application No. 08/957,063, filed on Oct. 24, 1997, now Pat. No. 6,025,157. [60] Provisional application No. 60/038,839, filed on Feb. 18, 1997, now abandoned, and provisional application No. 60/049,818, filed on Jun. 9, 1997, now abandoned. --

Column 101,
Line 52, instead of "the amino acid sequence" should read -- amino acids 23 to 431 --;
Line 54, instead of "90%" it should read -- 95% --;
Line 54, instead of "sequence identity with_SEQ ID NO: 3" it should read -- sequence identity with amino acids 23 to 431 of SEQ ID NO: 3 --;
Line 56, instead of "to SEQ ID NO: 3" it should read -- to amino acids 23 to 431 of SEQ ID NO: 3 --

Signed and Sealed this

Sixteenth Day of July, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.    : 6,342,348 B1
DATED         : January 29, 2002
INVENTOR(S)   : Robert D. Klein et al.

It is certified that error appears in the above-identified patent and that said Letters Patent is hereby corrected as shown below:

<u>Title page,</u>
Item [73], Assignee, instead of "[73] Genetech, Inc., South San Francisco, CA (US)" should read
-- [73] Genentech, Inc., South San Francisco, CA (US) --

<u>Column 101,</u>
Line 67, instead of "for of an" should read -- form of an --;

<u>Column 102,</u>
Line 54, instead of "the kabek" it should read -- the label --;
Line 58, instead of "has the amino" it should read -- consists of the amino --;
Line 61, instead of "acid sequence" it should read -- acids 23 of 431 of --
Line 63, instead of "90%" it should read -- 95% --;
Line 63, instead of "with SEQ" it should read -- with amino acids 23 of 431 of SEQ --
Line 64, instead of "relatine to SEQ" it should read -- relatine to amino acids 23 to 431 of SEQ --;

<u>Column 103,</u>
Line 23, instead of "amino aids" it should read -- amino acids --;

<u>Column 104,</u>
Line 10, instead of "has the amino" it should read -- consists of the amino. --

Signed and Sealed this

Twenty-second Day of October, 2002

Attest:

*Attesting Officer*

JAMES E. ROGAN
*Director of the United States Patent and Trademark Office*

SEQUENCE LISTING (1) GENERAL INFORMATION:

(iii) NUMBER OF SEQUENCES: 19

(2) INFORMATION FOR SEQ ID NO: 1:

(i) SEQUENCE CHARACTERISTICS:
        (A) LENGTH: 2600 base pairs
        (B) TYPE: Nucleic Acid
        (C) STRANDEDNESS: Single
        (D) TOPOLOGY: Linear (xi) SEQUENCE DESCRIPTION: SEQ ID NO: 1:

```
CCGAGAGCTG CGGGGGGAGG AGGAGGAGGG TGCCGACGCT TGAGTGGGTT                    50
```

| | |
|---|---|
| CGAGCCCGAG CCGTAGCCGG GGGAGCCAGT CAGTTTCCGG CCAAGGCAGC | 100 |
| AGGGAGAAAG ACAAAAAAAC GGTGGGATTT ATTTAACATG ATCTTGGCAA | 150 |
| ACGTCTTCTT CCTCTTCTTC TTTCTAGACG AGACCCTCCG CTCTTTGGCC | 200 |
| AGCCCTTCCT CCCTGCAGGA CCCCGAGCTC CACGGCTGGC GCCCCCCAGT | 250 |
| GGACTGTGTC CGGGCCAATG AGCTGTGTGC CGCCGAATCC AACTGCAGCT | 300 |
| CTCGCTACCG CACTCTGCGG CAGTGCCTGG CAGGCCGCGA CCGCAACACC | 350 |
| ATGCTGGCCA ACAAGGAGTG CCAGGCGGCC TTGGAGGTCT TGCAGGAGAG | 400 |
| CCCGCTGTAC GACTGCCGCT GCAAGCGGGG CATGAAGAAG GAGCTGCAGT | 450 |
| GTCTGCAGAT CTACTGGAGC ATCCACCTGG GGCTGACCGA GGGTGAGGAG | 500 |
| TTCTACGAAG CCTCCCCCTA TGAGCCGGTG ACCTCCCGCC TCTCGGACAT | 550 |
| CTTCAGGCTT GCTTCAATCT TCTCAGGGAC AGGGGCAGAC CCGGTGGTCA | 600 |
| GCGCCAAGAG CAACCATTGC CTGGATGCTG CCAAGGCCTG CAACCTGAAT | 650 |
| GACAACTGCA AGAAGCTGCG CTCCTCCTAC ATCTCCATCT GCAACCGCGA | 700 |
| GATCTCGCCC ACCGAGCGCT GCAACCGCCG CAAGTGCCAC AAGGCCCTGC | 750 |
| GCCAGTTCTT CGACCGGGTG CCCAGCGAGT ACACCTACCG CATGCTCTTC | 800 |
| TGCTCCTGCC AAGACCAGGC GTGCGCTGAG CGCCGCCGGC AAACCATCCT | 850 |
| GCCCAGCTGC TCCTATGAGG ACAAGGAGAA GCCCAACTGC CTGGACCTGC | 900 |
| GTGGCGTGTG CCGGACTGAC CACCTGTGTC GGTCCCGGCT GGCCGACTTC | 950 |
| CATGCCAATT GTCGAGCCTC CTACCAGACG GTCACCAGCT GCCCTGCGGA | 1000 |
| CAATTACCAG GCGTGTCTGG GCTCTTATGC TGGCATGATT GGGTTTGACA | 1050 |
| TGACACCTAA CTATGTGGAC TCCAGCCCCA CTGGCATCGT GGTGTCCCCC | 1100 |
| TGGTGCAGCT GTCGTGGCAG CGGGAACATG GAGGAGGAGT GTGAGAAGTT | 1150 |
| CCTCAGGGAC TTCACCGAGA ACCCATGCCT CCGGAACGCC ATCCAGGCCT | 1200 |
| TTGGCAACGG CACGGACGTG AACGTGTCCC AAAAGGCCC CTCGTTCCAG | 1250 |
| GCCACCCAGG CCCCTCGGGT GGAGAAGACG CCTTCTTTGC CAGATGACCT | 1300 |
| CAGTGACAGT ACCAGCTTGG GGACCAGTGT CATCACCACC TGCACGTCTG | 1350 |
| TCCAGGAGCA GGGGCTGAAG GCCAACAACT CCAAAGAGTT AAGCATGTGC | 1400 |
| TTCACAGAGC TCACGACAAA TATCATCCCA GGGAGTAACA AGGTGATCAA | 1450 |
| ACCTAACTCA GGCCCCAGCA GAGCCAGACC GTCGGCTGCC TTGACCGTGC | 1500 |
| TGTCTGTCCT GATGCTGAAA CTGGCCTTGT AGGCTGTGGG AACCGAGTCA | 1550 |
| GAATATTTTT GAAAGCTACG CAGACAAGAA CAGCCGCCTG ACGAAATGGA | 1600 |
| AACACACACA GACACACACA CACCTTGCAA AAAAAAATT GTTTTCCCA | 1650 |
| CCTTGTCGCT GAACCTGTCT CCTCCCAGGT TTCTTCTCTG GAGAAGTTTT | 1700 |
| TGTAAACCAA ACAGACAAGC AGGCAGGCAG CCTGAGAGCT GGCCCAGGGG | 1750 |
| TCCCCTGGCA GGGGAAACTC TGGTGCCGGG GAGGGCACGA GGCTCTAGAA | 1800 |
| ATGCCCTTCA CTTTCTCCTG GTGTTTTTCT CTCTGGACCC TTCTGAAGCA | 1850 |
| GAGACCGGAC AAGAGCCTGC AGCGGAAGGG ACTCTGGGCT GTGCCTGAGG | 1900 |
| CTGGCTGGGG GCAGGACAAC ACAGCTGCTT CCCCAGGCTG CCCACTCTGG | 1950 |
| GGACCCGCTG GGGGCTGGCA GAGGGCATCG GTCAGCGGGG CAGCGGGGCT | 2000 |
| GGCCATGAGG GTCCACCTTC AGCCCTTTGG CTTCAAGGAT GGAGATGGTT | 2050 |

-continued

| | |
|---|---|
| TTGCCCTCCC TCTCTGCCCT CGGGTGGGGC TGGTGGGTCT GCAGCTGGTG | 2100 |
| TGGGAACTTC CCCACGGATG GCGGTGGAGG GGGTTCGCAC CGTGCTGGGC | 2150 |
| TCCCCCTGAC TGTAGCACGG AGTGTTGGGG CTGGGGGCCA GCTCCAGGAG | 2200 |
| GGCTTGAGAG CTCAGCCTGC CTGGGAGAGC CCTTGTGGCG AGGCATTAAA | 2250 |
| ACTTGGGCAC CAGCTTCTTT CTCGGTGGCA GAAATTTTGA AGTCAGAGAG | 2300 |
| AAACGGTCCT TGTTGGCTT CTTTGCTTTC TCGTGGGTCC TTTGGCAGGC | 2350 |
| CTCCCTTTGG GGAGAGGGAG GGGAGAGACC ACAGCCGGGT GTGTGTCTGC | 2400 |
| AGCACCGTGG GCCCTCAAGC TTTCCTGCTG TCTTCTCCCT CCTCCTCCTT | 2450 |
| TCCCCTTTCT CTTTCCTCAT TTCCTAGACG TACGTCAACT GTATGTACAT | 2500 |
| ACCGGGGCTC CTCTCCTAAC ATATATGTAT ATACACATCC ATATACATAT | 2550 |
| ATTGTGTGGT TTCCCCTTTC TTTCCTTTTT TAAGCAACAA AACTATGGGG | 2600 |

(2) INFORMATION FOR SEQ ID NO: 2:

(i) SEQUENCE CHARACTERISTICS:
        (A) LENGTH: 1392 base pairs
        (B) TYPE: Nucleic Acid
        (C) STRANDEDNESS: Single
        (D) TOPOLOGY: Linear (xi) SEQUENCE DESCRIPTION: SEQ ID NO: 2:

| | |
|---|---|
| ATGATCTTGG CAAACGTCTT CTTCCTCTTC TTCTTTCTAG ACGAGACCCT | 50 |
| CCGCTCTTTG GCCAGCCCTT CCTCCCTGCA GGACCCCGAG CTCCACGGCT | 100 |
| GGCGCCCCCC AGTGGACTGT GTCCGGGCCA ATGAGCTGTG TGCCGCCGAA | 150 |
| TCCAACTGCA GCTCTCGCTA CCGCACTCTG CGGCAGTGCC TGGCAGGCCG | 200 |
| CGACCGCAAC ACCATGCTGG CCAACAAGGA GTGCCAGGCG GCCTTGGAGG | 250 |
| TCTTGCAGGA GAGCCCGCTG TACGACTGCC GCTGCAAGCG GGGCATGAAG | 300 |
| AAGGAGCTGC AGTGTCTGCA GATCTACTGG AGCATCCACC TGGGGCTGAC | 350 |
| CGAGGGTGAG GAGTTCTACG AAGCCTCCCC CTATGAGCCG GTGACCTCCC | 400 |
| GCCTCTCGGA CATCTTCAGG CTTGCTTCAA TCTTCTCAGG ACAGGGGCA | 450 |
| GACCCGGTGG TCAGCGCCAA GAGCAACCAT TGCCTGGATG CTGCCAAGGC | 500 |
| CTGCAACCTG AATGACAACT GCAAGAAGCT GCGCTCCTCC TACATCTCCA | 550 |
| TCTGCAACCG CGAGATCTCG CCCACCGAGC GCTGCAACCG CCGCAAGTGC | 600 |
| CACAAGGCCC TGCGCCAGTT CTTCGACCGG GTGCCCAGCG AGTACACCTA | 650 |
| CCGCATGCTC TTCTGCTCCT GCCAAGACCA GGCGTGCGCT GAGCGCCGCC | 700 |
| GGCAAACCAT CCTGCCCAGC TGCTCCTATG AGGACAAGGA GAAGCCCAAC | 750 |
| TGCCTGGACC TGCGTGGCGT GTGCCGGACT GACCACCTGT GTCGGTCCCG | 800 |
| GCTGGCCGAC TTCCATGCCA ATTGTCGAGC CTCCTACCAG ACGGTCACCA | 850 |
| GCTGCCCTGC GGACAATTAC CAGGCGTGTC TGGGCTCTTA TGCTGGCATG | 900 |
| ATTGGGTTTG ACATGACACC TAACTATGTG GACTCCAGCC CCACTGGCAT | 950 |
| CGTGGTGTCC CCCTGGTGCA GCTGTCGTGG CAGCGGGAAC ATGGAGGAGG | 1000 |
| AGTGTGAGAA GTTCCTCAGG GACTTCACCG AGAACCCATG CCTCCGGAAC | 1050 |
| GCCATCCAGG CCTTTGGCAA CGGCACGGAC GTGAACGTGT CCCCAAAAGG | 1100 |
| CCCCTCGTTC CAGGCCACCC AGGCCCCTCG GGTGGAGAAG ACGCCTTCTT | 1150 |

-continued

```
TGCCAGATGA CCTCAGTGAC AGTACCAGCT TGGGGACCAG TGTCATCACC            1200

ACCTGCACGT CTGTCCAGGA GCAGGGGCTG AAGGCCAACA ACTCCAAAGA            1250

GTTAAGCATG TGCTTCACAG AGCTCACGAC AAATATCATC CCAGGGAGTA            1300

ACAAGGTGAT CAAACCTAAC TCAGGCCCCA GCAGAGCCAG ACCGTCGGCT            1350

GCCTTGACCG TGCTGTCTGT CCTGATGCTG AAACTGGCCT TG                    1392
```

(2) INFORMATION FOR SEQ ID NO: 3:

(i) SEQUENCE CHARACTERISTICS:
        (A) LENGTH: 464 amino acids
        (B) TYPE: Amino Acid
        (D) TOPOLOGY: Linear (xi) SEQUENCE DESCRIPTION: SEQ ID NO: 3:

```
Met Ile Leu Ala Asn Val Phe Phe Leu Phe Phe Phe Leu Asp Glu
 1               5                  10                  15

Thr Leu Arg Ser Leu Ala Ser Pro Ser Leu Gln Asp Pro Glu
                20                  25                  30

Leu His Gly Trp Arg Pro Pro Val Asp Cys Val Arg Ala Asn Glu
                35                  40                  45

Leu Cys Ala Ala Glu Ser Asn Cys Ser Ser Arg Tyr Arg Thr Leu
                50                  55                  60

Arg Gln Cys Leu Ala Gly Arg Asp Arg Asn Thr Met Leu Ala Asn
                65                  70                  75

Lys Glu Cys Gln Ala Ala Leu Glu Val Leu Gln Glu Ser Pro Leu
                80                  85                  90

Tyr Asp Cys Arg Cys Lys Arg Gly Met Lys Lys Glu Leu Gln Cys
                95                  100                 105

Leu Gln Ile Tyr Trp Ser Ile His Leu Gly Leu Thr Glu Gly Glu
                110                 115                 120

Glu Phe Tyr Glu Ala Ser Pro Tyr Glu Pro Val Thr Ser Arg Leu
                125                 130                 135

Ser Asp Ile Phe Arg Leu Ala Ser Ile Phe Ser Gly Thr Gly Ala
                140                 145                 150

Asp Pro Val Val Ser Ala Lys Ser Asn His Cys Leu Asp Ala Ala
                155                 160                 165

Lys Ala Cys Asn Leu Asn Asp Asn Cys Lys Lys Leu Arg Ser Ser
                170                 175                 180

Tyr Ile Ser Ile Cys Asn Arg Glu Ile Ser Pro Thr Glu Arg Cys
                185                 190                 195

Asn Arg Arg Lys Cys His Lys Ala Leu Arg Gln Phe Phe Asp Arg
                200                 205                 210

Val Pro Ser Glu Tyr Thr Tyr Arg Met Leu Phe Cys Ser Cys Gln
                215                 220                 225

Asp Gln Ala Cys Ala Glu Arg Arg Gln Thr Ile Leu Pro Ser
                230                 235                 240

Cys Ser Tyr Glu Asp Lys Glu Lys Pro Asn Cys Leu Asp Leu Arg
                245                 250                 255

Gly Val Cys Arg Thr Asp His Leu Cys Arg Ser Arg Leu Ala Asp
                260                 265                 270

Phe His Ala Asn Cys Arg Ala Ser Tyr Gln Thr Val Thr Ser Cys
                275                 280                 285

Pro Ala Asp Asn Tyr Gln Ala Cys Leu Gly Ser Tyr Ala Gly Met
```

```
                    290             295             300
Ile Gly Phe Asp Met Thr Pro Asn Tyr Val Asp Ser Ser Pro Thr
                305             310             315
Gly Ile Val Val Ser Pro Trp Cys Ser Cys Arg Gly Ser Gly Asn
                320             325             330
Met Glu Glu Glu Cys Glu Lys Phe Leu Arg Asp Phe Thr Glu Asn
                335             340             345
Pro Cys Leu Arg Asn Ala Ile Gln Ala Phe Gly Asn Gly Thr Asp
                350             355             360
Val Asn Val Ser Pro Lys Gly Pro Ser Phe Gln Ala Thr Gln Ala
                365             370             375
Pro Arg Val Glu Lys Thr Pro Ser Leu Pro Asp Asp Leu Ser Asp
                380             385             390
Ser Thr Ser Leu Gly Thr Ser Val Ile Thr Thr Cys Thr Ser Val
                395             400             405
Gln Glu Gln Gly Leu Lys Ala Asn Asn Ser Lys Glu Leu Ser Met
                410             415             420
Cys Phe Thr Glu Leu Thr Thr Asn Ile Ile Pro Gly Ser Asn Lys
                425             430             435
Val Ile Lys Pro Asn Ser Gly Pro Ser Arg Ala Arg Pro Ser Ala
                440             445             450
Ala Leu Thr Val Leu Ser Val Leu Met Leu Lys Leu Ala Leu
                455             460             464

(2) INFORMATION FOR SEQ ID NO: 4:

(i) SEQUENCE CHARACTERISTICS:
        (A) LENGTH: 3358 base pairs
        (B) TYPE: Nucleic Acid
        (C) STRANDEDNESS: Single
        (D) TOPOLOGY: Linear (xi) SEQUENCE DESCRIPTION: SEQ ID NO: 4:

GCGGTGGCGG CCGCTCTAGA ACTAGTGGAT CCCCGGGCTG CAGGAATTCG         50

GCACGAGAGT GAGCCGAGCA AGGGTTAGCG GGAGAAGATT TTTTTTTTTT        100

TGAATCTTTT TCTTCGTCTT GGTGCCAAAG AAGCGACTCT GGTCTCCCGT        150

CCTAGAAGCT CCTACTGGAT TGCTCCTATT CCGTCGGTGG ATTTCTTTCC        200

TATTCGCATT TATTCTGACC CCCTCCCTCG CTGCTTCCTT CCAGCCCTTC        250

ACTTTCAGAT CGCCTCGCCC CCACCTCTCC AGTCCCCTCC TGGGAAGTGC        300

AGGGGAATTG ACCCACGGG GACTCACGCC TTCCCGGACG CGCGAGCAAA         350

GGGCTGGGCT GACCTCAGGA CCAGGCTGTT GGCTTAGAAG GCAGCCAGAC        400

ACATAGCTAC GTGTGTTTGA TTTCAGTGGC AAGGGGGGAC GTCGAGAGGC        450

AGCCCACCGC CCGCCTCCTA CCCCTCCCCC TCCAACCAGC AGTGAGAATC        500

CCAGGACTCG GGATCTTCAA CCGGCGGCCG CCCGGCGGGA TCTCCGCATT        550

GGATTTGGGG GTCGTTATTG CTCGGCTGTT ATTATTATCG TTATTTTATT        600

TTTATTTTTT AAACCTAAGG GAGAAAGACA CATACACACA AAACTGTGGG        650

ATTTATTTAA CATGATCTTG GCAAACGCCT TCTGCCTCTT CTTCTTTTTA        700

GACGAAACCC TCCGCTCTTT GGCCAGCCCT TCCTCCCTGC AGGGCTCTGA        750

GCTCCACGGC TGGCGCCCCC AAGTGGACTG TGTCCGGGCC AATGAGCTGT        800

GTGCGGCTGA ATCCAACTGC AGCTCCAGGT ACCGCACCCT TCGGCAGTGC        850
```

```
CTGGCAGGCC GGGATCGCAA TACCATGCTG GCCAATAAGG AGTGCCAGGC        900
AGCCCTGGAG GTCTTGCAGG AAAGCCCACT GTATGACTGC CGCTGCAAGC        950
GGGGCATGAA GAAGGAGCTG CAGTGTCTGC AGATCTACTG GAGCATCCAT       1000
CTGGGGCTGA CAGAGGGTGA GGAGTTCTAT GAAGCTTCCC CCTATGAGCC       1050
TGTGACCTCG CGCCTCTCGG ACATCTTCAG GCTCGCTTCA ATCTTCTCAG       1100
GGACAGGGAC AGACCCGGCG GTCAGTACCA AAAGCAACCA CTGCCTGGAT       1150
GCCGCCAAGG CCTGCAACCT GAATGACAAC TGCAAGAAGC TTCGCTCCTC       1200
TTATATCTCC ATCTGCAACC GTGAGATCTC TCCCACCGAA CGCTGCAACC       1250
GCCGCAAGTG CCACAAGGCT CTGCGCCAGT TCTTTGACCG TGTGCCCAGC       1300
GAGTATACCT ACCGCATGCT CTTCTGCTCC TGTCAGGACC AGGCATGTGC       1350
TGAGCGTCGC CGGCAAACCA TCCTGCCCAG TTGCTCCTAT GAGGACAAGG       1400
AGAAGCCCAA CTGCCTGGAC CTGCGCAGCC TGTGTCGTAC AGACCACCTG       1450
TGCCGGTCCC GACTGGCAGA TTTCCACGCC AACTGTCGAG CCTCCTACCG       1500
GACAATCACC AGCTGTCCTG CGGACAACTA CCAGGCATGT CTGGGCTCCT       1550
ATGCTGGCAT GATTGGGTTT GATATGACAC CCAACTATGT GGACTCCAAC       1600
CCCACGGGCA TCGTGGTGTC TCCCTGGTGC AATTGTCGTG GCAGTGGGAA       1650
CATGGAAGAA GAGTGTGAGA AGTTCCTCAG GGACTTCACG GAAAACCCAT       1700
GCCTCCGGAA TGCCATTCAG GCCTTTGGTA ATGGCACAGA TGTGAACATG       1750
TCTCCCAAAG GCCCCTCACT CCCAGCTACC CAGGCCCCTC GGGTGGAGAA       1800
GACTCCTTCA CTGCCAGATG ACCTCAGTGA CAGCACCAGC CTGGGGACCA       1850
GTGTCATCAC CACCTGCACA TCTATCCAGG AGCAAGGGCT GAAGGCCAAC       1900
AACTCCAAAG AGTTAAGCAT GTGCTTCACA GAGCTCACGA CAAACATCAG       1950
TCCAGGGAGT AAAAAGGTGA TCAAACTTAA CTCAGGCTCC AGCAGAGCCA       2000
GACTGTCGGC TGCCTTGACT GCCCTCCCAC TCCTGATGCT GACCTTGGCC       2050
TTGTAGGCCT TTGGAACCCA GCACAAAAGT TCTTCAAGCA ACCCAGATAT       2100
GAACTCCCGC CTGACAAAAT GGAAACACAC GCATACACAC ATGCACACAC       2150
ACACAAACAC ACACACACAC ACACACACAC ACACACACAC ACACACACAC       2200
ACACCCCTTG CAAAAACACT TTTTTTCCTA CATTGTCTCT GAACCTTTCT       2250
CCTCCCAAGT TTCTTCTCTG GAGAAGTTTT TCTAAACCAA ACAGACAAGC       2300
AGGCGGGCAG TCAGAAGCCT GCCCAGAGGT CCCCTGCAAG GGACACCCAG       2350
CACCAACGAG GGCTCAAGGC TCTTGAGAGA CTCTTTTCTC TTCACTGGTG       2400
TTTTCTCTCT GGACAAGATG AGACCCTGAT GTGGAAGGTA CTTTGCTGTG       2450
CCTGGTGTGG ACTGGGGAAA GGACAGTTGC AGCTGCCTAC TCTGGGGACC       2500
TGCCCAAGGG TTCACAGAGA GTCTCAGTCA GCAAGGAAGC AGGGCTGGCC       2550
ACAAGGACTT TGTCACCTCT TCCTCTTGGC TTCAGAGATG GAAATGGTTT       2600
GCTGCCATCC CCAGCCATTA TGTGGCCTAG TGGGTTTAAG TCTGGAGTAG       2650
GAAGCCTCAT GGCAGCTTCA GGCCATGGTG CCTGTAGTAT AGCTGGGGTT       2700
GGGAGCTGTT ACAGGAGGAA GCTTCTTTGG GGCATGAGCA AGCCTTGGTT       2750
GGGCACCAGC TCCAAGATGT ACCTTCCTCC TTTATGCCAG GAATCTTGAA       2800
```

```
GTCAAAGAGA AATGATCCTC TGTTGGCTCT TTTTTGTTTG TTTTTGAATT          2850

TTTTTGTGGG TCCATTTGGC AGGTCTCTCT TGGGGAGAAG GGCTGTTGAG          2900

TGGGGCTGGG GAGACCCTAG CTGGGCGTGT GTATGGAGCA CTCTGGTGGG          2950

TTCCCAAGCT TGCCCCTTCT CTCTTCTTGT TTCTGCTTTC TCTCTCATTT          3000

CTGAGACATT CATGCACTGT CTGTACATAC TGGGTCTCCT TTCTCAACAT          3050

ATGTGTATAT CCATATCCAT ATATCCTATG ATTTTACTCT TTCTTTCATT          3100

TTTTTTAAAG AAACAAAACT ATGGAAATAA TACCCTACAG ATGAGCGAAA          3150

ATGTATTATT GTAAAGTTTA TTTTTTTTAA TAATGTTGTC TATGATGGGA          3200

AGAAAGGTAC CAGGACCCCT GAGCCCTGGT CCAGTTGGGC TGGTGGGGCT          3250

GTGGCCGGGG ACTCCCGATT GCATTCACTC TTAACCAAGC TCCAATAAAC          3300

GTACTAGGAA GCGAAAAAAA AAAAAAAAAA ACTCGAGGGG GGGCCCGGTA          3350

CCCAATTC                                                       3358

(2) INFORMATION FOR SEQ ID NO: 5:

(i) SEQUENCE CHARACTERISTICS:
        (A) LENGTH: 1392 base pairs
        (B) TYPE: Nucleic Acid
        (C) STRANDEDNESS: Single
        (D) TOPOLOGY: Linear (xi) SEQUENCE DESCRIPTION: SEQ ID NO: 5:

ATGATCTTGG CAAACGCCTT CTGCCTCTTC TTCTTTTTAG ACGAAACCCT            50

CCGCTCTTTG GCCAGCCCTT CCTCCCTGCA GGGCTCTGAG CTCCACGGCT           100

GGCGCCCCCA AGTGGACTGT GTCCGGGCCA ATGAGCTGTG TGCGGCTGAA           150

TCCAACTGCA GCTCCAGGTA CCGCACCCTT CGGCAGTGCC TGGCAGGCCG           200

GGATCGCAAT ACCATGCTGG CCAATAAGGA GTGCCAGGCA GCCCTGGAGG           250

TCTTGCAGGA AAGCCCACTG TATGACTGCC GCTGCAAGCG GGGCATGAAG           300

AAGGAGCTGC AGTGTCTGCA GATCTACTGG AGCATCCATC TGGGGCTGAC           350

AGAGGGTGAG GAGTTCTATG AAGCTTCCCC CTATGAGCCT GTGACCTCGC           400

GCCTCTCGGA CATCTTCAGG CTCGCTTCAA TCTTCTCAGG GACAGGGACA           450

GACCCGGCGG TCAGTACCAA AAGCAACCAC TGCCTGGATG CCGCCAAGGC           500

CTGCAACCTG AATGACAACT GCAAGAAGCT TCGCTCCTCT TATATCTCCA           550

TCTGCAACCG TGAGATCTCT CCCACCGAAC GCTGCAACCG CCGCAAGTGC           600

CACAAGGCTC TGCGCCAGTT CTTTGACCGT GTGCCCAGCG AGTATACCTA           650

CCGCATGCTC TTCTGCTCCT GTCAGGACCA GGCATGTGCT GAGCGTCGCC           700

GGCAAACCAT CCTGCCCAGT TGCTCCTATG AGGACAAGGA GAAGCCCAAC           750

TGCCTGGACC TGCGCAGCCT GTGTCGTACA GACCACCTGT GCCGGTCCCG           800

ACTGGCAGAT TTCCACGCCA ACTGTCGAGC CTCCTACCGG ACAATCACCA           850

GCTGTCCTGC GGACAACTAC CAGGCATGTC TGGGCTCCTA TGCTGGCATG           900

ATTGGGTTTG ATATGACACC CAACTATGTG GACTCCAACC CCACGGGCAT           950

CGTGGTGTCT CCCTGGTGCA ATTGTCGTGG CAGTGGGAAC ATGGAAGAAG          1000

AGTGTGAGAA GTTCCTCAGG GACTTCACGG AAAACCCATG CCTCCGGAAT          1050

GCCATTCAGG CCTTTGGTAA TGGCACAGAT GTGAACATGT CTCCCAAAGG          1100
```

-continued

```
CCCCTCACTC CCAGCTACCC AGGCCCCTCG GGTGGAGAAG ACTCCTTCAC      1150

TGCCAGATGA CCTCAGTGAC AGCACCAGCC TGGGGACCAG TGTCATCACC      1200

ACCTGCACAT CTATCCAGGA GCAAGGGCTG AAGGCCAACA ACTCCAAAGA      1250

GTTAAGCATG TGCTTCACAG AGCTCACGAC AAACATCAGT CCAGGGAGTA      1300

AAAAGGTGAT CAAACTTAAC TCAGGCTCCA GCAGAGCCAC ACTGTCGGCT      1350

GCCTTGACTG CCCTCCCACT CCTGATGCTG ACCTTGGCCT TG             1392
```

(2) INFORMATION FOR SEQ ID NO: 6:

(i) SEQUENCE CHARACTERISTICS:
        (A) LENGTH: 464 amino acids
        (B) TYPE: Amino Acid
        (D) TOPOLOGY: Linear (xi) SEQUENCE DESCRIPTION: SEQ ID NO: 6:

```
Met Ile Leu Ala Asn Ala Phe Cys Leu Phe Phe Leu Asp Glu
 1               5                  10                 15

Thr Leu Arg Ser Leu Ala Ser Pro Ser Ser Leu Gln Gly Ser Glu
                20                  25                 30

Leu His Gly Trp Arg Pro Gln Val Asp Cys Val Arg Ala Asn Glu
                35                  40                 45

Leu Cys Ala Ala Glu Ser Asn Cys Ser Ser Arg Tyr Arg Thr Leu
                50                  55                 60

Arg Gln Cys Leu Ala Gly Arg Asp Arg Asn Thr Met Leu Ala Asn
                65                  70                 75

Lys Glu Cys Gln Ala Ala Leu Glu Val Leu Gln Glu Ser Pro Leu
                80                  85                 90

Tyr Asp Cys Arg Cys Lys Arg Gly Met Lys Lys Glu Leu Gln Cys
                95                 100                105

Leu Gln Ile Tyr Trp Ser Ile His Leu Gly Leu Thr Glu Gly Glu
               110                 115                120

Glu Phe Tyr Glu Ala Ser Pro Tyr Glu Pro Val Thr Ser Arg Leu
               125                 130                135

Ser Asp Ile Phe Arg Leu Ala Ser Ile Phe Ser Gly Thr Gly Thr
               140                 145                150

Asp Pro Ala Val Ser Thr Lys Ser Asn His Cys Leu Asp Ala Ala
               155                 160                165

Lys Ala Cys Asn Leu Asn Asp Asn Cys Lys Lys Leu Arg Ser Ser
               170                 175                180

Tyr Ile Ser Ile Cys Asn Arg Glu Ile Ser Pro Thr Glu Arg Cys
               185                 190                195

Asn Arg Arg Lys Cys His Lys Ala Leu Arg Gln Phe Phe Asp Arg
               200                 205                210

Val Pro Ser Glu Tyr Thr Tyr Arg Met Leu Phe Cys Ser Cys Gln
               215                 220                225

Asp Gln Ala Cys Ala Glu Arg Arg Arg Gln Thr Ile Leu Pro Ser
               230                 235                240

Cys Ser Tyr Glu Asp Lys Glu Lys Pro Asn Cys Leu Asp Leu Arg
               245                 250                255

Ser Leu Cys Arg Thr Asp His Leu Cys Arg Ser Arg Leu Ala Asp
               260                 265                270

Phe His Ala Asn Cys Arg Ala Ser Tyr Arg Thr Ile Thr Ser Cys
               275                 280                285
```

```
Pro Ala Asp Asn Tyr Gln Ala Cys Leu Gly Ser Tyr Ala Gly Met
                290                 295                 300

Ile Gly Phe Asp Met Thr Pro Asn Tyr Val Asp Ser Asn Pro Thr
                305                 310                 315

Gly Ile Val Val Ser Pro Trp Cys Asn Cys Arg Gly Ser Gly Asn
                320                 325                 330

Met Glu Glu Glu Cys Glu Lys Phe Leu Arg Asp Phe Thr Glu Asn
                335                 340                 345

Pro Cys Leu Arg Asn Ala Ile Gln Ala Phe Gly Asn Gly Thr Asp
                350                 355                 360

Val Asn Met Ser Pro Lys Gly Pro Ser Leu Pro Ala Thr Gln Ala
                365                 370                 375

Pro Arg Val Glu Lys Thr Pro Ser Leu Pro Asp Asp Leu Ser Asp
                380                 385                 390

Ser Thr Ser Leu Gly Thr Ser Val Ile Thr Thr Cys Thr Ser Ile
                395                 400                 405

Gln Glu Gln Gly Leu Lys Ala Asn Asn Ser Lys Glu Leu Ser Met
                410                 415                 420

Cys Phe Thr Glu Leu Thr Thr Asn Ile Ser Pro Gly Ser Lys Lys
                425                 430                 435

Val Ile Lys Leu Asn Ser Gly Ser Ser Arg Ala Arg Leu Ser Ala
                440                 445                 450

Ala Leu Thr Ala Leu Pro Leu Leu Met Leu Thr Leu Ala Leu
                455                 460             464
```

(2) INFORMATION FOR SEQ ID NO: 7:

(i) SEQUENCE CHARACTERISTICS:
        (A) LENGTH: 229 base pairs
        (B) TYPE: Nucleic Acid
        (C) STRANDEDNESS: Single
        (D) TOPOLOGY: Linear (xi) SEQUENCE DESCRIPTION: SEQ ID NO: 7:

```
CCAAGAGCAA CCATTGCCTG GATGCTGCCA AGGCCTGCAA CCTGAATGAC           50

AACTGCAAGA AGCTGCGCTC CTCCTACATC TCCATCTGCA ACCGCGAGAT          100

CTCGCCCACC GAGCGCTGCA ACCGCCGCAA GTGCCACAAG GCCCTGCGCC          150

AGTTCTTCGA CCGGGTGCCC AGCGAGTACA CCTACCGCAT GCTCTTCTGC          200

TCCTGCCAAG ATCAGGCGTG CGCTGAGNC                                  229
```

(2) INFORMATION FOR SEQ ID NO: 8:

(i) SEQUENCE CHARACTERISTICS:
        (A) LENGTH: 521 base pairs
        (B) TYPE: Nucleic Acid
        (C) STRANDEDNESS: Single
        (D) TOPOLOGY: Linear (xi) SEQUENCE DESCRIPTION: SEQ ID NO: 8:

```
CAACCATTGC CTGGGATGCT GCCAAGGCCT GCAACCTGAA TGACAACTGC           50

AAGAAGCTGC GCTCCTCCTA CATCTCCATC TGCAACCGCG AGATCTCGCC          100

CACCGAGCGC TGCAACCGCC GCAAGTGCCA CAAGGCCCTG CGCCAGTTCT          150

TCGACCGGGT GCCCAGCGAG TACACCTACC GCATGCTCTT CTGCTCCTGC          200

CAAGACCAGG CGTGCGCTGA GCCGCGGNCA AAACCATCCT GCCCAGCTGC          250

TCCTATGAGG ACAAGGAGAA GCCCAACTGC CTGGGACCTG CGTGGCGTGT          300
```

```
GCCGGGACTG ACCACCTGTG TCGGTCCCGG CTNGGCCGAC TTTCCATGGC         350

CAATTTGTTG GAGCCTTCCT ACCAGACGGG TCANCAGGTT GCCTTGCGGA         400

CAATTTACCA GGGGTNTTTT GGGGTTTTTA TTGTTGGGCA TGGATTGGGG         450

TTTTGAAATT GANAATTAAT TTTGTTGGGA TTTNCAGGCC CCATTGGGCN         500

TTGTNGGTGN TTCCCCTGGG G                                       521

(2) INFORMATION FOR SEQ ID NO: 9:

(i) SEQUENCE CHARACTERISTICS:
        (A) LENGTH: 478 base pairs
        (B) TYPE: Nucleic Acid
        (C) STRANDEDNESS: Single
        (D) TOPOLOGY: Linear (xi) SEQUENCE DESCRIPTION: SEQ ID NO: 9:

TGACACCTAA CTATGTGGAC TCCAGCCCCA CTGGCATCGT GGTGTCCCCC          50

TGGTGCAGCT GTCGTGGCAG CGGGAACATG GAGGAGGAGT GTGAGAAGTT         100

CCTCAGGGAC TTCACCGAGA ACCCATGCCT CCGGAACGCC ATCCAGGCCT         150

TTGNAACGGC ACGGACGTGA ACGTGTCCCC AAAAGGCCCC TCGTTCCAGG         200

CCACCCAGGC CCTCGGGTGG AGAAGACGCC TTCTTTGCCA GATGACCTCA         250

GTGACAGTAC CAGCTTGGGG ACCAGTGTCA TCACCACCTG CACGTCTGTC         300

CAGGAGCAGG GGCTGAAGGC CAACAACTCC AAAGAGTTAA GCATGTGCTT         350

CACAGAGCTC ACCGACAAAT ATCATCCCAG GGAGTAACAA GGTGATTCAA         400

ACCTAACTCA GGCCCCAGCA GAGCAAGACC GTCGGCTTGC CTTTGACCGT         450

GCTGTCTGTC CTGATGCTGA ACAGGCTT                                478

(2) INFORMATION FOR SEQ ID NO: 10:

(i) SEQUENCE CHARACTERISTICS:
        (A) LENGTH: 433 base pairs
        (B) TYPE: Nucleic Acid
        (C) STRANDEDNESS: Single
        (D) TOPOLOGY: Linear (xi) SEQUENCE DESCRIPTION: SEQ ID NO: 10:

GCAAGGTGTG TGTGTGTCTG TGTGTGTTTC CATTTCGTCA GGCGGCTGTT          50

CTTGTCTGCG TACTTTCAAA AATCTTCTGA CTCGGTTCCC ACAGCCTACA         100

AGGCCTGTTT CAGCATCAGG ACAGACAGCA CGGTCAAGGC AGCCGACGGT         150

CTGGCTCTGC TGGGGCCTGA GTTAGGTTTG ATCACCTTGT TACTCCCTGG         200

GATGATATTT GTCGTGAGCT CTGTGAAGCA CATGCTTAAC TCTTTGGAGT         250

TGTTGGCCTT CAGCCCCTGC TCCTGGACAG ACGTGCAGGT GGTGATGACA         300

CTGGGTCCCC AAGCTGGTAC TGTCACTGAG GTCATCTGGC AAAGAAGGCG         350

TCTTCTCCAC CCGAGGGGCC TGGGGTGGCT GGGAACGAGG GGGCCTTTTT         400

GGGGGACACG TTCACGTTCC GTTGCCGTTG CCA                          433

(2) INFORMATION FOR SEQ ID NO: 11:

(i) SEQUENCE CHARACTERISTICS:
        (A) LENGTH: 418 base pairs
        (B) TYPE: Nucleic Acid
        (C) STRANDEDNESS: Single
        (D) TOPOLOGY: Linear
```

(xi) SEQUENCE DESCRIPTION: SEQ ID NO: 11:

| | |
|---|---|
| TTTTTTTTTT TGGGAAAAAC AATTTTTTTT TTGCAAGGTG TGTGTGTGTC | 50 |
| TGTGTGTGTT TCCATTTCGT CAGGCGGCTG TTCTTGTCTG CGTANTTTTC | 100 |
| AAAAATCTTC TGACTCGGTT CCCACAGCCT ACAAGGCCTG TTTCAGCATC | 150 |
| AGGACAGACA GCACGGTCAA GGCAGCCGAC GGTCTGGCTC TGCTGGGGCC | 200 |
| TGAGTTAGGT TTGATCACCT TGTTACTCCC TGGGATGATA TTTNTCGTGA | 250 |
| GCTCTGTGAA GCACATGCTT AACTCTTTGG AGTTNTTGGC CTTCAGCCCC | 300 |
| TGCTCCTGGG ACAGAACGTG CAGGNTGGGT GATGACACTG GGNCCCCAAG | 350 |
| GCTGGGTACT GTCACTGAGG GTCATCTGGN CAAAGNAAGG NCGTTTTTCT | 400 |
| CCACCCGAGG GGCCGGGG | 418 |

(2) INFORMATION FOR SEQ ID NO: 12:

(i) SEQUENCE CHARACTERISTICS:
        (A) LENGTH: 364 base pairs
        (B) TYPE: Nucleic Acid
        (C) STRANDEDNESS: Single
        (D) TOPOLOGY: Linear (xi) SEQUENCE DESCRIPTION: SEQ ID NO: 12:

| | |
|---|---|
| TGTGTGTGTC TGTGTGTGTT TCCATTTCGT CAGGCGGCTG TTCTTGTCTG | 50 |
| CGTAGTTTCA AAAATCTTCT GACTCGGTTC CCACAGCCTA CAAGGNCTGT | 100 |
| TTCAGCATCA GGACAGACAG CACGGTCAAG GCAGCCGACG GTCTGGCTCT | 150 |
| GCTGGGGCCT GAGTTAGGTT TGATCACCTT GTTACTCCCT GGGATGATAT | 200 |
| TTGTCGTGAG CTCTGTGAAG CACATGCTTA ACTCTTTGGA GTTGTTGGCC | 250 |
| TTCAGCCCCT GCTCCTGGAC AGACGTGCAG GTGGTNATGA CACTGGTCCC | 300 |
| CAAGCTGGTA CTNTCACTGA GGTCATCTGG CAAAGAAGGC GTCTTCTCCA | 350 |
| CCCNAGGGGC CTGG | 364 |

(2) INFORMATION FOR SEQ ID NO: 13:

(i) SEQUENCE CHARACTERISTICS:
        (A) LENGTH: 319 base pairs
        (B) TYPE: Nucleic Acid
        (C) STRANDEDNESS: Single
        (D) TOPOLOGY: Linear (xi) SEQUENCE DESCRIPTION: SEQ ID NO: 13:

| | |
|---|---|
| GGGAAAAACA ATTTTATTTT TGCAAGGTGT GTGTGTGTCT GTGTGTGTTT | 50 |
| CCATTTCGTC AGGCGGCTGT CCTTGTCTGC GTAGTTTCAA AAATCTTCTG | 100 |
| ACTCGGTTCC CACAGCCTAC AAGGCCTGTA TAAGCATCAG GACAGACAGC | 150 |
| ACGGTCAAGG CAGCCGACGG TCTGGCTCTG CTGGGGCCTG AGTAAGGTTT | 200 |
| GNCCACCTTG TAACTCCCTG GGATGATATT TGTCGTGAGC NCTGTNANGC | 250 |
| ACATGNTTAA CTCTTTGGAG TTNTTGGCCT TCAGCCCCTG CCCCTGGNCA | 300 |
| GACGTGCAGG TGGTGATGA | 319 |

(2) INFORMATION FOR SEQ ID NO: 14:

(i) SEQUENCE CHARACTERISTICS:
        (A) LENGTH: 309 base pairs
        (B) TYPE: Nucleic Acid (C) STRANDEDNESS: Single
        (D) TOPOLOGY: Linear (xi) SEQUENCE DESCRIPTION: SEQ ID NO: 14:

| | |
|---|---|
| GCTGAAACTG GCCTTGTAGG CTGTGGGAAC CGAGTCAGAA TATTTTTGAA | 50 |
| AGCTACGCAG ACAAGAACNG CGGCCTGACG AAATGGAAAC ACACACAGAC | 100 |
| ACACACACNC CTTGCATAAA AAAAATTGTT TTTCCCACCT TGTCGCTGAA | 150 |
| CCTGTCTCCT CCCAGGTTTC TTCTCTGGAG AAGTTTTTGT AAACCAAACA | 200 |
| GACAAGCAGG CAGGCAGCCT GAGAGCTGGC CCAGGGGTCC CCTGGTCAGG | 250 |
| GGAAACTCTG GTGCCGGGGA GGGCACGTGG CTCTAGAAAT GCCCTTCACT | 300 |
| TTCTCCTGG | 309 |

(2) INFORMATION FOR SEQ ID NO: 15:

(i) SEQUENCE CHARACTERISTICS:
        (A) LENGTH: 1995 base pairs
        (B) TYPE: Nucleic Acid
        (C) STRANDEDNESS: Single
        (D) TOPOLOGY: Linear (xi) SEQUENCE DESCRIPTION: SEQ ID NO: 15:

| | |
|---|---|
| ATGATCTTGG CAAACGTCTT CTTCCTCTTC TTCTTTCTAG ACGAGACCCT | 50 |
| CCGCTCTTTG GCCAGCCCTT CCTCCCTGCA GGACCCCGAG CTCCACGGCT | 100 |
| GGCGCCCCCC AGTGGACTGT GTCCGGGCCA ATGAGCTGTG TGCCGCCGAA | 150 |
| TCCAACTGCA GCTCTCGCTA CCGCACTCTG CGGCAGTGCC TGGCAGGCCG | 200 |
| CGACCGCAAC ACCATGCTGG CCAACAAGGA GTGCCAGGCG GCCTTGGAGG | 250 |
| TCTTGCAGGA GAGCCCGCTG TACGACTGCC GCTGCAAGCG GGGCATGAAG | 300 |
| AAGGAGCTGC AGTGTCTGCA GATCTACTGG AGCATCCACC TGGGGCTGAC | 350 |
| CGAGGGTGAG GAGTTCTACG AAGCCTCCCC CTATGAGCCG GTGACCTCCC | 400 |
| GCCTCTCGGA CATCTTCAGG CTTGCTTCAA TCTTCTCAGG GACAGGGGCA | 450 |
| GACCCGGTGG TCAGCGCCAA GAGCAACCAT TGCCTGGATG CTGCCAAGGC | 500 |
| CTGCAACCTG AATGACAACT GCAAGAAGCT GCGCTCCTCC TACATCTCCA | 550 |
| TCTGCAACCG CGAGATCTCG CCCACCGAGC GCTGCAACCG CCGCAAGTGC | 600 |
| CACAAGGCCC TGCGCCAGTT CTTCGACCGG GTGCCCAGCG AGTACACCTA | 650 |
| CCGCATGCTC TTCTGCTCCT GCCAAGACCA GGCGTGCGCT GAGCGCCGCC | 700 |
| GGCAAACCAT CCTGCCCAGC TGCTCCTATG AGGACAAGGA GAAGCCCAAC | 750 |
| TGCCTGGACC TGCGTGGCGT GTGCCGGACT GACCACCTGT GTCGGTCCCG | 800 |
| GCTGGCCGAC TTCCATGCCA ATTGTCGAGC CTCCTACCAG ACGGTCACCA | 850 |
| GCTGCCCTGC GGACAATTAC CAGGCGTGTC TGGGCTCTTA TGCTGGCATG | 900 |
| ATTGGGTTTG ACATGACACC TAACTATGTG GACTCCAGCC CCACTGGCAT | 950 |
| CGTGGTGTCC CCCTGGTGCA GCTGTCGTGG CAGCGGGAAC ATGGAGGAGG | 1000 |
| AGTGTGAGAA GTTCCTCAGG GACTTCACCG AGAACCCATG CCTCCGGAAC | 1050 |
| GCCATCCAGG CCTTTGGCAA CGGCACGGAC GTGAACGTGT CCCCAAAAGG | 1100 |
| CCCCTCGTTC CAGGCCACCC AGGCCCCTCG GGTGGAGAAG ACGCCTTCTT | 1150 |
| TGCCAGATGA CCTCAGTGAC AGTACCAGCT TGGGGACCAG TGTCATCACC | 1200 |
| ACCTGCACGT CTGTCCAGGA GCAGGGGCTG AAGGCCAACA ACTCCAAAGA | 1250 |

```
GTTAAGCATG TGCTTCACAG AGCTCACGAC AAATATCATC CCAGGGCCTA          1300

GGGACCCGGT GGACAAAACT CACACATGCC CACCGTGCCC AGCACCTGAA          1350

CTCCTGGGGG GACCGTCAGT CTTCCTCTTC CCCCCAAAAC CCAAGGACAC          1400

CCTCATGATC TCCCGGACCC CTGAGGTCAC ATGCGTGGTG GTGGACGTGA          1450

GCCACGAAGA CCCTGAGGTC AAGTTCAACT GGTACGTGGA CGGCGTGGAG          1500

GTGCATAATG CCAAGACAAA GCCGCGGGAG GAGCAGTACA ACAGCACGTA          1550

CCGTGTGGTC AGCGTCCTCA CCGTCCTGCA CCAGGACTGG CTGAATGGCA          1600

AGGAGTACAA GTGCAAGGTC TCCAACAAAG CCCTCCCAGC CCCCATCGAG          1650

AAAACCATCT CCAAAGCCAA AGGGCAGCCC CGAGAACCAC AGGTGTACAC          1700

CCTGCCCCCA TCCCGGGAAG AGATGACCAA GAACCAGGTC AGCCTGACCT          1750

GCCTGGTCAA AGGCTTCTAT CCCAGCGACA TCGCCGTGGA GTGGGAGAGC          1800

AATGGGCAGC CGGAGAACAA CTACAAGACC ACGCCTCCCG TGCTGGACTC          1850

CGACGGCTCC TTCTTCCTCT ACAGCAAGCT CACCGTGGAC AAGAGCAGGT          1900

GGCAGCAGGG GAACGTCTTC TCATGCTCCG TGATGCATGA GGCTCTGCAC          1950

AACCACTACA CGCAGAAGAG CCTCTCCCTG TCTCCGGGTA AATGA              1995

(2) INFORMATION FOR SEQ ID NO: 16:

(i) SEQUENCE CHARACTERISTICS:
        (A) LENGTH: 664 amino acids
        (B) TYPE: Amino Acid
        (D) TOPOLOGY: Linear (xi) SEQUENCE DESCRIPTION: SEQ ID NO: 16:

Met Ile Leu Ala Asn Val Phe Phe Leu Phe Phe Phe Leu Asp Glu
 1               5                  10                  15

Thr Leu Arg Ser Leu Ala Ser Pro Ser Ser Leu Gln Asp Pro Glu
                20                  25                  30

Leu His Gly Trp Arg Pro Pro Val Asp Cys Val Arg Ala Asn Glu
                35                  40                  45

Leu Cys Ala Ala Glu Ser Asn Cys Ser Ser Arg Tyr Arg Thr Leu
                50                  55                  60

Arg Gln Cys Leu Ala Gly Arg Asp Arg Asn Thr Met Leu Ala Asn
                65                  70                  75

Lys Glu Cys Gln Ala Ala Leu Glu Val Leu Gln Glu Ser Pro Leu
                80                  85                  90

Tyr Asp Cys Arg Cys Lys Arg Gly Met Lys Lys Glu Leu Gln Cys
                95                 100                 105

Leu Gln Ile Tyr Trp Ser Ile His Leu Gly Leu Thr Glu Gly Glu
               110                 115                 120

Glu Phe Tyr Glu Ala Ser Pro Tyr Glu Pro Val Thr Ser Arg Leu
               125                 130                 135

Ser Asp Ile Phe Arg Leu Ala Ser Ile Phe Ser Gly Thr Gly Ala
               140                 145                 150

Asp Pro Val Val Ser Ala Lys Ser Asn His Cys Leu Asp Ala Ala
               155                 160                 165

Lys Ala Cys Asn Leu Asn Asp Asn Cys Lys Lys Leu Arg Ser Ser
               170                 175                 180

Tyr Ile Ser Ile Cys Asn Arg Glu Ile Ser Pro Thr Glu Arg Cys
               185                 190                 195
```

-continued

```
Asn Arg Arg Lys Cys His Lys Ala Leu Arg Gln Phe Phe Asp Arg
            200                 205                 210
Val Pro Ser Glu Tyr Thr Tyr Arg Met Leu Phe Cys Ser Cys Gln
            215                 220                 225
Asp Gln Ala Cys Ala Glu Arg Arg Gln Thr Ile Leu Pro Ser
            230                 235                 240
Cys Ser Tyr Glu Asp Lys Glu Lys Pro Asn Cys Leu Asp Leu Arg
            245                 250                 255
Gly Val Cys Arg Thr Asp His Leu Cys Arg Ser Arg Leu Ala Asp
            260                 265                 270
Phe His Ala Asn Cys Arg Ala Ser Tyr Gln Thr Val Thr Ser Cys
            275                 280                 285
Pro Ala Asp Asn Tyr Gln Ala Cys Leu Gly Ser Tyr Ala Gly Met
            290                 295                 300
Ile Gly Phe Asp Met Thr Pro Asn Tyr Val Asp Ser Ser Pro Thr
            305                 310                 315
Gly Ile Val Val Ser Pro Trp Cys Ser Cys Arg Gly Ser Gly Asn
            320                 325                 330
Met Glu Glu Glu Cys Glu Lys Phe Leu Arg Asp Phe Thr Glu Asn
            335                 340                 345
Pro Cys Leu Arg Asn Ala Ile Gln Ala Phe Gly Asn Gly Thr Asp
            350                 355                 360
Val Asn Val Ser Pro Lys Gly Pro Ser Phe Gln Ala Thr Gln Ala
            365                 370                 375
Pro Arg Val Glu Lys Thr Pro Ser Leu Pro Asp Asp Leu Ser Asp
            380                 385                 390
Ser Thr Ser Leu Gly Thr Ser Val Ile Thr Thr Cys Thr Ser Val
            395                 400                 405
Gln Glu Gln Gly Leu Lys Ala Asn Asn Ser Lys Glu Leu Ser Met
            410                 415                 420
Cys Phe Thr Glu Leu Thr Thr Asn Ile Ile Pro Gly Pro Arg Asp
            425                 430                 435
Pro Val Asp Lys Thr His Thr Cys Pro Pro Cys Pro Ala Pro Glu
            440                 445                 450
Leu Leu Gly Gly Pro Ser Val Phe Leu Phe Pro Pro Lys Pro Lys
            455                 460                 465
Asp Thr Leu Met Ile Ser Arg Thr Pro Glu Val Thr Cys Val Val
            470                 475                 480
Val Asp Val Ser His Glu Asp Pro Glu Val Lys Phe Asn Trp Tyr
            485                 490                 495
Val Asp Gly Val Glu Val His Asn Ala Lys Thr Lys Pro Arg Glu
            500                 505                 510
Glu Gln Tyr Asn Ser Thr Tyr Arg Val Val Ser Val Leu Thr Val
            515                 520                 525
Leu His Gln Asp Trp Leu Asn Gly Lys Glu Tyr Lys Cys Lys Val
            530                 535                 540
Ser Asn Lys Ala Leu Pro Ala Pro Ile Glu Lys Thr Ile Ser Lys
            545                 550                 555
Ala Lys Gly Gln Pro Arg Glu Pro Gln Val Tyr Thr Leu Pro Pro
            560                 565                 570
Ser Arg Glu Glu Met Thr Lys Asn Gln Val Ser Leu Thr Cys Leu
            575                 580                 585
```

```
Val Lys Gly Phe Tyr Pro Ser Asp Ile Ala Val Glu Trp Glu Ser
                590                 595                 600

Asn Gly Gln Pro Glu Asn Asn Tyr Lys Thr Thr Pro Pro Val Leu
                605                 610                 615

Asp Ser Asp Gly Ser Phe Phe Leu Tyr Ser Lys Leu Thr Val Asp
                620                 625                 630

Lys Ser Arg Trp Gln Gln Gly Asn Val Phe Ser Cys Ser Val Met
                635                 640                 645

His Glu Ala Leu His Asn His Tyr Thr Gln Lys Ser Leu Ser Leu
                650                 655                 660

Ser Pro Gly Lys
            664

(2) INFORMATION FOR SEQ ID NO: 17:

(i) SEQUENCE CHARACTERISTICS:
        (A) LENGTH: 1995 base pairs
        (B) TYPE: Nucleic Acid
        (C) STRANDEDNESS: Single
        (D) TOPOLOGY: Linear (xi) SEQUENCE DESCRIPTION: SEQ ID NO: 17:
```

| | |
|---|---:|
| ATGATCTTGG CAAACGCCTT CTGCCTCTTC TTCTTTTTAG ACGAAACCCT | 50 |
| CCGCTCTTTG GCCAGCCCTT CCTCCCTGCA GGGCTCTGAG CTCCACGGCT | 100 |
| GGCGCCCCCA AGTGGACTGT GTCCGGGCCA ATGAGCTGTG TGCGGCTGAA | 150 |
| TCCAACTGCA GCTCCAGGTA CCGCACCCTT CGGCAGTGCC TGGCAGGCCG | 200 |
| GGATCGCAAT ACCATGCTGG CCAATAAGGA GTGCCAGGCA GCCCTGGAGG | 250 |
| TCTTGCAGGA AAGCCCACTG TATGACTGCC GCTGCAAGCG GGGCATGAAG | 300 |
| AAGGAGCTGC AGTGTCTGCA GATCTACTGG AGCATCCATC TGGGGCTGAC | 350 |
| AGAGGGTGAG GAGTTCTATG AAGCTTCCCC CTATGAGCCT GTGACCTCGC | 400 |
| GCCTCTCGGA CATCTTCAGG CTCGCTTCAA TCTTCTCAGG GACAGGGACA | 450 |
| GACCCGGCGG TCAGTACCAA AAGCAACCAC TGCCTGGATG CCGCCAAGGC | 500 |
| CTGCAACCTG AATGACAACT GCAAGAAGCT TCGCTCCTCT TATATCTCCA | 550 |
| TCTGCAACCG TGAGATCTCT CCCACCGAAC GCTGCAACCG CCGCAAGTGC | 600 |
| CACAAGGCTC TGCGCCAGTT CTTTGACCGT GTGCCCAGCG AGTATACCTA | 650 |
| CCGCATGCTC TTCTGCTCCT GTCAGGACCA GGCATGTGCT GAGCGTCGCC | 700 |
| GGCAAACCAT CCTGCCCAGT TGCTCCTATG AGGACAAGGA GAAGCCCAAC | 750 |
| TGCCTGGACC TGCGCAGCCT GTGTCGTACA GACCACCTGT GCCGGTCCCG | 800 |
| ACTGGCAGAT TTCCACGCCA ACTGTCGAGC CTCCTACCGG ACAATCACCA | 850 |
| GCTGTCCTGC GGACAACTAC CAGGCATGTC TGGGCTCCTA TGCTGGCATG | 900 |
| ATTGGGTTTG ATATGACACC CAACTATGTG GACTCCAACC CCACGGGCAT | 950 |
| CGTGGTGTCT CCCTGGTGCA ATTGTCGTGG CAGTGGGAAC ATGGAAGAAG | 1000 |
| AGTGTGAGAA GTTCCTCAGG GACTTCACGG AAAACCCATG CCTCCGGAAT | 1050 |
| GCCATTCAGG CCTTTGGTAA TGGCACAGAT GTGAACATGT CTCCCAAAGG | 1100 |
| CCCCTCACTC CCAGCTACCC AGGCCCCTCG GGTGGAGAAG ACTCCTTCAC | 1150 |
| TGCCAGATGA CCTCAGTGAC AGCACCAGCC TGGGGACCAG TGTCATCACC | 1200 |
| ACCTGCACAT CTATCCAGGA GCAAGGGCTG AAGGCCAACA ACTCCAAAGA | 1250 |

```
GTTAAGCATG TGCTTCACAG AGCTCACGAC AAACATCAGT CCAGGGTCTA          1300

GAGACCCGGT GGACAAAACT CACACATGCC CACCGTGCCC AGCACCTGAA          1350

CTCCTGGGGG GACCGTCAGT CTTCCTCTTC CCCCCAAAAC CCAAGGACAC          1400

CCTCATGATC TCCCGGACCC CTGAGGTCAC ATGCGTGGTG GTGGACGTGA          1450

GCCACGAAGA CCCTGAGGTC AAGTTCAACT GGTACGTGGA CGGCGTGGAG          1500

GTGCATAATG CCAAGACAAA GCCGCGGGAG GAGCAGTACA ACAGCACGTA          1550

CCGTGTGGTC AGCGTCCTCA CCGTCCTGCA CCAGGACTGG CTGAATGGCA          1600

AGGAGTACAA GTGCAAGGTC TCCAACAAAG CCCTCCCAGC CCCCATCGAG          1650

AAAACCATCT CCAAAGCCAA AGGGCAGCCC CGAGAACCAC AGGTGTACAC          1700

CCTGCCCCCA TCCCGGGAAG AGATGACCAA GAACCAGGTC AGCCTGACCT          1750

GCCTGGTCAA AGGCTTCTAT CCCAGCGACA TCGCCGTGGA GTGGGAGAGC          1800

AATGGGCAGC CGGAGAACAA CTACAAGACC ACGCCTCCCG TGCTGGACTC          1850

CGACGGCTCC TTCTTCCTCT ACAGCAAGCT CACCGTGGAC AAGAGCAGGT          1900

GGCAGCAGGG GAACGTCTTC TCATGCTCCG TGATGCATGA GGCTCTGCAC          1950

AACCACTACA CGCAGAAGAG CCTCTCCCTG TCTCCGGGTA AATGA              1995

(2) INFORMATION FOR SEQ ID NO: 18:

(i) SEQUENCE CHARACTERISTICS:
        (A) LENGTH: 664 amino acids
        (B) TYPE: Amino Acid
        (D) TOPOLOGY: Linear (xi) SEQUENCE DESCRIPTION: SEQ ID NO: 18:

Met Ile Leu Ala Asn Ala Phe Cys Leu Phe Phe Phe Leu Asp Glu
  1               5                  10                  15

Thr Leu Arg Ser Leu Ala Ser Pro Ser Ser Leu Gln Gly Ser Glu
                 20                  25                  30

Leu His Gly Trp Arg Pro Gln Val Asp Cys Val Arg Ala Asn Glu
             35                  40                  45

Leu Cys Ala Ala Glu Ser Asn Cys Ser Ser Arg Tyr Arg Thr Leu
             50                  55                  60

Arg Gln Cys Leu Ala Gly Arg Asp Arg Asn Thr Met Leu Ala Asn
             65                  70                  75

Lys Glu Cys Gln Ala Ala Leu Glu Val Leu Gln Glu Ser Pro Leu
             80                  85                  90

Tyr Asp Cys Arg Cys Lys Arg Gly Met Lys Lys Glu Leu Gln Cys
             95                 100                 105

Leu Gln Ile Tyr Trp Ser Ile His Leu Gly Leu Thr Glu Gly Glu
            110                 115                 120

Glu Phe Tyr Glu Ala Ser Pro Tyr Glu Pro Val Thr Ser Arg Leu
            125                 130                 135

Ser Asp Ile Phe Arg Leu Ala Ser Ile Phe Ser Gly Thr Gly Thr
            140                 145                 150

Asp Pro Ala Val Ser Thr Lys Ser Asn His Cys Leu Asp Ala Ala
            155                 160                 165

Lys Ala Cys Asn Leu Asn Asp Asn Cys Lys Lys Leu Arg Ser Ser
            170                 175                 180

Tyr Ile Ser Ile Cys Asn Arg Glu Ile Ser Pro Thr Glu Arg Cys
            185                 190                 195
```

```
Asn Arg Arg Lys Cys His Lys Ala Leu Arg Gln Phe Phe Asp Arg
            200                 205                 210

Val Pro Ser Glu Tyr Thr Tyr Arg Met Leu Phe Cys Ser Cys Gln
            215                 220                 225

Asp Gln Ala Cys Ala Glu Arg Arg Gln Thr Ile Leu Pro Ser
            230                 235                 240

Cys Ser Tyr Glu Asp Lys Glu Lys Pro Asn Cys Leu Asp Leu Arg
            245                 250                 255

Ser Leu Cys Arg Thr Asp His Leu Cys Arg Ser Arg Leu Ala Asp
            260                 265                 270

Phe His Ala Asn Cys Arg Ala Ser Tyr Arg Thr Ile Thr Ser Cys
            275                 280                 285

Pro Ala Asp Asn Tyr Gln Ala Cys Leu Gly Ser Tyr Ala Gly Met
            290                 295                 300

Ile Gly Phe Asp Met Thr Pro Asn Tyr Val Asp Ser Asn Pro Thr
            305                 310                 315

Gly Ile Val Val Ser Pro Trp Cys Asn Cys Arg Gly Ser Gly Asn
            320                 325                 330

Met Glu Glu Glu Cys Glu Lys Phe Leu Arg Asp Phe Thr Glu Asn
            335                 340                 345

Pro Cys Leu Arg Asn Ala Ile Gln Ala Phe Gly Asn Gly Thr Asp
            350                 355                 360

Val Asn Met Ser Pro Lys Gly Pro Ser Leu Pro Ala Thr Gln Ala
            365                 370                 375

Pro Arg Val Glu Lys Thr Pro Ser Leu Pro Asp Asp Leu Ser Asp
            380                 385                 390

Ser Thr Ser Leu Gly Thr Ser Val Ile Thr Thr Cys Thr Ser Ile
            395                 400                 405

Gln Glu Gln Gly Leu Lys Ala Asn Asn Ser Lys Glu Leu Ser Met
            410                 415                 420

Cys Phe Thr Glu Leu Thr Thr Asn Ile Ser Pro Gly Ser Arg Asp
            425                 430                 435

Pro Val Asp Lys Thr His Thr Cys Pro Pro Cys Pro Ala Pro Glu
            440                 445                 450

Leu Leu Gly Gly Pro Ser Val Phe Leu Phe Pro Pro Lys Pro Lys
            455                 460                 465

Asp Thr Leu Met Ile Ser Arg Thr Pro Glu Val Thr Cys Val Val
            470                 475                 480

Val Asp Val Ser His Glu Asp Pro Glu Val Lys Phe Asn Trp Tyr
            485                 490                 495

Val Asp Gly Val Glu Val His Asn Ala Lys Thr Lys Pro Arg Glu
            500                 505                 510

Glu Gln Tyr Asn Ser Thr Tyr Arg Val Val Ser Val Leu Thr Val
            515                 520                 525

Leu His Gln Asp Trp Leu Asn Gly Lys Glu Tyr Lys Cys Lys Val
            530                 535                 540

Ser Asn Lys Ala Leu Pro Ala Pro Ile Glu Lys Thr Ile Ser Lys
            545                 550                 555

Ala Lys Gly Gln Pro Arg Glu Pro Gln Val Tyr Thr Leu Pro Pro
            560                 565                 570

Ser Arg Glu Glu Met Thr Lys Asn Gln Val Ser Leu Thr Cys Leu
            575                 580                 585

Val Lys Gly Phe Tyr Pro Ser Asp Ile Ala Val Glu Trp Glu Ser
```

```
                    590                 595                 600
Asn Gly Gln Pro Glu Asn Asn Tyr Lys Thr Thr Pro Pro Val Leu
                605                 610                 615
Asp Ser Asp Gly Ser Phe Phe Leu Tyr Ser Lys Leu Thr Val Asp
                620                 625                 630
Lys Ser Arg Trp Gln Gln Gly Asn Val Phe Ser Cys Ser Val Met
                635                 640                 645
His Glu Ala Leu His Asn His Tyr Thr Gln Lys Ser Leu Ser Leu
                650                 655                 660
Ser Pro Gly Lys
        664

(2) INFORMATION FOR SEQ ID NO: 19:

(i) SEQUENCE CHARACTERISTICS:
        (A) LENGTH: 670 base pairs
        (B) TYPE: Nucleic Acid
        (C) STRANDEDNESS: Single
        (D) TOPOLOGY: Linear (xi) SEQUENCE DESCRIPTION: SEQ ID NO: 19:

CTGCAAGAAG CTGCGCTCCT CCTACATCTC CATCTGCAAC CGCGAGATCT         50

CGCCCACCGA GCGCTGCAAC CGCCGCAAGT GCCACAAGGC CCTGCGCCAG        100

TTCTTCGACC GGGTGCCCAG CGAGTACACC TACCGCATGC TCTTCTGCTC        150

CTGCCAAGAC CAGGCGTGCG CTGAGCGCCG CCGGCAAACC ATCCTGCCCA        200

GCTGCTCCTA TGAGGACAAG GAGAAGCCCA ACTGCCTGGA CCTGCGTGGC        250

GTGTGCCGGA CTGACCACCT GTGTCGGTCC CGGCTGGCCG ACTTCCATGC        300

CAATTGTCGA GCCTCCTACC AGACGGTCAC CAGCTGCCCT GCGGACAATT        350

ACCAGGCGTG TCTGGGCTCT TATGCTGGCA TGATTGGGTT TGACATGACA        400

CCTAACTATG TGGACTCCAG CCCCACTGGC ATCGTGGTGT CCCCTGGTGC        450

AGCTGTCGTG GCAGCGGGAA CATGGAGGAG GAGTGTGAGA AGTTCCTCAG        500

GACTTCACCG AGAACCCATG CCTCCGGAAC GCCATCCAGG CCTTTGGCAA        550

CGGCACGGAC GTGAACGTGT CCCCAAAAGG CCCTCGTTCC AGGCCACCCA        600

GGCCCCTCGG GTGGAGAAGA CGCCTTCTTT GCCAGATGAC CTCAGTGACA        650

GTACCAGCTT GGGGACCAGT                                        670
```